(12) United States Patent
Jung et al.

(10) Patent No.: US 11,673,875 B2
(45) Date of Patent: Jun. 13, 2023

(54) ORGANIC COMPOUND, ORGANIC OPTOELECTRIC DIODE, AND DISPLAY DEVICE

(71) Applicant: SAMSUNG SDI CO., LTD., Yongin-si (KR)

(72) Inventors: Sung-Hyun Jung, Suwon-si (KR); Dong Wan Ryu, Suwon-si (KR); Chang Ju Shin, Suwon-si (KR); Hanill Lee, Suwon-si (KR); Chunkeun Jang, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 577 days.

(21) Appl. No.: 15/736,177

(22) PCT Filed: Jul. 21, 2016

(86) PCT No.: PCT/KR2016/007966
§ 371 (c)(1),
(2) Date: Dec. 13, 2017

(87) PCT Pub. No.: WO2017/043757
PCT Pub. Date: Mar. 16, 2017

(65) Prior Publication Data
US 2018/0186764 A1 Jul. 5, 2018

(30) Foreign Application Priority Data

Sep. 9, 2015 (KR) .................. 10-2015-0127668

(51) Int. Cl.
| | | |
|---|---|---|
| *H01L 51/54* | (2006.01) | |
| *C07D 333/76* | (2006.01) | |
| *C09K 11/06* | (2006.01) | |
| *H05B 33/14* | (2006.01) | |
| *H01L 51/00* | (2006.01) | |
| *C07D 307/92* | (2006.01) | |
| *C07D 307/91* | (2006.01) | |
| *H01L 51/50* | (2006.01) | |

(52) U.S. Cl.
CPC ......... *C07D 333/76* (2013.01); *C07D 307/91* (2013.01); *C07D 307/92* (2013.01); *C09K 11/06* (2013.01); *H01L 51/006* (2013.01); *H01L 51/0061* (2013.01); *H01L 51/0073* (2013.01); *H01L 51/0074* (2013.01); *H05B 33/14* (2013.01); *C09K 2211/1088* (2013.01); *C09K 2211/1092* (2013.01); *H01L 51/0085* (2013.01); *H01L 51/5012* (2013.01); *H01L 2251/308* (2013.01)

(58) Field of Classification Search
CPC .. C07D 307/91; C07D 307/92; C07D 333/76; H05B 33/14; C09K 11/06; C09K 2211/00; C09K 2211/10; C09K 2211/1088; C09K 221/1092; H01L 51/0032; H01L 51/005; H01L 51/0072; H01L 51/0073; H01L 51/0074; H01L 51/0067; H01L 51/0061; H01L 51/006; H01L 51/0085; H01L 51/50; H01L 51/5012; H01L 51/5016; H01L 51/5056; H01L 2251/308
See application file for complete search history.

(56) References Cited

U.S. PATENT DOCUMENTS

| | | | | |
|---|---|---|---|---|
| 2009/0160323 | A1* | 6/2009 | Nomura | ................ H01L 51/006 |
| | | | | 313/504 |
| 2014/0225073 | A1 | 8/2014 | Lee et al. | |

FOREIGN PATENT DOCUMENTS

| | | |
|---|---|---|
| CN | 101952250 A | 1/2011 |
| CN | 102046613 A | 5/2011 |
| CN | 102596907 A | 7/2012 |
| CN | 106132944 A | 11/2016 |
| JP | 2007-049055 A | 2/2007 |
| JP | 3983215 B | 9/2007 |
| JP | 2009-170819 A | 7/2009 |
| JP | 2011-006405 A | 1/2011 |
| JP | 4765589 B | 9/2011 |
| JP | 2012-046478 A | 3/2012 |
| JP | 2012-067093 A | 4/2012 |
| JP | WO 2010-052932 A | 4/2012 |
| JP | 5202759 B | 6/2013 |
| JP | 2014-139987 A | 7/2014 |
| KR | 10-2004-0025826 A | 3/2004 |
| KR | 10-2011-0044159 A | 4/2011 |
| KR | 10-1084287 B | 11/2011 |
| KR | 10-1093122 B | 12/2011 |
| KR | 10-2012-0014913 A | 2/2012 |
| KR | 10-2012-0025984 A | 3/2012 |
| KR | 10-2012-0060611 A | 6/2012 |
| KR | 10-2012-0113735 A | 10/2012 |
| KR | 10-2013-0058086 A | 6/2013 |
| KR | 10-1297161 B | 8/2013 |
| KR | 10-2014-0092962 A | 7/2014 |
| KR | 10-2014-0101225 A | 8/2014 |
| KR | 10-2015-0034390 A | 4/2015 |
| KR | 10-2015-0039673 A | 4/2015 |
| KR | 10-2015-0129606 A | 11/2015 |
| WO | WO 2014-123238 A1 | 8/2014 |
| WO | WO-2014123238 A1 * | 8/2014 ......... H01L 51/0058 |
| WO | WO 2015-046955 A1 | 4/2015 |
| WO | WO 2015-050391 A1 | 4/2015 |

(Continued)

OTHER PUBLICATIONS

International Search Report from PCT/KR2016/007966.
(Continued)

*Primary Examiner* — Andrew K Bohaty
(74) *Attorney, Agent, or Firm* — Lee IP Law, P.C.

(57) ABSTRACT

The present invention relates to an organic compound represented by Chemical Formula 1, an organic optoelectronic diode, and a display device.

10 Claims, 1 Drawing Sheet

(56) References Cited

FOREIGN PATENT DOCUMENTS

| WO | WO-2015084114 A1 * | 6/2015 | ........... C07C 211/54 |
| WO | WO 2015-174639 A1 | 11/2015 | |

OTHER PUBLICATIONS

Office Action dated Jul. 19, 2018, and the accompanying Search Report dated Jul. 17, 2018, of the corresponding Taiwanese Patent Application No. 105122977.
Chinese Office action dated Aug. 19, 2020.

* cited by examiner

[Fig 1]
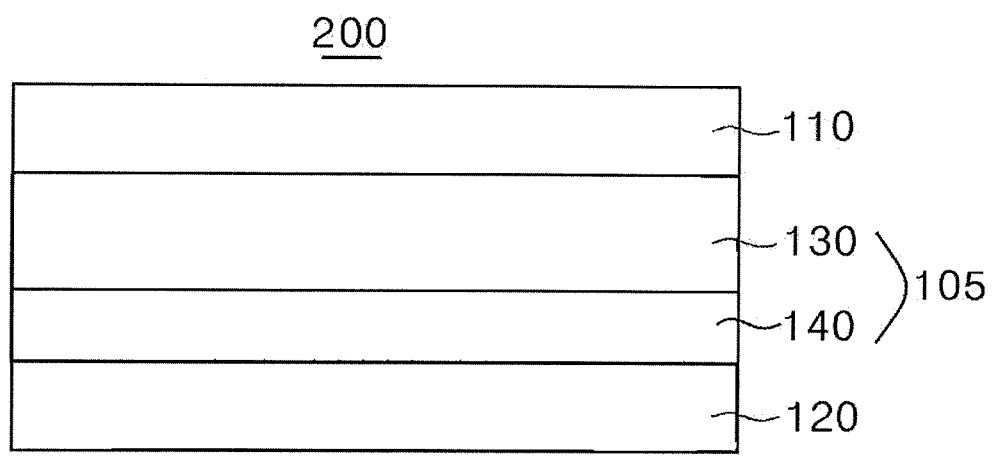
[Fig 2]
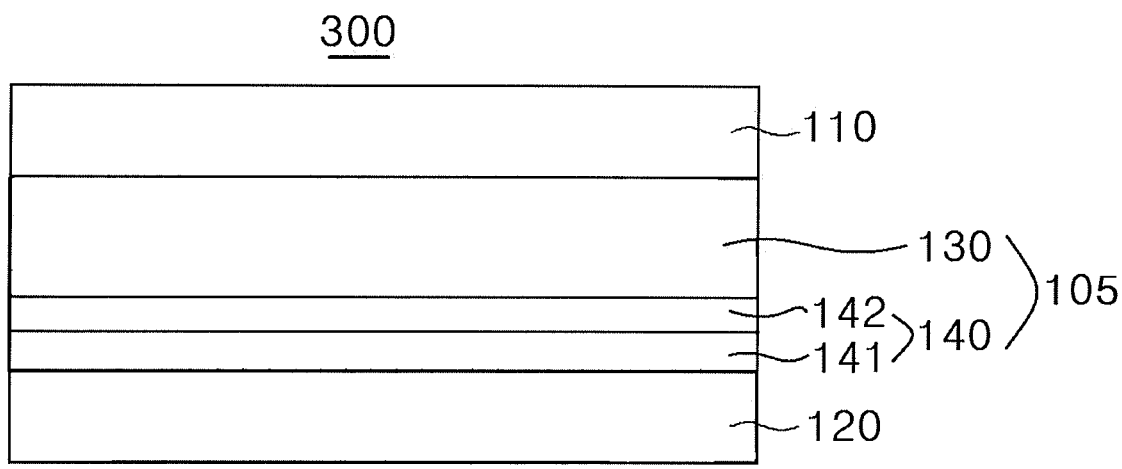

ORGANIC COMPOUND, ORGANIC OPTOELECTRIC DIODE, AND DISPLAY DEVICE

CROSS REFERENCE TO RELATED APPLICATIONS

This is the U.S. national phase application based on PCT Application No. PCT/KR2016/007966, filed Jul. 21, 2016, which is based on Korean Patent Application No. 10-2015-0127668, filed Sep. 9, 2015, the entire contents of all of which are hereby incorporated by reference.

TECHNICAL FIELD

An organic compound, an organic optoelectronic device, and a display diode are disclosed.

BACKGROUND ART

An organic optoelectronic device is a device that converts electrical energy into photoenergy, and vice versa.

An organic optoelectronic device may be classified as follows in accordance with its driving principles. One is an optoelectronic device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, an organic photo conductor drum, and the like.

Of these, an organic light emitting diode (OLED) has recently drawn attention due to an increase in demand for flat panel displays. The organic light emitting diode converts electrical energy into light by applying current to an organic light emitting material and has a structure in which an organic layer is interposed between an anode and a cathode. Herein, the organic layer may include an emission layer and optionally an auxiliary layer, and the auxiliary layer may be, for example at least one selected from a hole injection layer, a hole transport layer, an electron blocking layer, an electron transport layer, an electron transport auxiliary layer, an electron injection layer, and a hole blocking layer for improving efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides an organic compound capable of realizing an organic optoelectronic device having high efficiency and long life-span.

Another embodiment provides an organic optoelectronic device including the organic compound.

Yet another embodiment provides a display device including the organic optoelectronic device.

Technical Solution

According to an embodiment, an organic compound represented by Chemical Formula 1 is provided.

[Chemical Formula 1]

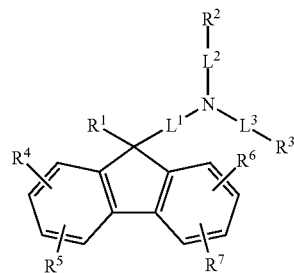

In Chemical Formula 1, $L^1$ to $L^3$ are independently a single bond, a substituted or unsubstituted C6 to C30 arylene group, a substituted or unsubstituted C2 to C30 heterocyclic group, or a combination thereof, $R^1$ to $R^7$ are independently hydrogen, deuterium, a substituted or unsubstituted C1 to C30 alkyl group, a substituted or unsubstituted C3 to C30 cycloalkyl group, a substituted or unsubstituted C2 to C30 heterocyclic group, a substituted or unsubstituted C6 to C30 aryl group, a halogen, a cyano group, a hydroxyl group, an amino group, a nitro group, or a combination thereof, $R^4$ to $R^7$ are independently present or adjacent two are linked to each other to provide a ring, and at least one of $R^2$ and $R^3$ is a group represented by Chemical Formula 2,

[Chemical Formula 2]

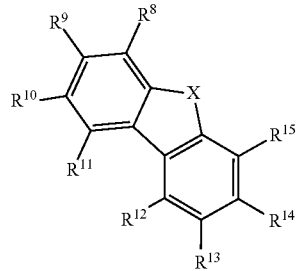

wherein, in Chemical Formula 2,

X is O, S, $SO_2$, $CR^aR^b$, $SiR^cR^d$, or $NR^e$, and adjacent two of $R^8$ to $R^{15}$ are linked to each other to provide a ring represented by one of Chemical Formulae 2-A to 2-C,

[Chemical Formula 2-A]

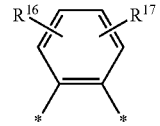

[Chemical Formula 2-B]

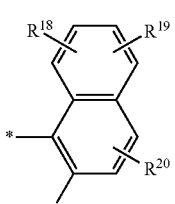

[Chemical Formula 2-C]

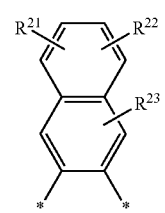

wherein, in Chemical Formulae 2-A to 2-C,

* is a linking point, $R^8$ to $R^{15}$ not providing a ring, $R^{16}$ to $R^{23}$, and $R^a$ to $R^e$ are independently hydrogen, deuterium, a substituted or unsubstituted C1 to C30 alkyl group, a substituted or unsubstituted C3 to C30 cycloalkyl group, a substituted or unsubstituted C2 to C30 heterocyclic group, a substituted or unsubstituted C6 to C30 aryl group, a substituted or unsubstituted C6 to C30 arylamine group, a halogen, a cyano group, a hydroxyl group, an amino group, a nitro group, or a combination thereof, or are a linking point with $L^2$ or $L^3$ of Chemical Formula 1.

According to another embodiment, an organic optoelectronic device includes an anode and a cathode facing each other, at least one organic layer between the anode and the cathode, wherein the organic layer includes the organic compound.

According to yet another embodiment, a display device including the organic optoelectronic device is provided.

Advantageous Effects

An organic optoelectronic device having high efficiency and long life-span may be realized.

DESCRIPTION OF DRAWINGS

FIG. 1 is a cross-sectional view of an organic light emitting diode according to an embodiment, and FIG. 2 is a cross-sectional view of an organic light emitting diode according to another embodiment.

BEST MODE

Hereinafter, embodiments of the present invention are described in detail. However, these embodiments are exemplary, the present invention is not limited thereto and the present invention is defined by the scope of claims.

In the present specification, when a definition is not otherwise provided, the term "substituted" refers to one substituted with deuterium, a halogen, hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 aryl group, a C2 to C30 heterocyclic group, a C1 to C20 alkoxy group, a C1 to C10 trifluoroalkyl group such as a trifluoromethyl group, or a cyano group, instead of at least one hydrogen of a substituent or a compound.

In addition, two adjacent substituents of the substituted halogen, hydroxy group, an amino group, a substituted or unsubstituted C1 to C20 amine group, a nitro group, a substituted or unsubstituted C3 to C40 silyl group, C1 to C30 alkyl group, C1 to C10 alkylsilyl group, C6 to C30 aryl group, C3 to C30 heterocyclic group, C1 to C20 alkoxy group, a C1 to C10 trifluoroalkyl group such as a trifluoromethyl group, and the like, or cyano group may be fused to form a ring. For example, the substituted C6 to C30 aryl group may be fused with another adjacent substituted C6 to C30 aryl group to form a substituted or unsubstituted fluorene ring.

In the present specification, when specific definition is not otherwise provided, "hetero" refers to one including at least one hetero atom and remaining carbons in one functional group. The hetero atom may be selected from N, O, S, P, and Si.

In the present specification, "aryl group" refers to a group including at least one hydrocarbon aromatic moiety, and includes carbocyclic aromatic moieties linked by a single bond and carbocyclic aromatic moieties fused directly or indirectly to provide a non-aromatic fused ring. The aryl group may include a monocyclic, polycyclic or fused polycyclic (i.e., rings sharing adjacent pairs of carbon atoms) functional group.

In the present specification, "heterocyclic group" may refer to a cyclic compound such as an aryl group, a cycloalkyl group, a fused ring thereof, or a combination thereof including at least one hetero atom selected from N, O, S, P, and Si and remaining carbon. When the heterocyclic group is a fused ring, an entire ring or each ring of the heterocyclic group may include at least one hetero atom.

More specifically, a substituted or unsubstituted aryl group and/or a substituted or unsubstituted heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted terphenyl group, a substituted or unsubstituted quarterphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridinyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazole group, a combination thereof, or a fused ring of the combination thereof, but are not limited thereto.

In the specification, hole characteristics refer to an ability to donate an electron to form a hole when an electric field is applied and that a hole formed in the anode may be easily injected into the emission layer and transported in the emission layer due to conductive characteristics according to a highest occupied molecular orbital (HOMO) level.

In addition, electron characteristics refer to an ability to accept an electron when an electric field is applied and that electron formed in the cathode may be easily injected into the emission layer and transported in the emission layer due to conductive characteristics according to a lowest unoccupied molecular orbital (LUMO) level.

Hereinafter, an organic compound according to an embodiment is described.

An organic compound according to an embodiment is represented by Chemical Formula 1.

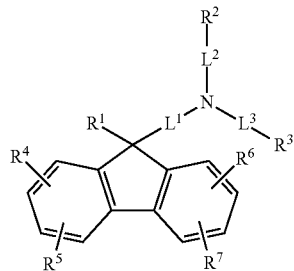

[Chemical Formula 1]

In Chemical Formula 1, $L^1$ to $L^3$ are independently a single bond, a substituted or unsubstituted C6 to C30 arylene group, a substituted or unsubstituted C2 to C30 heterocyclic group, or a combination thereof, $R^1$ to $R^7$ are independently hydrogen, deuterium, a substituted or unsubstituted C1 to C30 alkyl group, a substituted or unsubstituted C3 to C30 cycloalkyl group, a substituted or unsubstituted C2 to C30 heterocyclic group, a substituted or unsubstituted C6 to C30 aryl group, a halogen, a cyano group, a hydroxyl group, an amino group, a nitro group, or a combination thereof.

$R^4$ to $R^7$ of Chemical Formula 1 may independently be present or adjacent two are linked to each other to provide a ring.

At least one of $R^2$ and $R^3$ of Chemical Formula 1 may be a group represented by Chemical Formula 2.

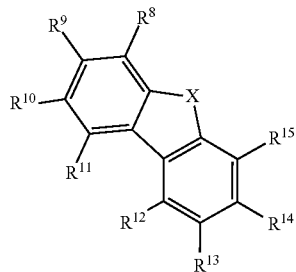

[Chemical Formula 2]

In Chemical Formula 2,
X is O, S, $SO_2$, $CR^aR^b$, $SiR^cR^d$, or $NR^e$, and
adjacent two of $R^8$ to $R^{15}$ are linked to each other to provide a ring represented by one of Chemical Formulae 2-A to 2-C,

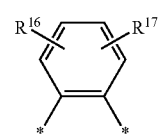

[Chemical Formula 2-A]

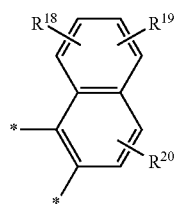

[Chemical Formula 2-B]

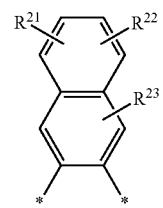

[Chemical Formula 2-C]

In Chemical Formulae 2-A to 2-C, * is a linking point.
In Chemical Formulae 2, and 2-A to 2-C, $R^8$ to $R^{15}$ not providing a ring, $R^{16}$ to $R^{23}$, and $R^a$ to $R^e$ are independently hydrogen, deuterium, a substituted or unsubstituted C1 to C30 alkyl group, a substituted or unsubstituted C3 to C30 cycloalkyl group, a substituted or unsubstituted C2 to C30 heterocyclic group, a substituted or unsubstituted C6 to C30 aryl group, a substituted or unsubstituted C6 to C30 arylamine group, a halogen, a cyano group, a hydroxyl group, an amino group, a nitro group, or a combination thereof, or a combination thereof or are a linking point with $L^2$ or $L^3$ of Chemical Formula 1.

The organic compound may have good hole characteristics by including an arylamine group substituted with a fused ring and bonded with a substituted or unsubstituted fluorene core directly or indirectly, and may control a T1 energy level due to a sp3 bond of fluorene, and may effectively applied as a light emitting material and/or hole transport material of fluoresence and phosphorescence devices.

For example, $L^1$ to $L^3$ may independently be a single bond or a substituted or unsubstituted C6 to C30 arylene group.

For example, L¹ to L³ may independently be a single bond or a substituted or unsubstituted phenylene group, a substituted or unsubstituted biphenylene group, a substituted or unsubstituted naphthylene group, or a combination thereof.

For example, L¹ to L³ may independently be a single bond, a substituted or unsubstituted m-phenylene group, or a substituted or unsubstituted p-phenylene group.

For example, X may be O or S. When X is O or S, since the organic compound is stable for electrons, the organic compound may be stable for attack of electrons injected from a cathode when being used as a hole transport material.

For example, R¹ may be hydrogen, a substituted or unsubstituted C1 to C30 alkyl group, a substituted or unsubstituted C6 to C30 aryl group, a substituted or unsubstituted C2 to C30 heterocyclic group, or a combination thereof.

For example, R¹ may be a substituted or unsubstituted C6 to C30 aryl group.

For example, R¹ may be a substituted or unsubstituted phenyl group, a substituted or unsubstituted biphenyl group, a substituted or unsubstituted terphenyl group, a substituted or unsubstituted quarterphenyl group, a substituted or unsubstituted naphthyl group, a substituted or unsubstituted anthracenyl group, a substituted or unsubstituted phenanthryl group, or a combination thereof.

For example, R² and R³ may independently be hydrogen, a substituted or unsubstituted C1 to C30 alkyl group, a substituted or unsubstituted C6 to C30 aryl group, a substituted or unsubstituted C2 to C30 heterocyclic group, or a combination thereof, and one of R² and R³ may be a group represented by Chemical Formula 2.

For example, one of R² and R³ may be a group represented by Chemical Formula 2 and the other may be a substituted or unsubstituted C6 to C30 aryl group.

For example, one of R² and R³ may be a group represented by Chemical Formula 2 and the other may be a substituted or unsubstituted phenyl group, a substituted or unsubstituted biphenyl group, a substituted or unsubstituted terphenyl group, a substituted or unsubstituted quarterphenyl group, a substituted or unsubstituted naphthyl group, a substituted or unsubstituted anthracenyl group, a substituted or unsubstituted phenanthryl group, or a combination thereof.

For example, R² may be a group represented by Chemical Formula 2 and R¹ and R³ may independently be a substituted or unsubstituted phenyl group, a substituted or unsubstituted biphenyl group, a substituted or unsubstituted terphenyl group, a substituted or unsubstituted quarterphenyl group, a substituted or unsubstituted naphthyl group, a substituted or unsubstituted anthracenyl group, a substituted or unsubstituted phenanthryl group, or a combination thereof.

For example, in Chemical Formulae 2, and 2-A to 2-C R⁸ to R¹⁵ not providing a ring, R¹⁶ to R²³, and Rᵃ to Rᵉ are independently hydrogen, deuterium, a substituted or unsubstituted C1 to C30 alkyl group, a substituted or unsubstituted C2 to C30 heterocyclic group, a substituted or unsubstituted C6 to C30 aryl group, or are a linking point with L² or L³ of Chemical Formula 1.

For example, Chemical Formula 2 may be one of substituted or unsubstituted groups listed in Group 1.

[Group 1]

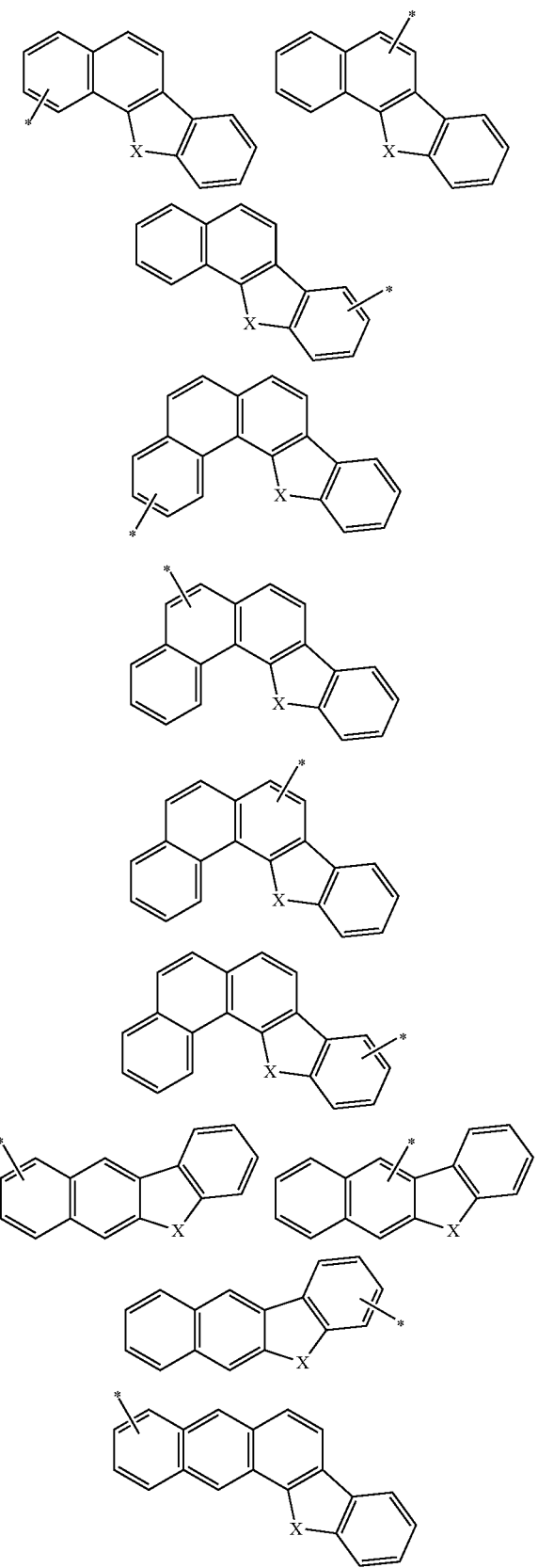

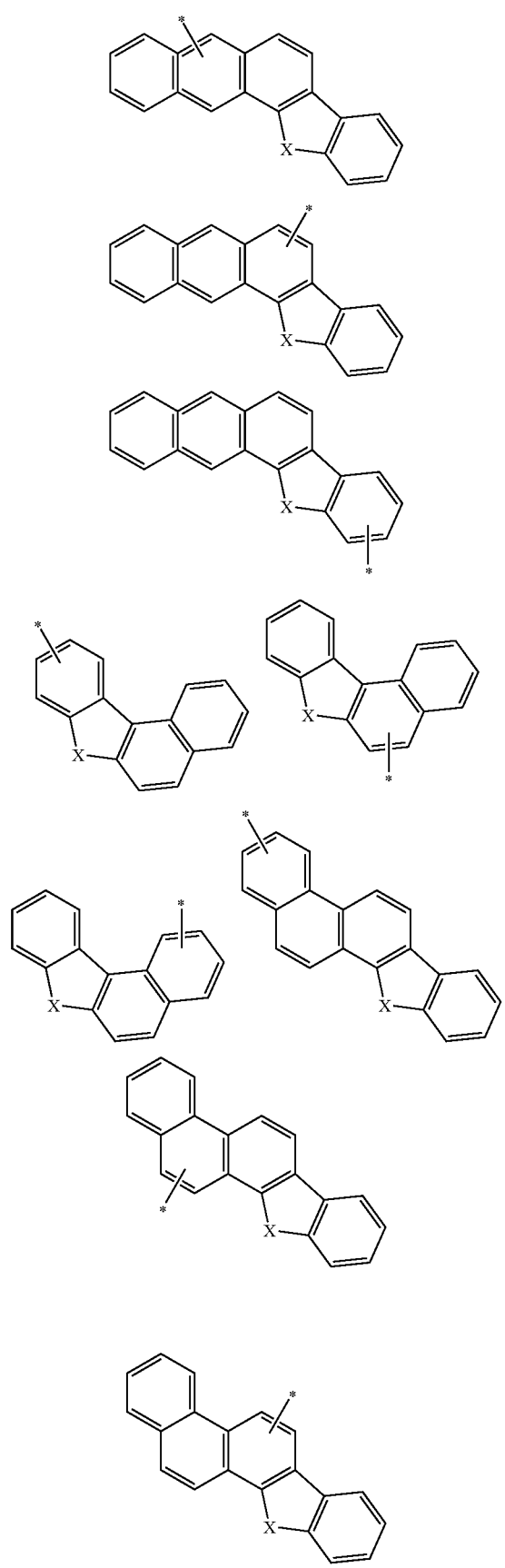
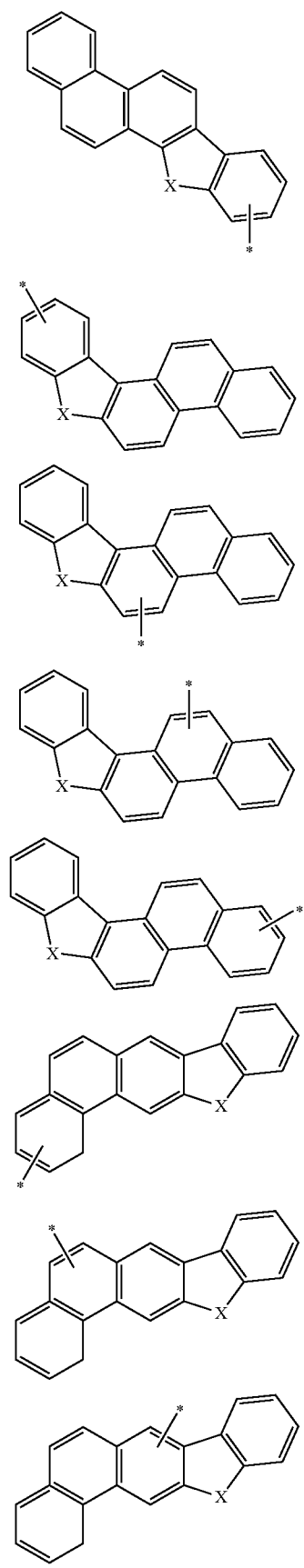

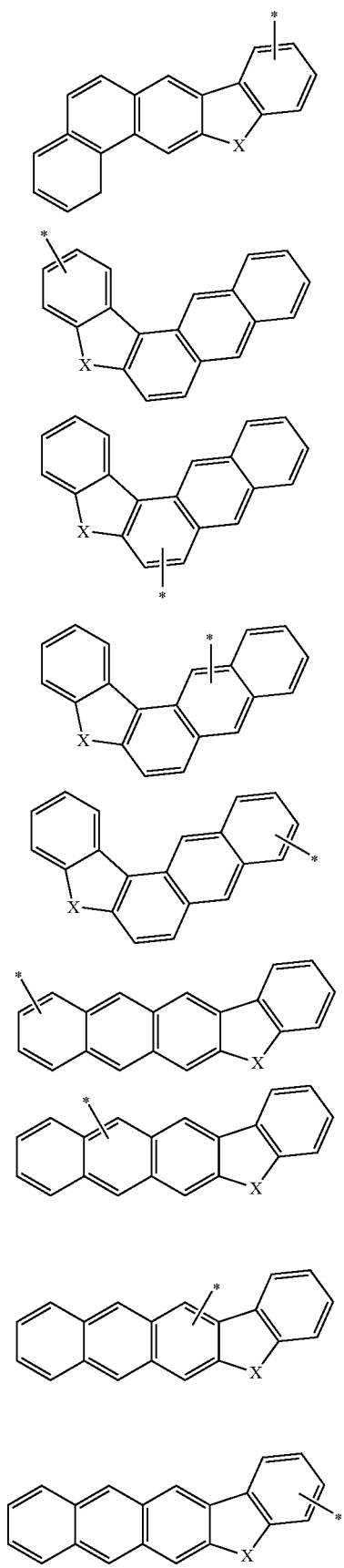
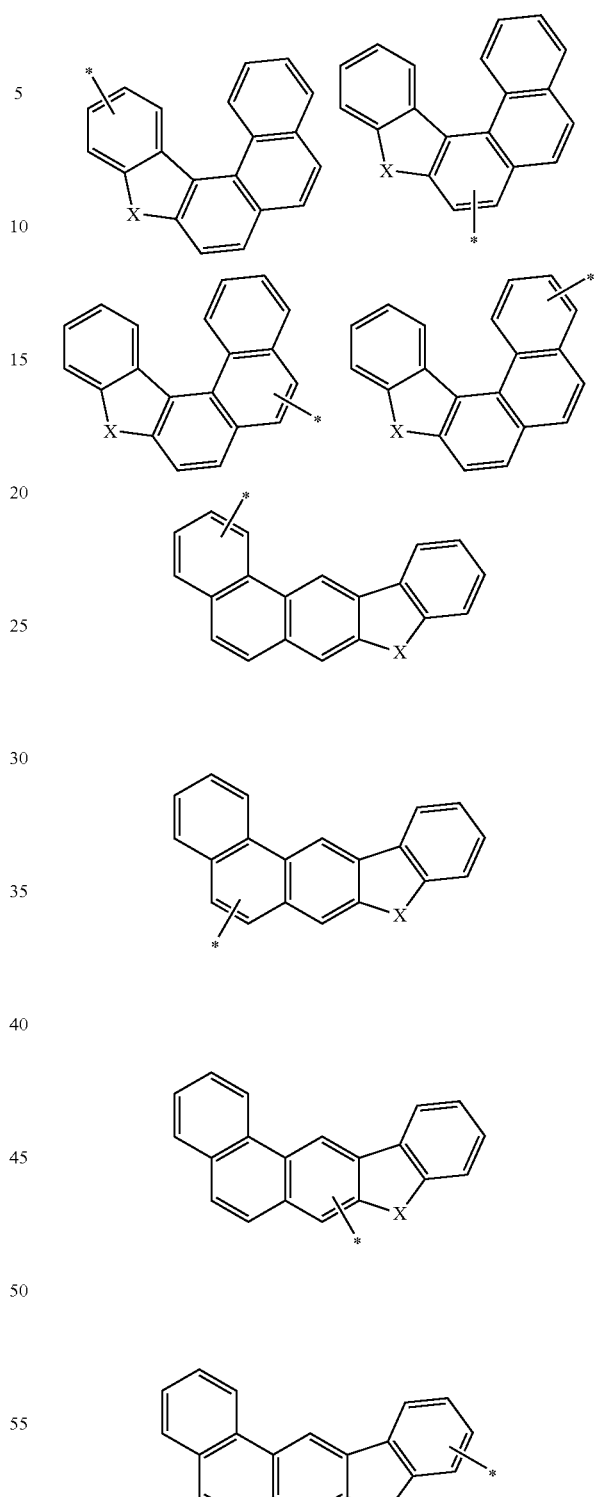
In Group 1, * is a linking point and X is the same as described above.
In Group 1, substituents are not indicated, but the groups may be substituted or unsubstituted.
The organic compound may be, for example one of compounds listed in Group 2, but is not limited thereto.

[Group 2]
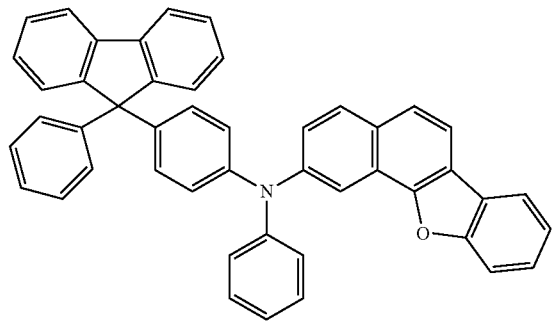
[A-1]
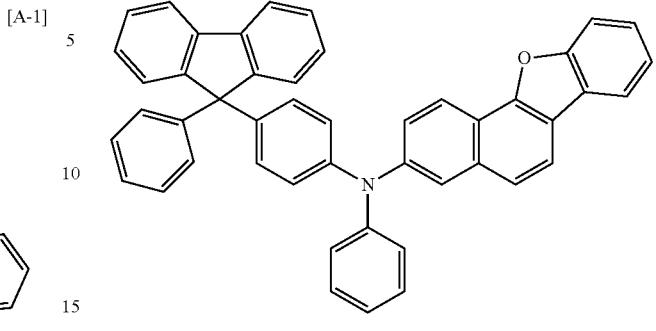
[A-5]
[A-2]
[A-6]
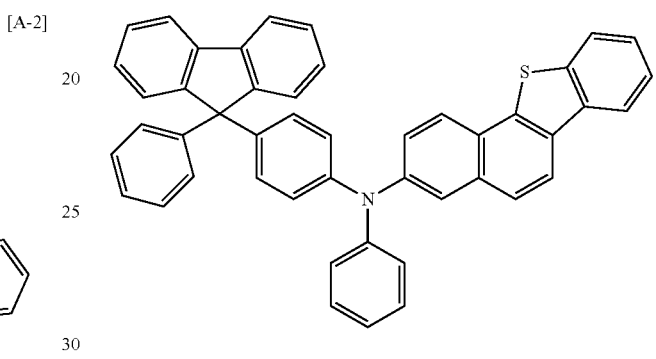
[A-3]
[A-7]
[A-4]
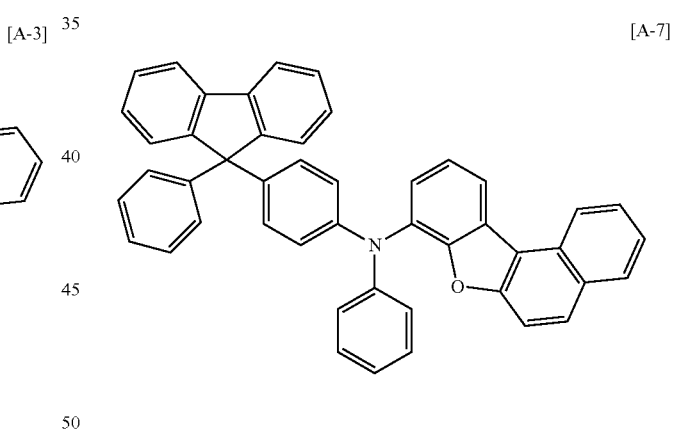
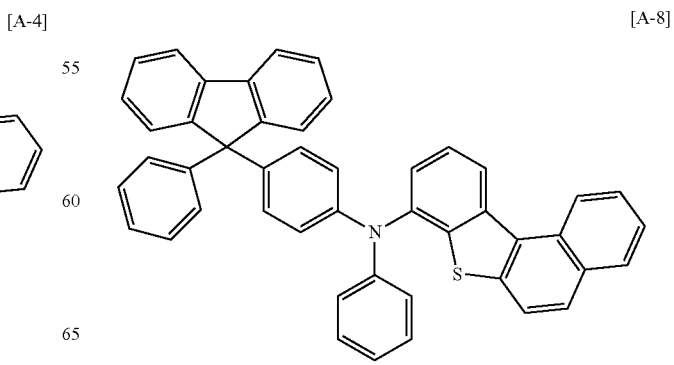
[A-8]

[A-9]
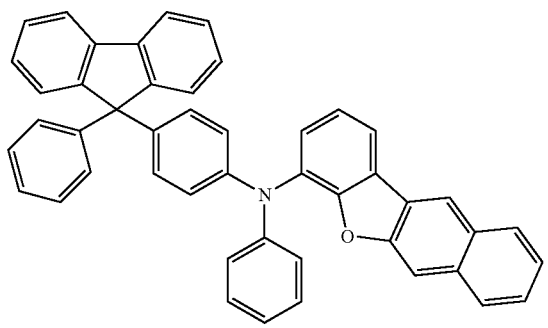
[A-10]
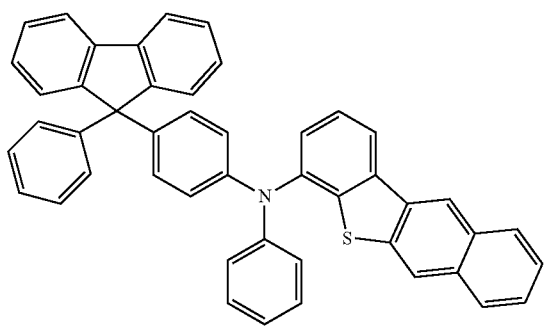
[A-11]
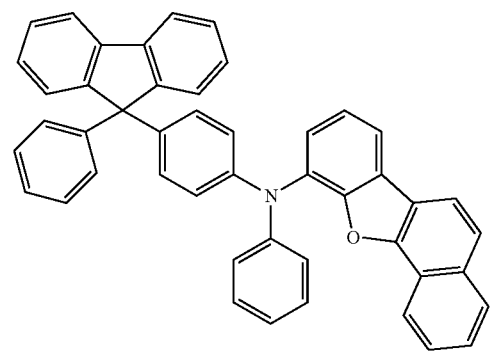
[A-12]
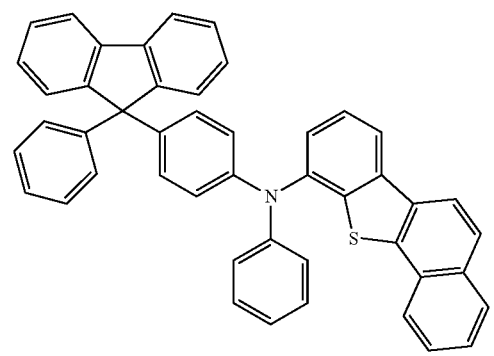
[A-13]
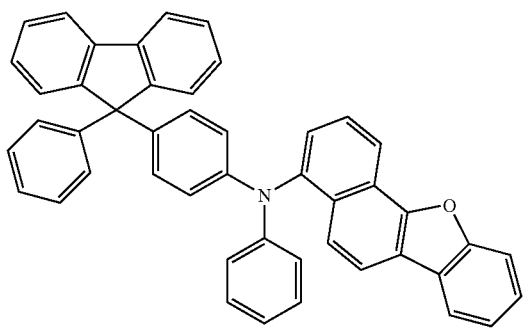
[A-14]
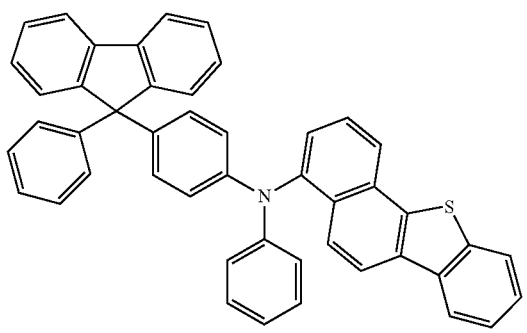
[A-15]
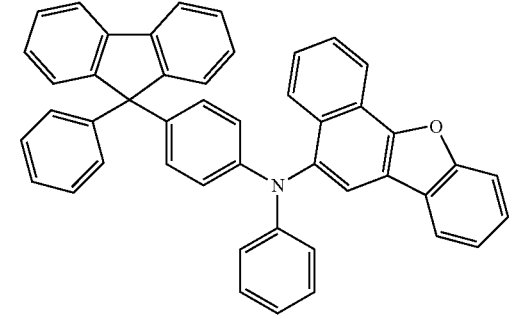
[A-16]
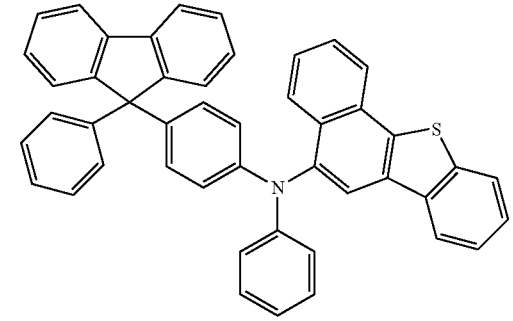

[A-17]
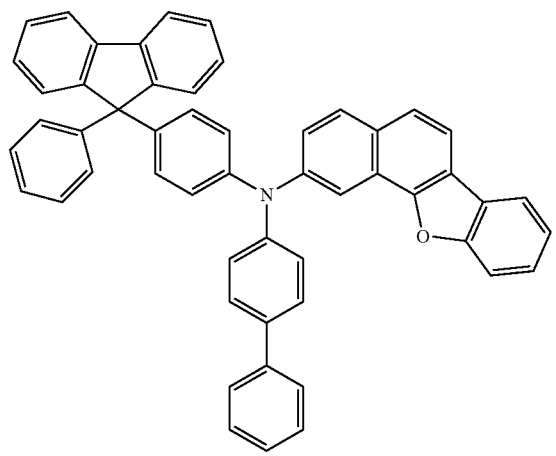
[A-20]
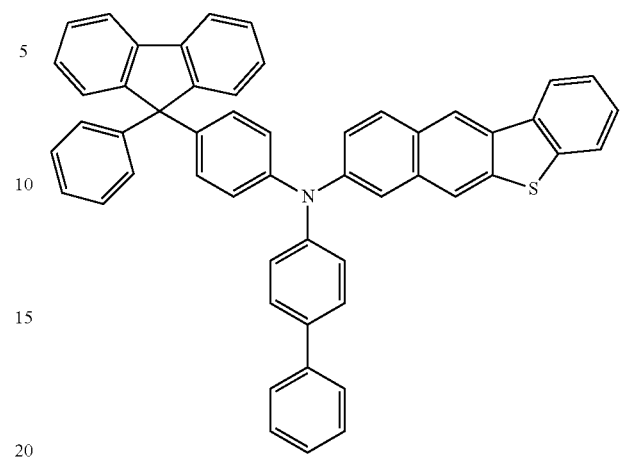
[A-18]
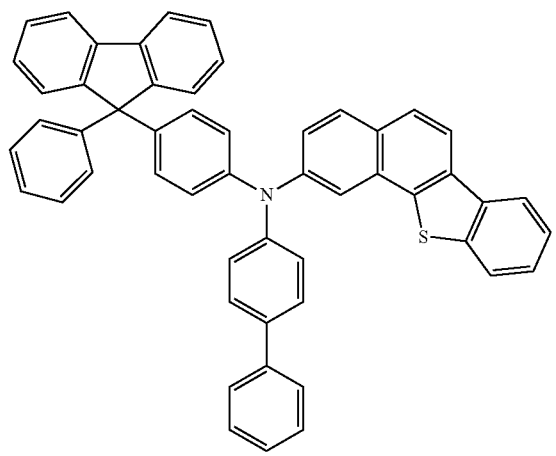
[A-21]
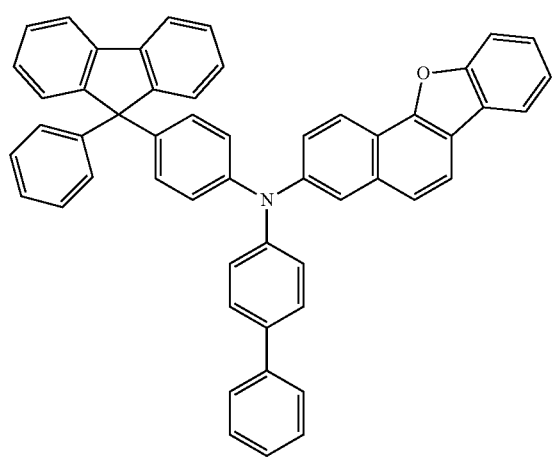
[A-19]
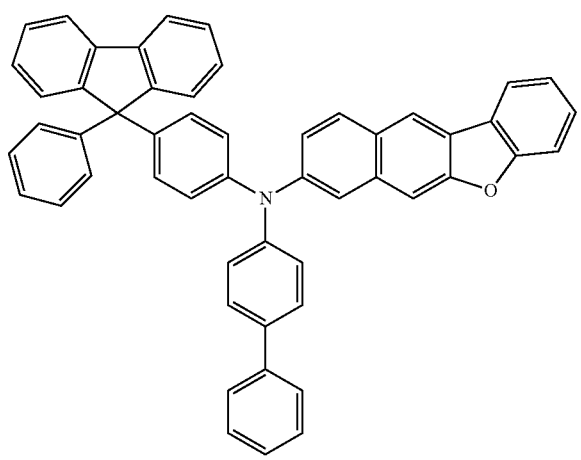
[A-22]
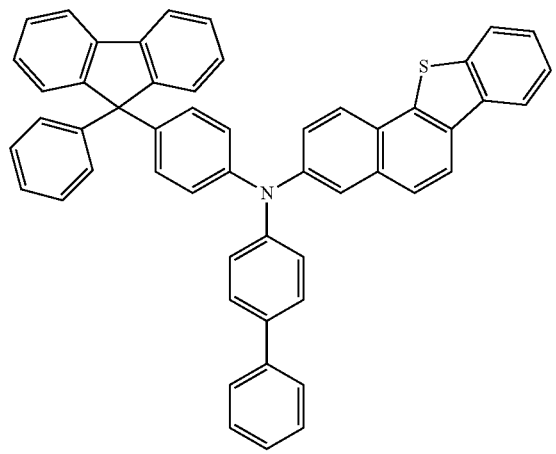

[A-23]
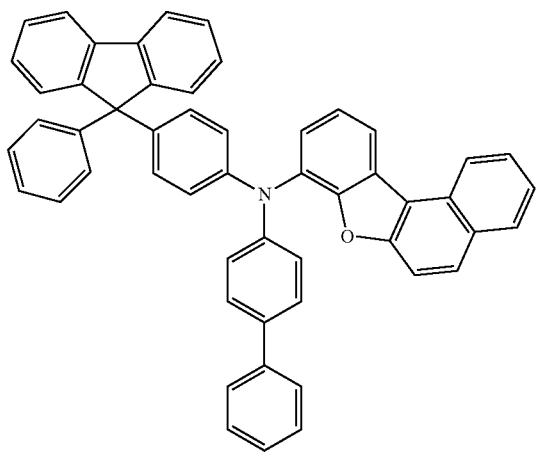
[A-26]
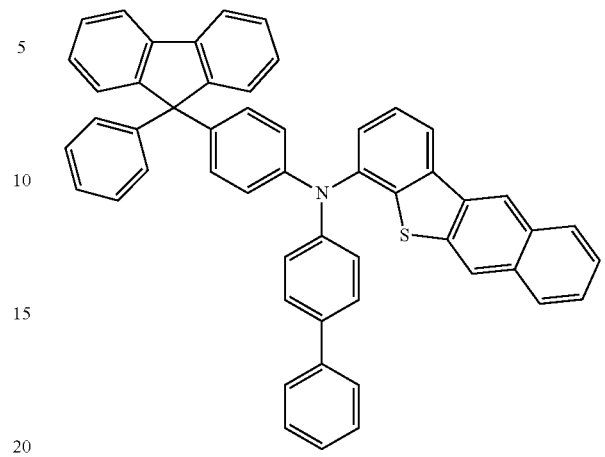
[A-24]
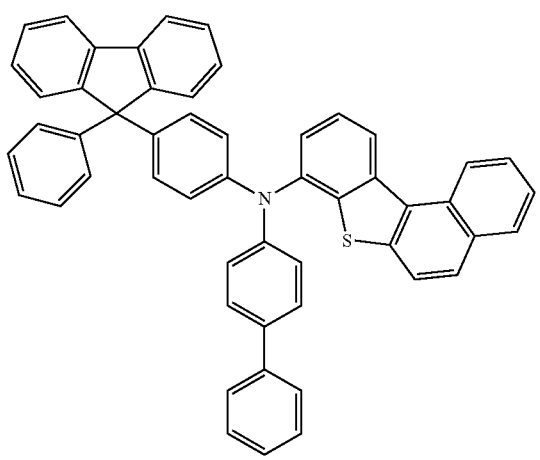
[A-27]
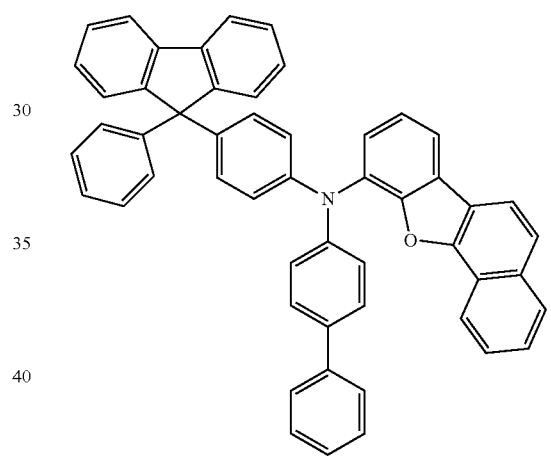
[A-25]
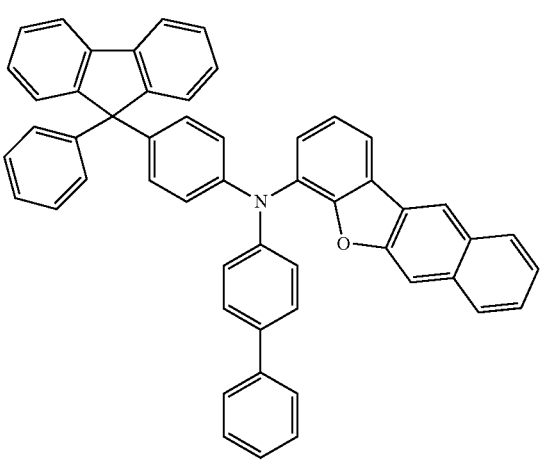
[A-28]
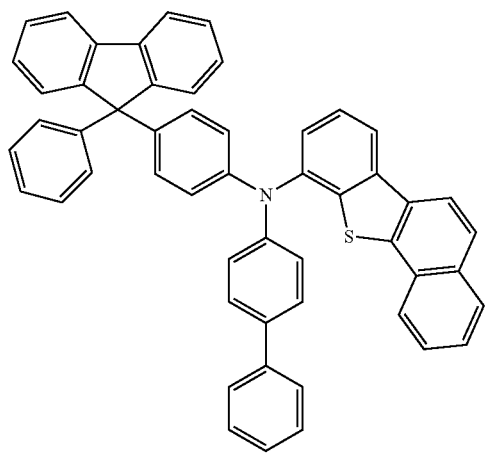

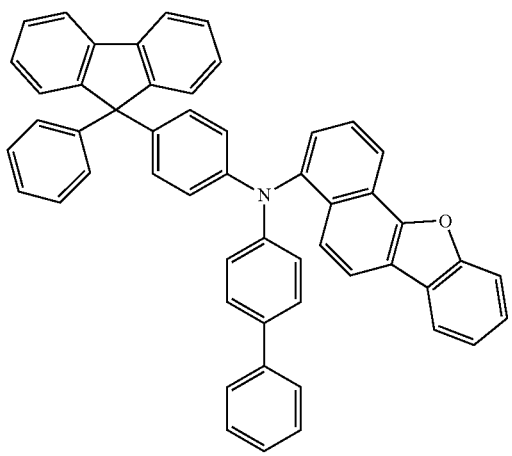
[A-29]
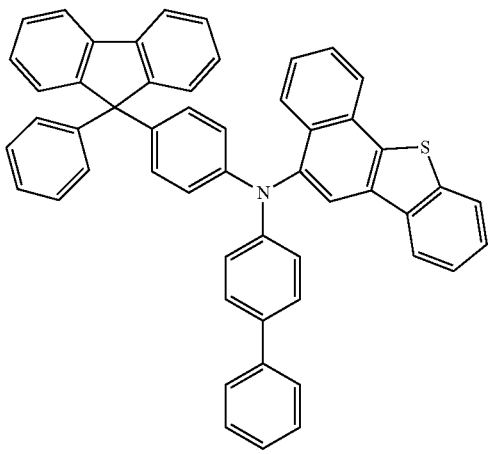
[A-32]
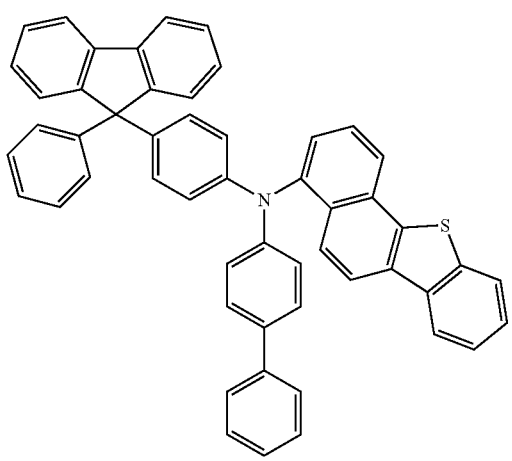
[A-30]
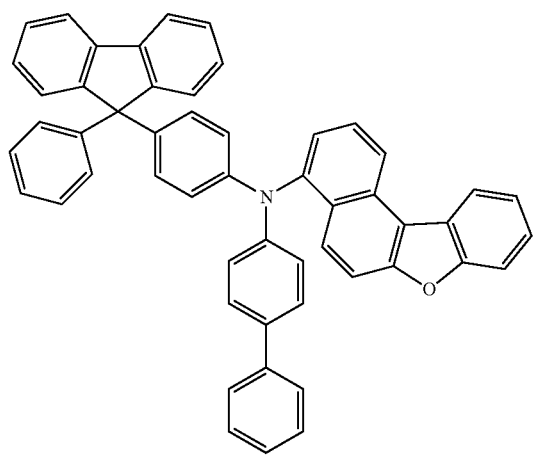
[A-33]
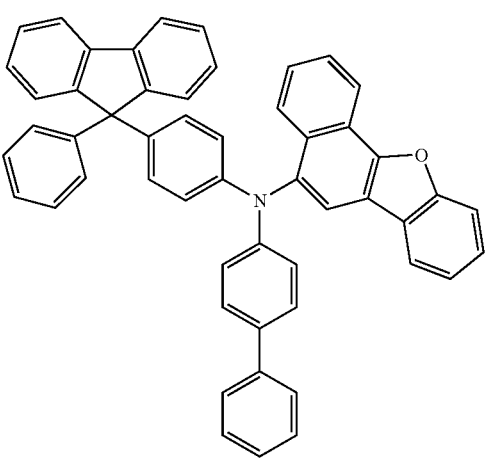
[A-31]

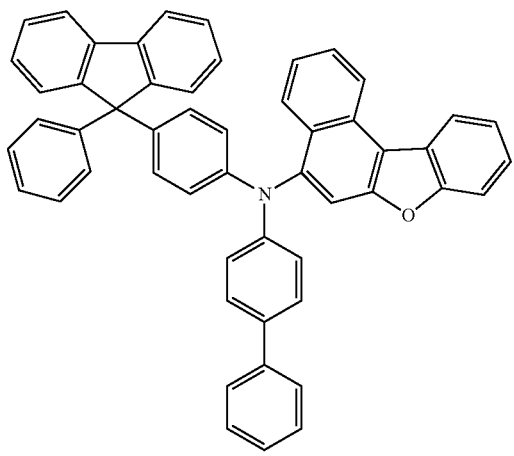
[A-35]
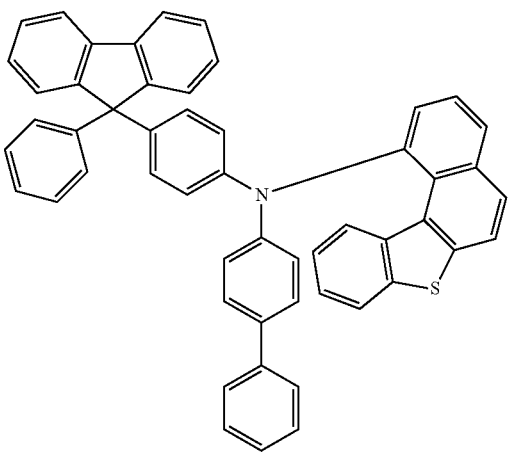
[A-38]
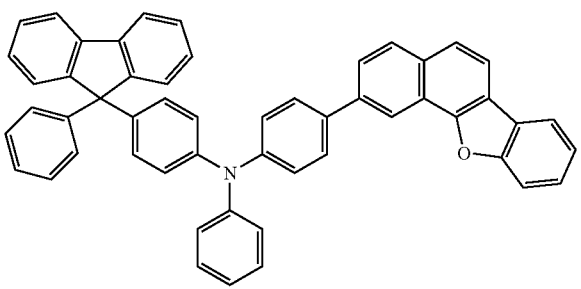
[A-39]
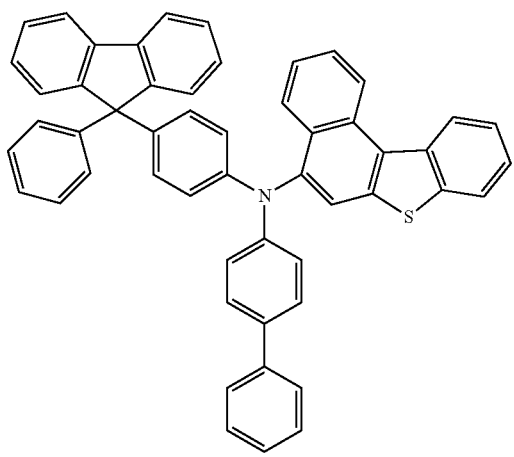
[A-36]
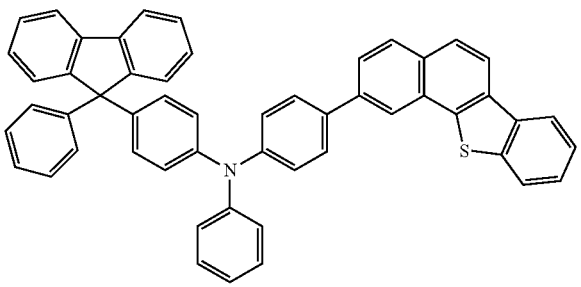
[A-40]
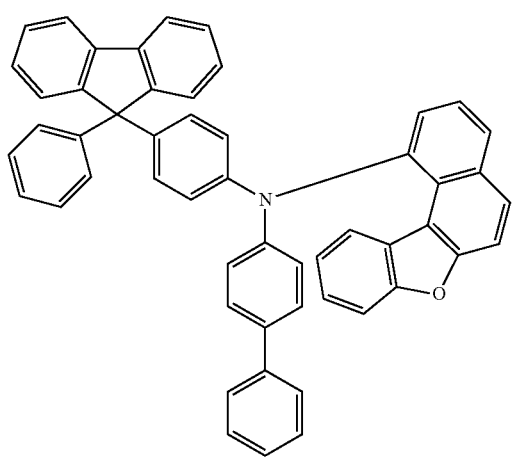
[A-37]
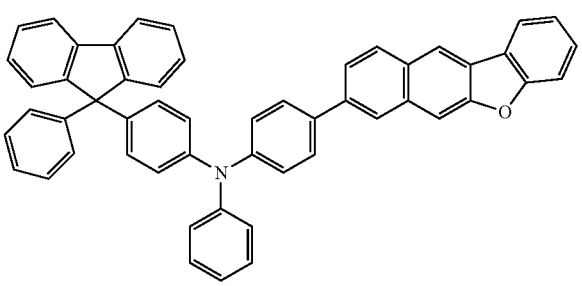
[A-41]

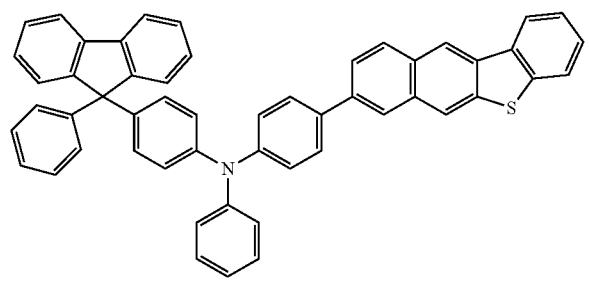
[A-42]
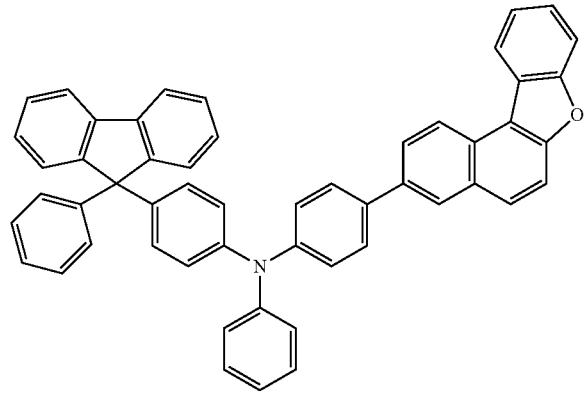
[A-43]
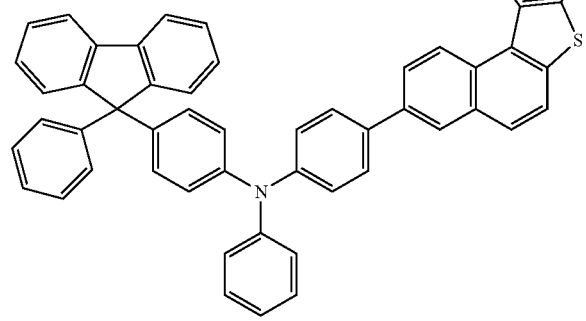
[A-44]
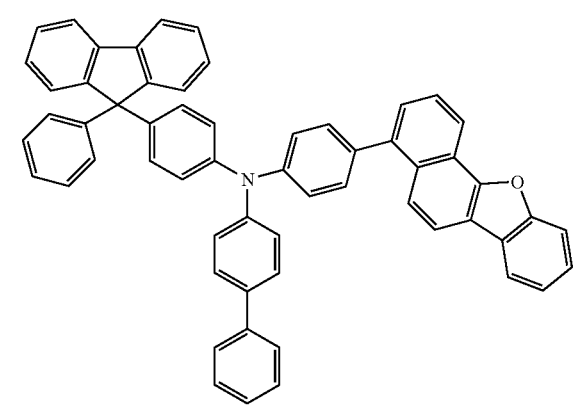
[A-45]
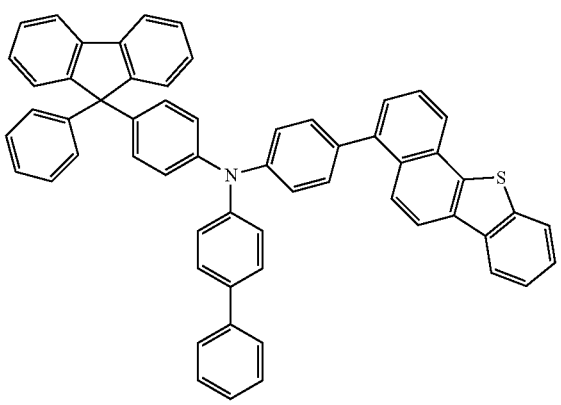
[A-46]
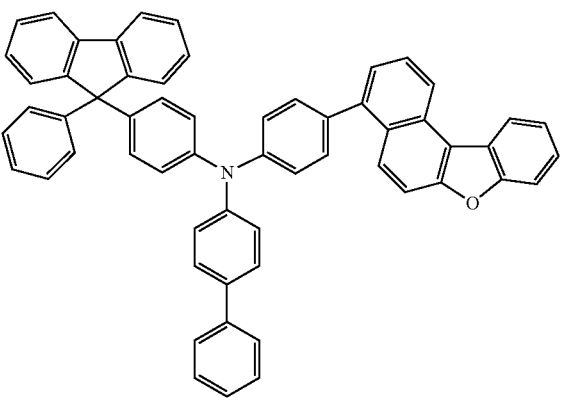
[A-47]
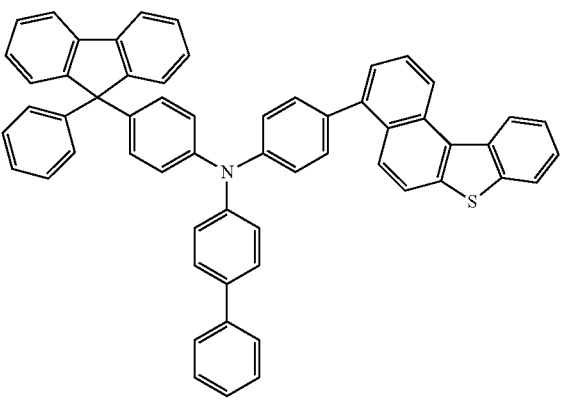
[A-48]

[A-49]
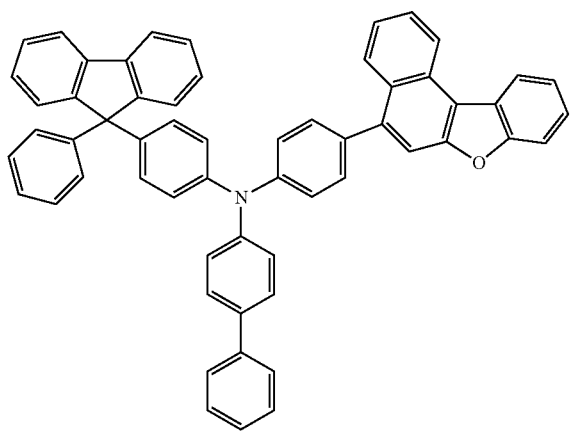
[A-52]
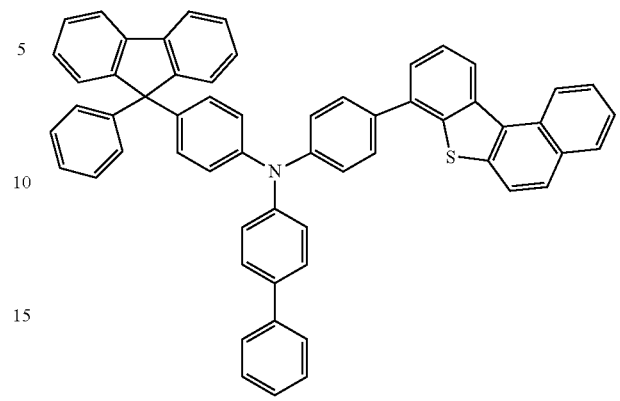
[A-50]
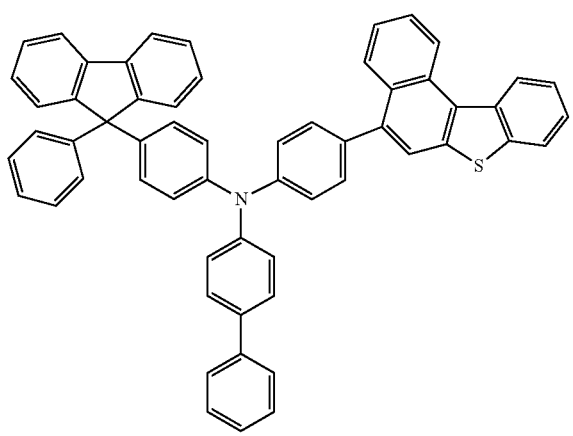
[A-53]
[A-51]
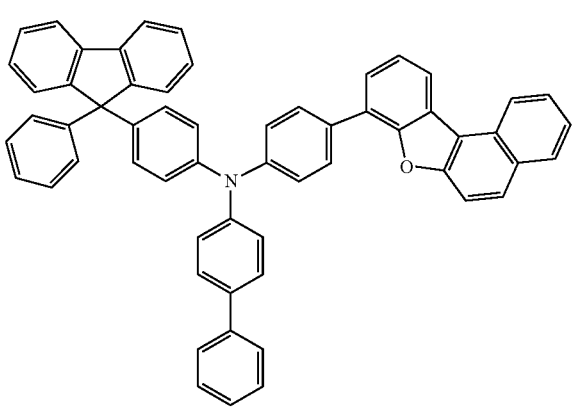
[A-54]
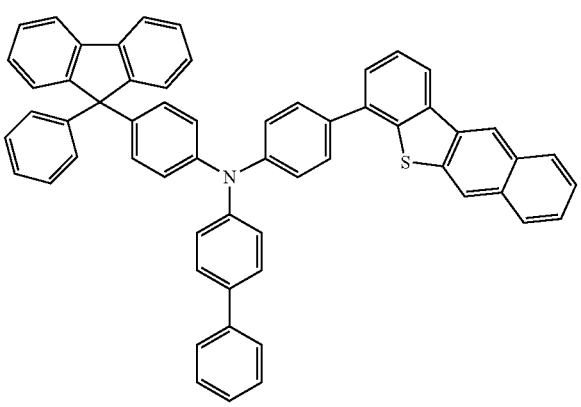

[A-55]
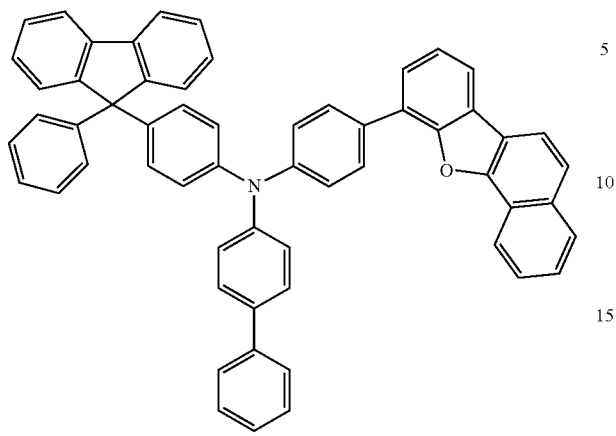
[A-56]
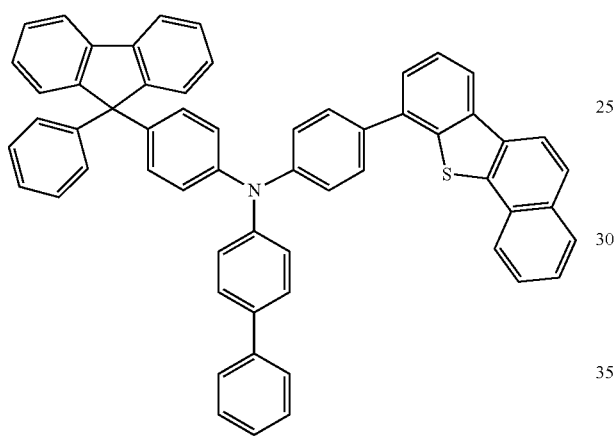
[A-57]
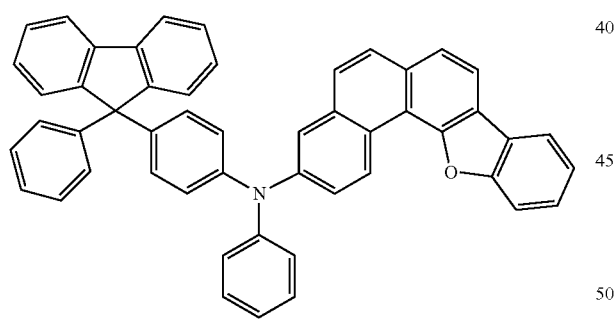
[A-58]
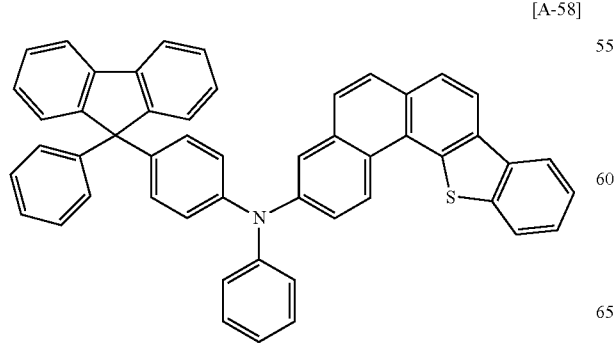
[A-59]
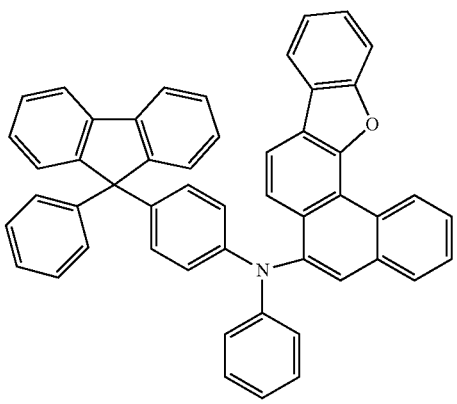
[A-60]
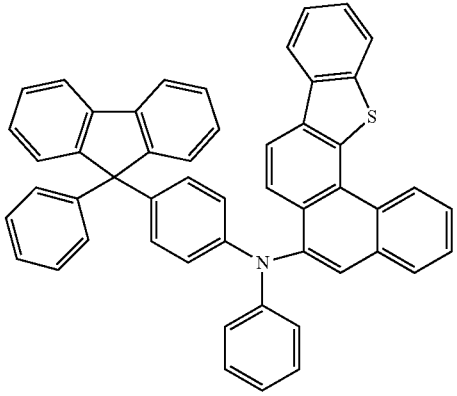
[A-61]
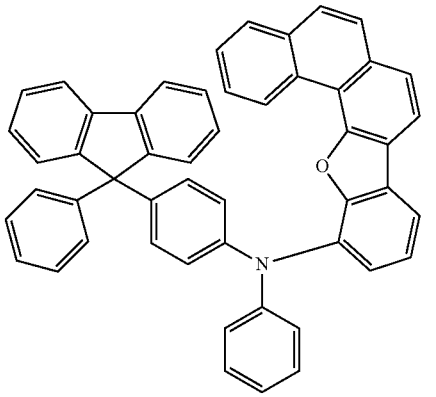
[A-62]
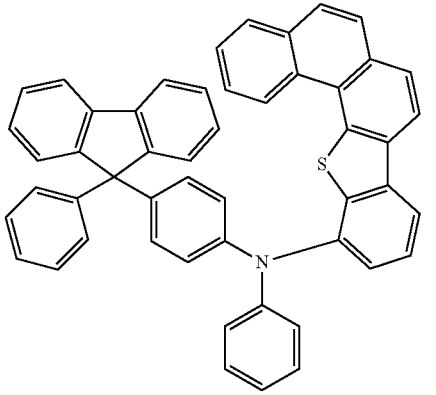

[A-63]
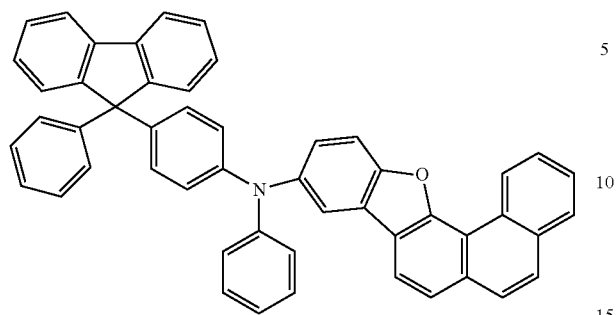
[A-64]
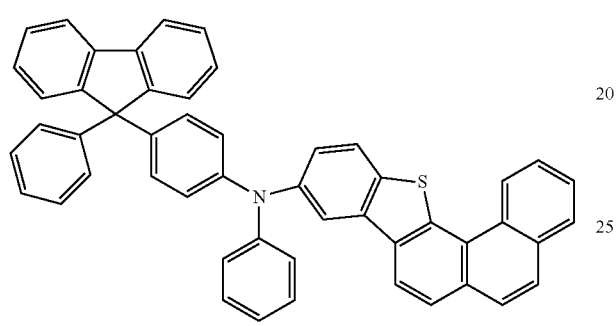
[A-65]
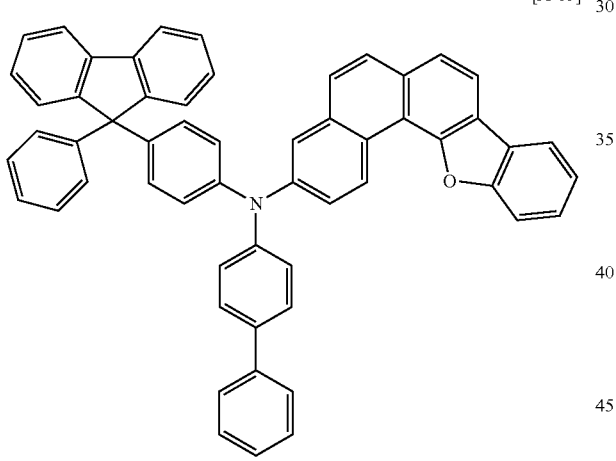
[A-66]
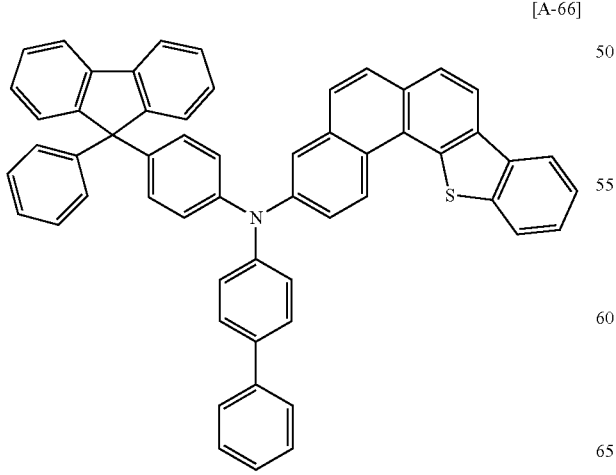
[A-67]
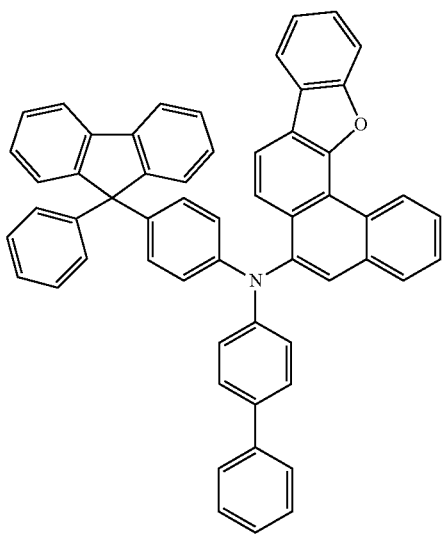
[A-68]
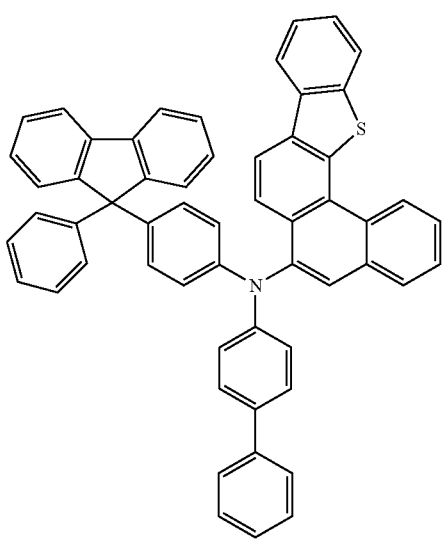
[A-69]
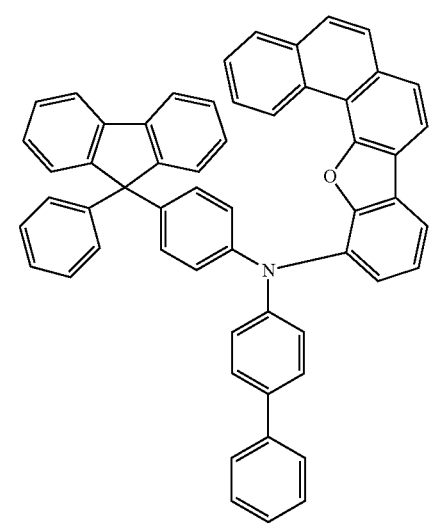

[A-70]
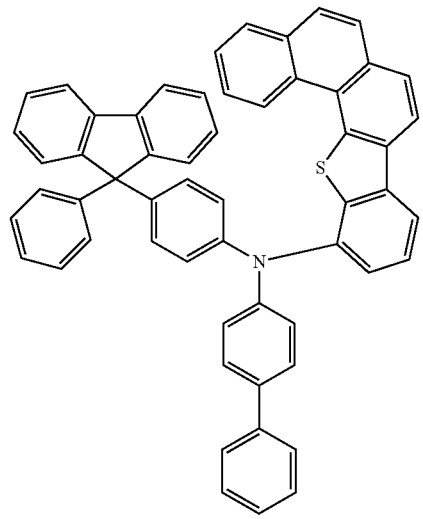
[A-72]
[A-73]
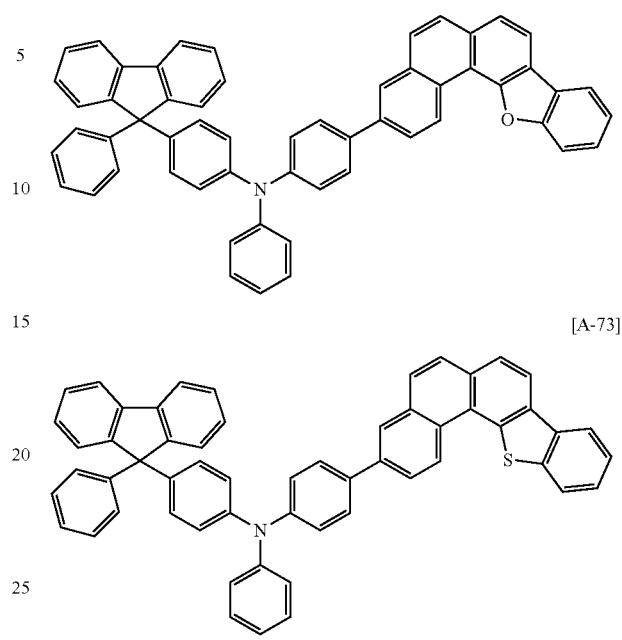
[A-71A]
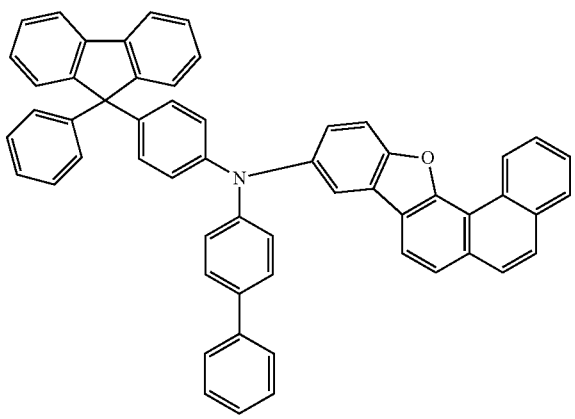
[A-74]
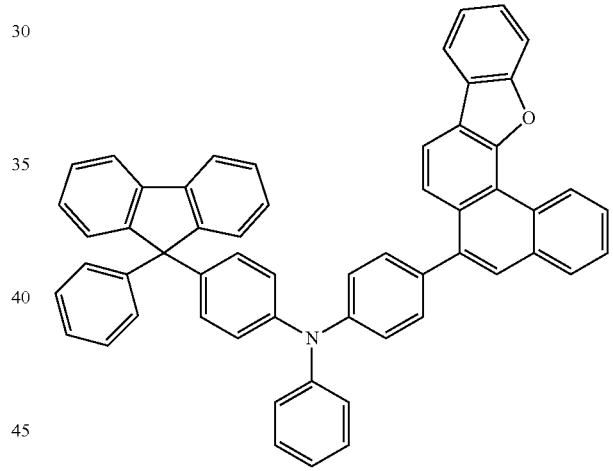
[A-71B]
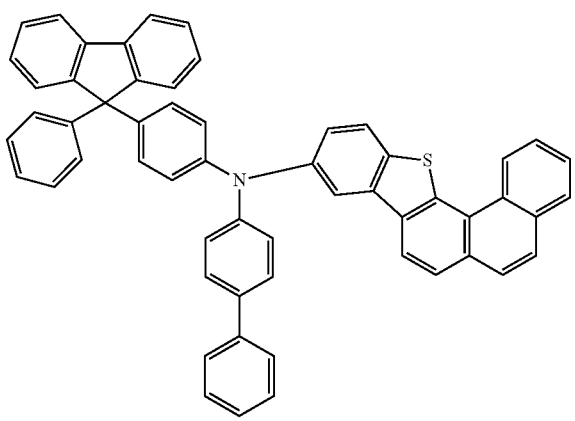
[A-75]
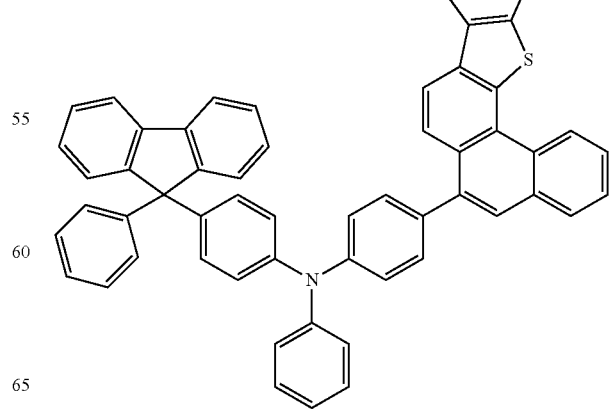

[A-76]
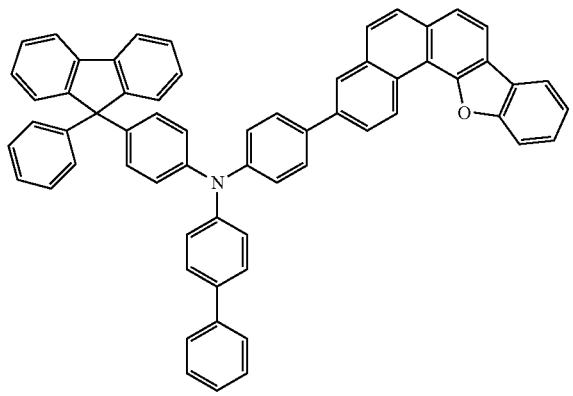
[A-77]
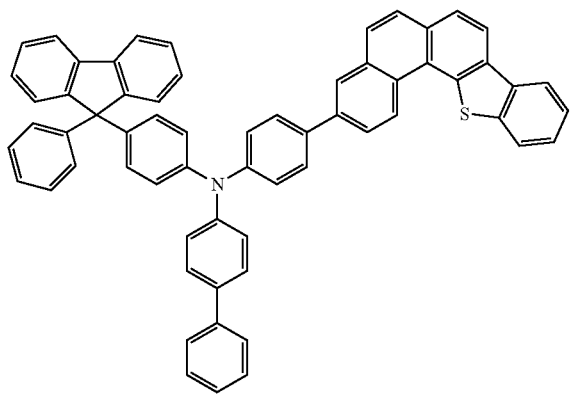
[A-78]
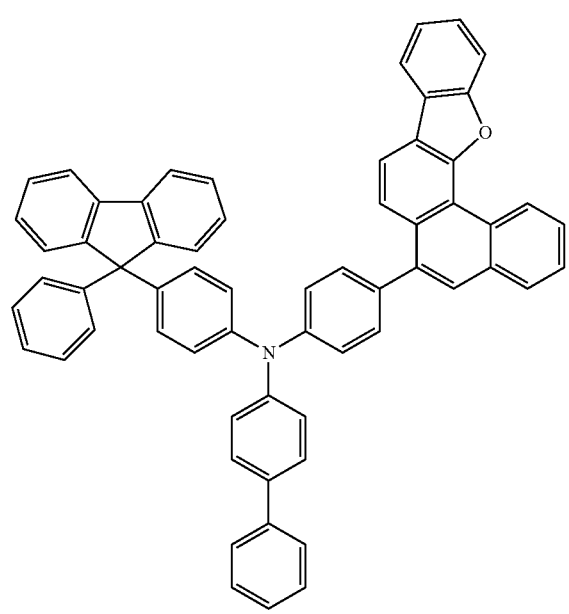
[A-79]
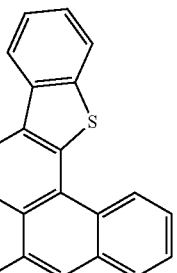
[A-80]
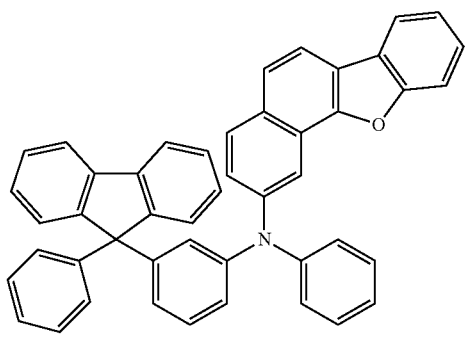
[A-81]
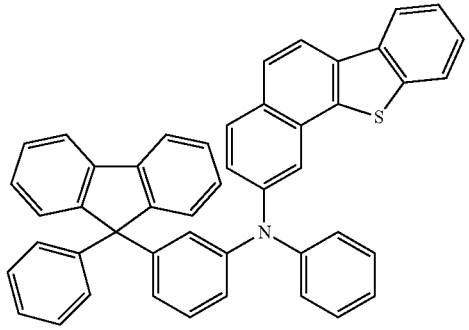

-continued
[A-82]
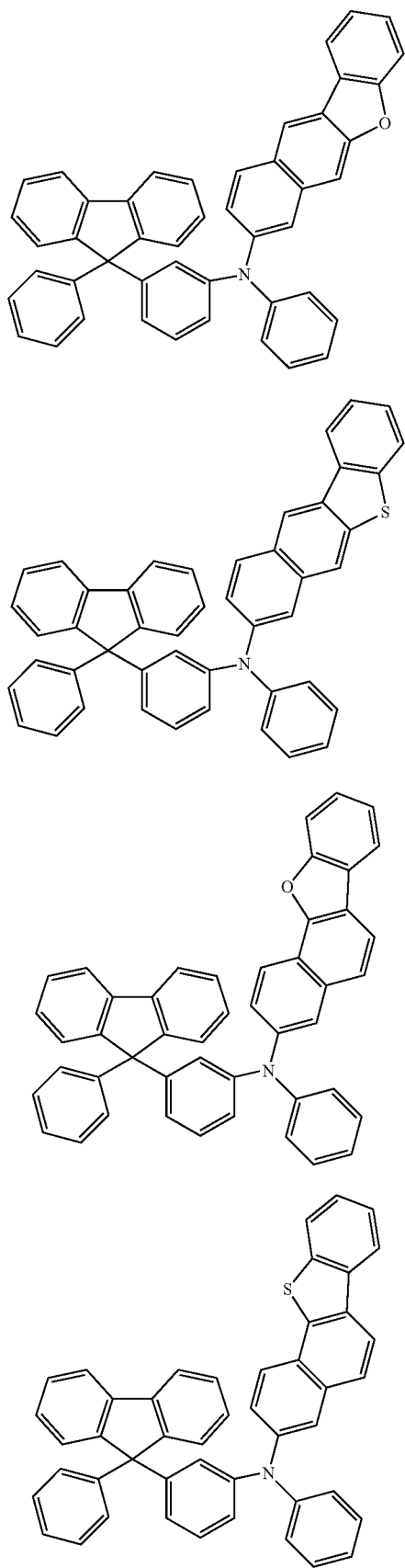
[A-83]
[A-84]
[A-85]
-continued
[A-86]
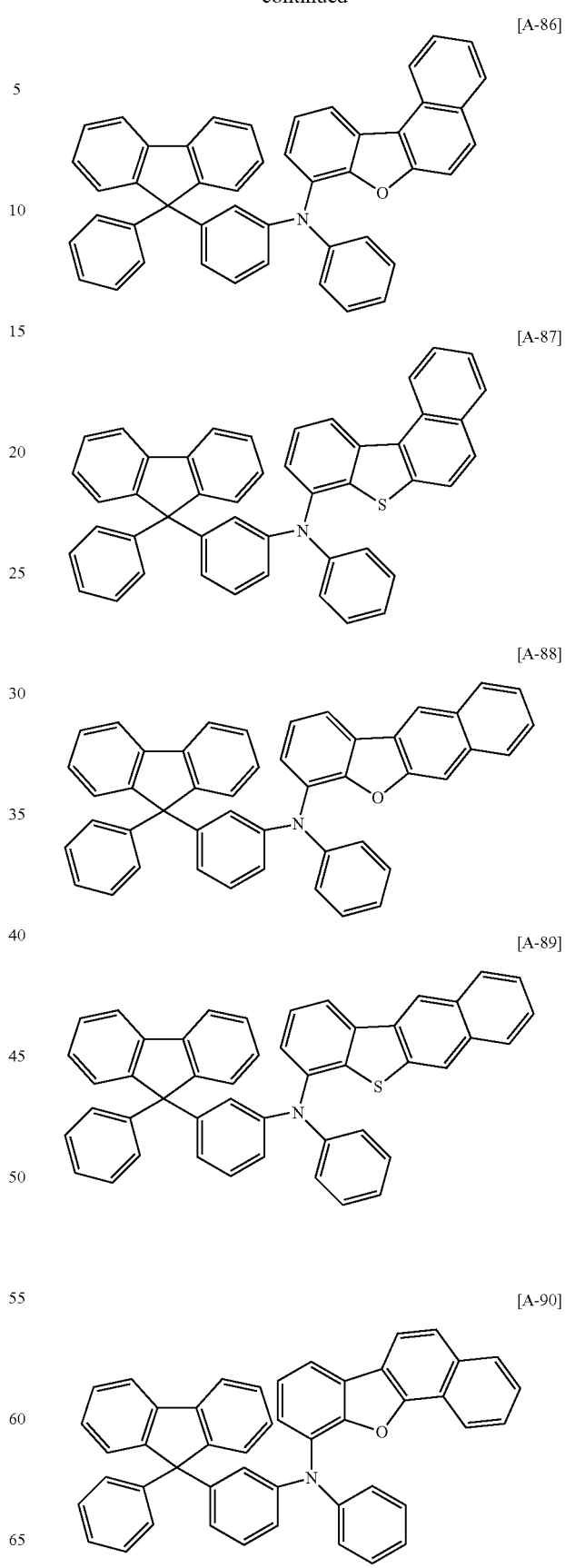
[A-87]
[A-88]
[A-89]
[A-90]

[A-91] 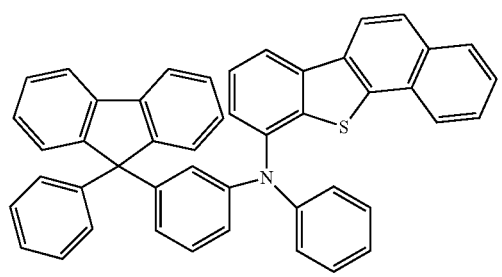
[A-92] 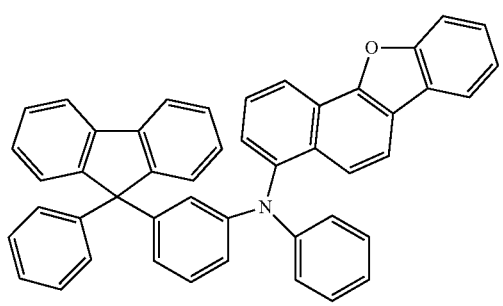
[A-93] 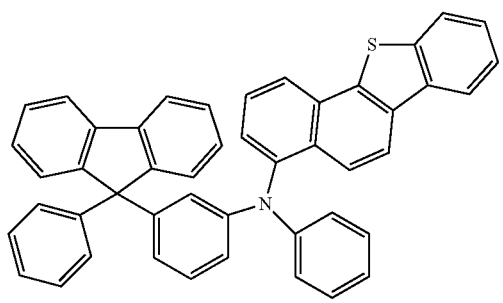
[A-94] 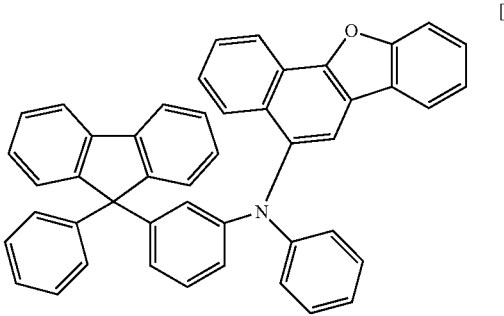
[A-95] 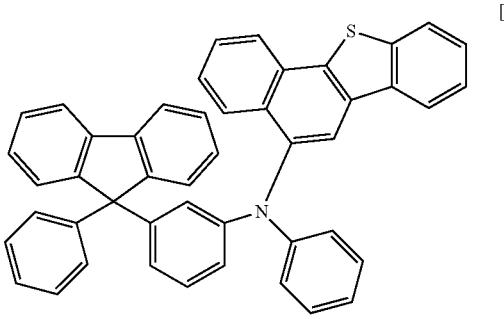
[A-96] 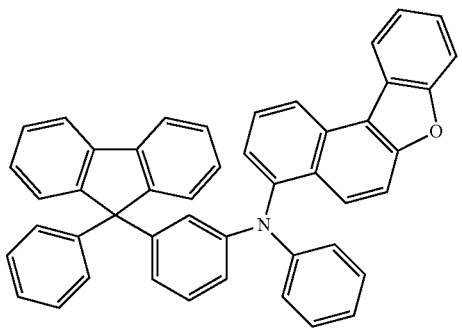
[A-97] 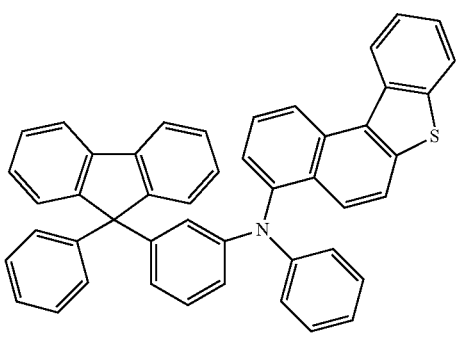
[A-98] 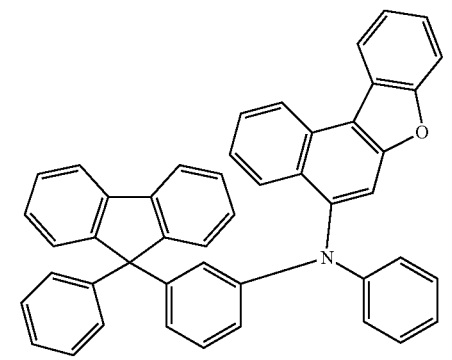
[A-99] 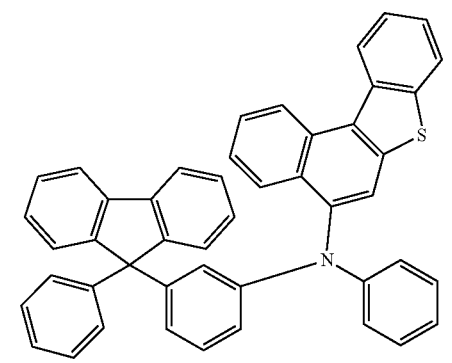

[A-100]
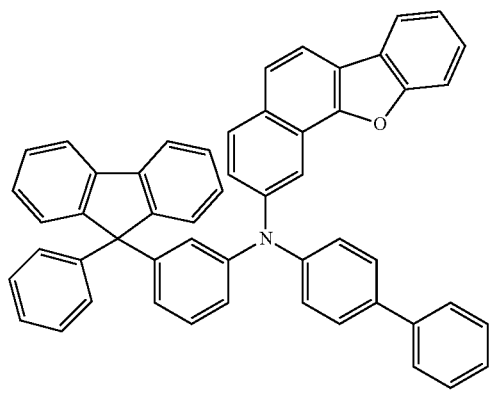
[A-101]
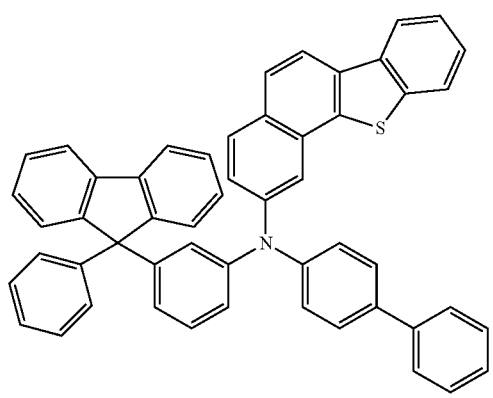
[A-102]
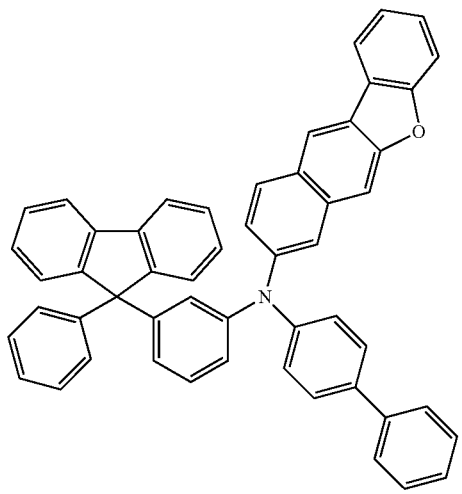
[A-103]
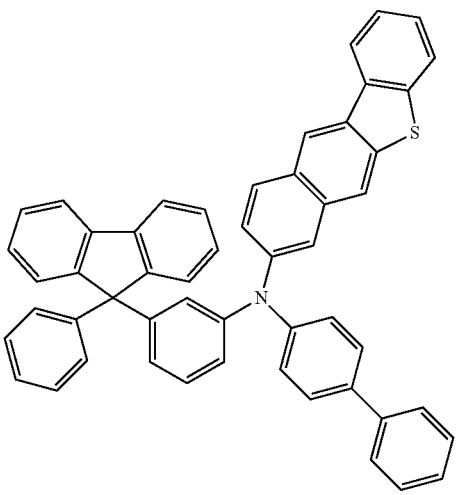
[A-104]
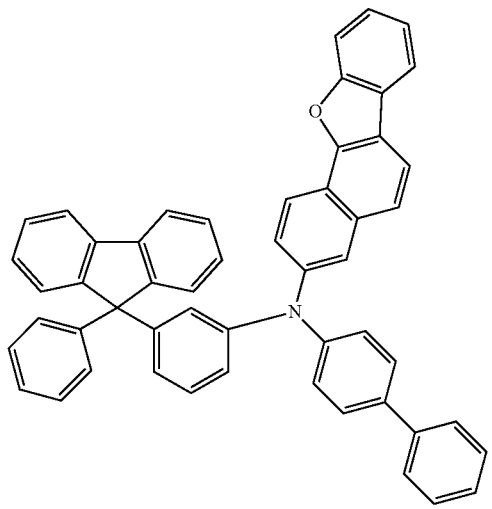
[A-105]
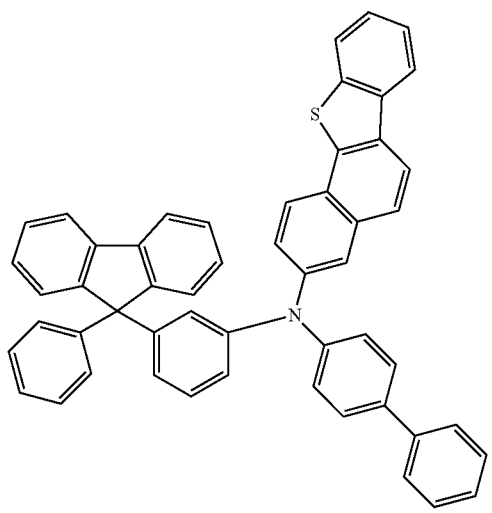

[A-106]
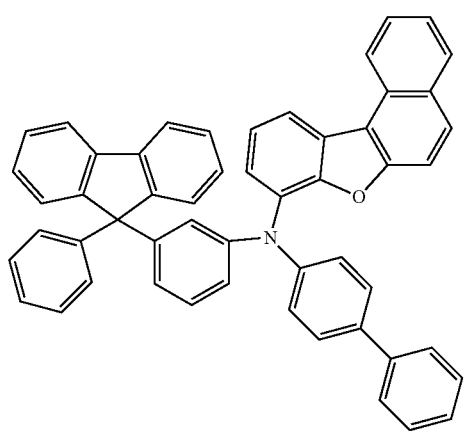
[A-107]
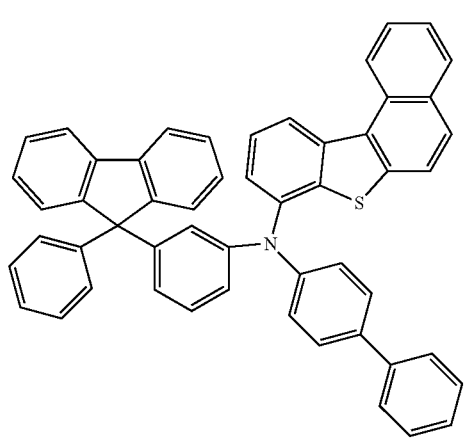
[A-108]
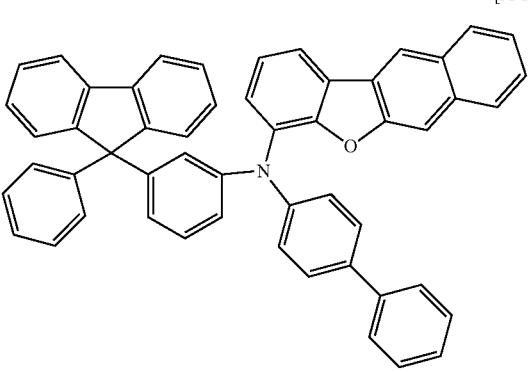
[A-109]
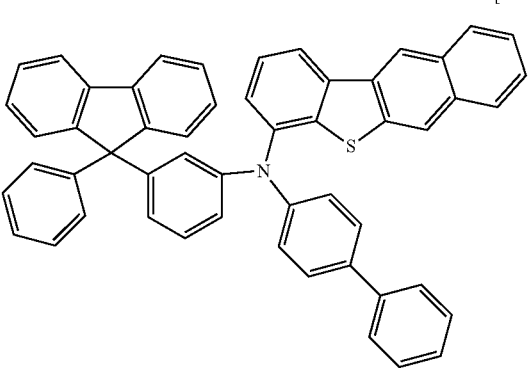
[A-110]
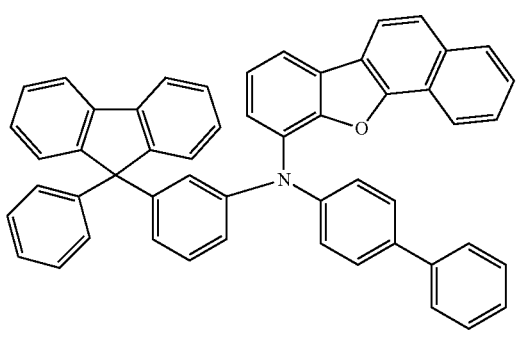
[A-111]
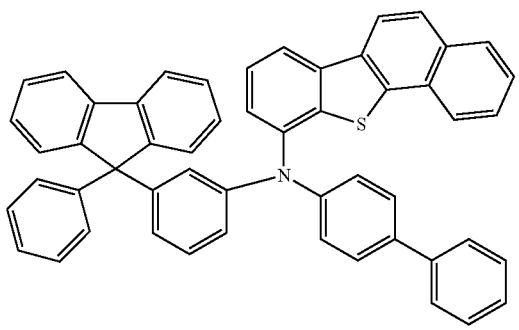
[A-112]
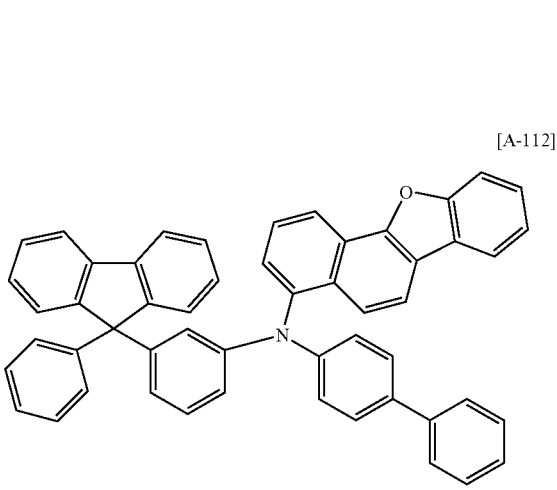
[A-113]
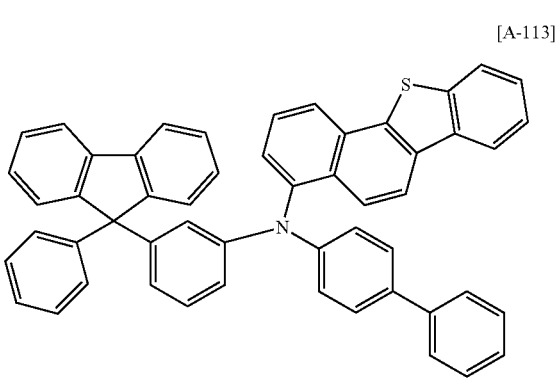

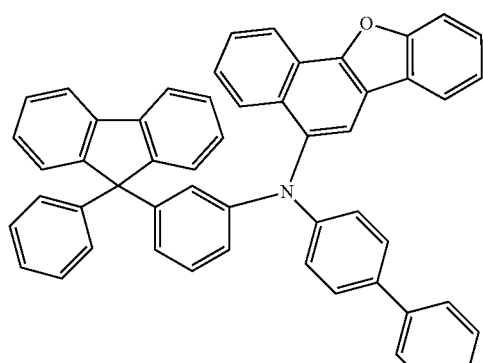
[A-114]
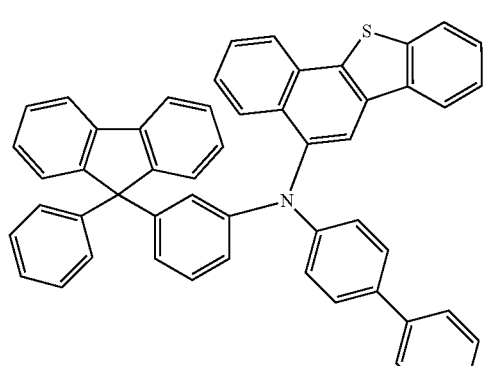
[A-115]
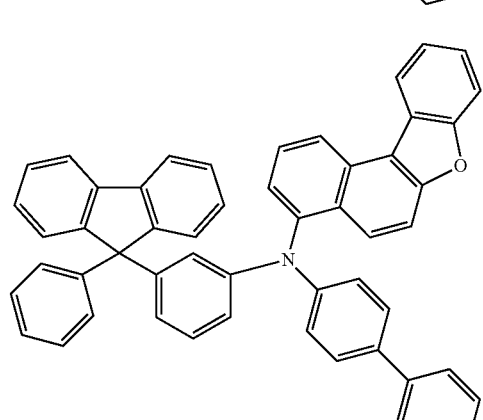
[A-116]
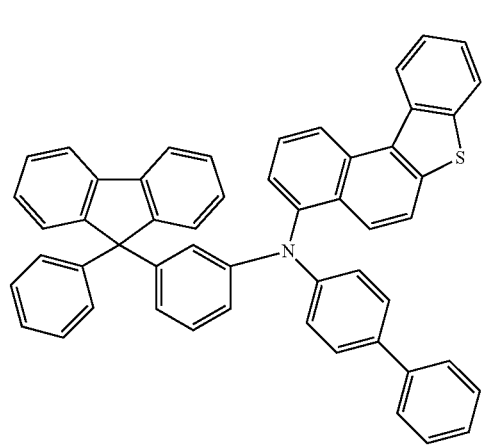
[A-117]
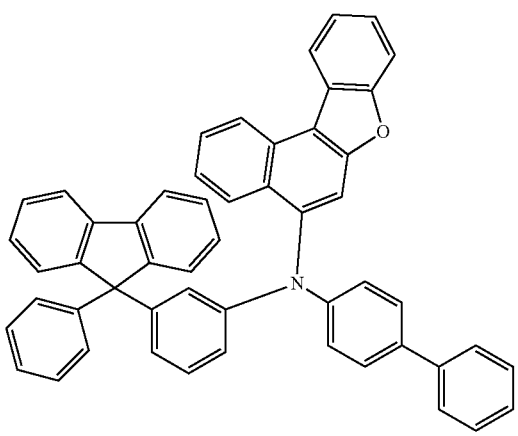
[A-118]
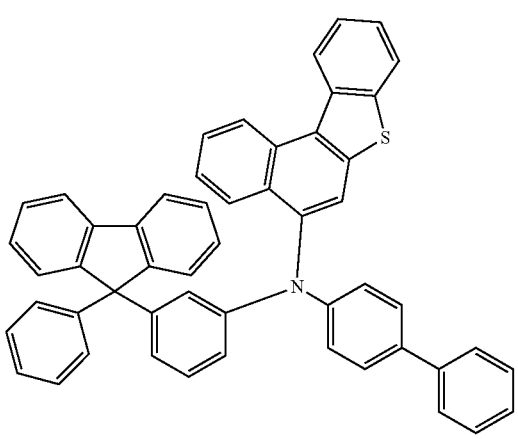
[A-119]
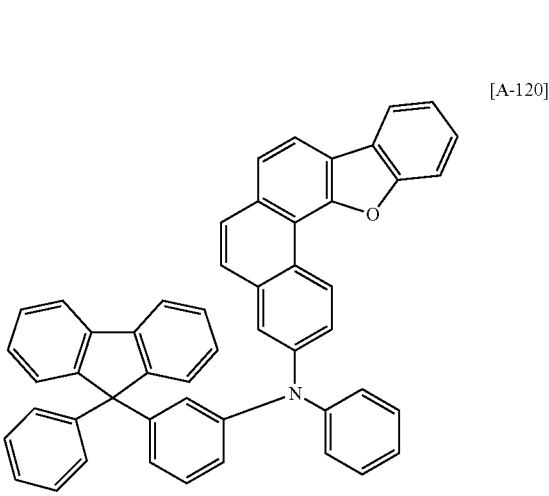
[A-120]

[A-121]
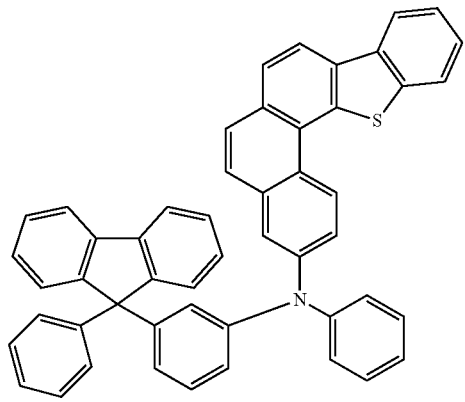
[A-125]
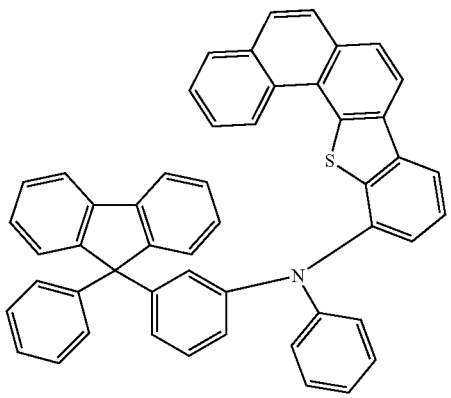
[A-122]
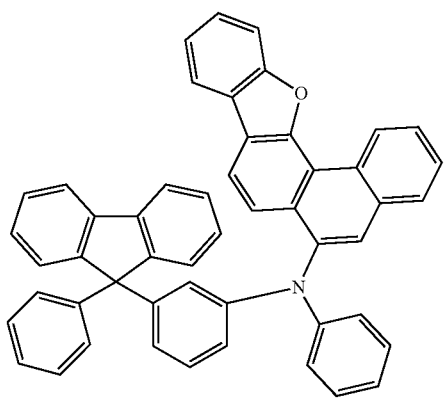
[A-126]
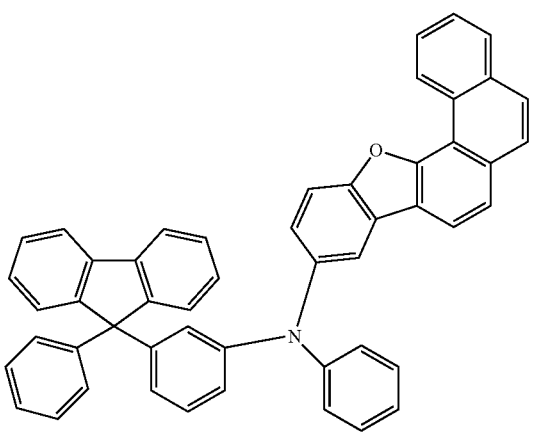
[A-123]
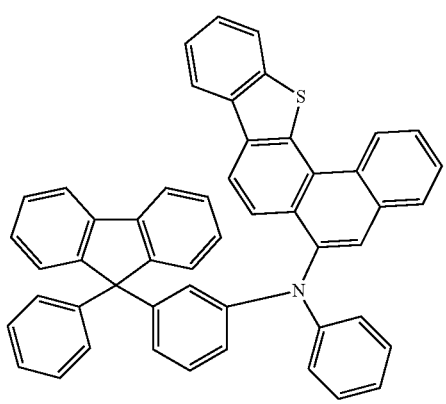
[A-124]
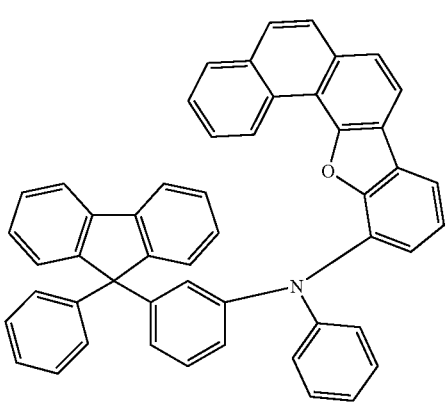
[A-127]
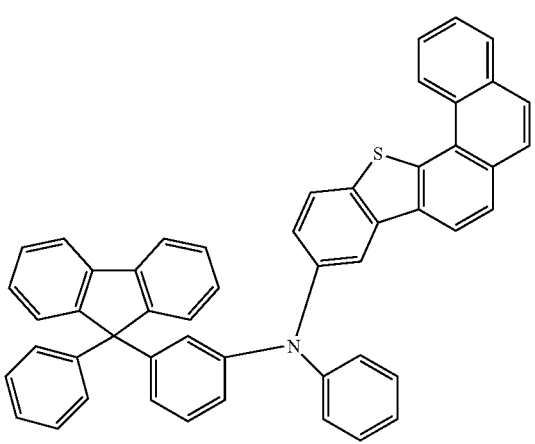

[A-128]
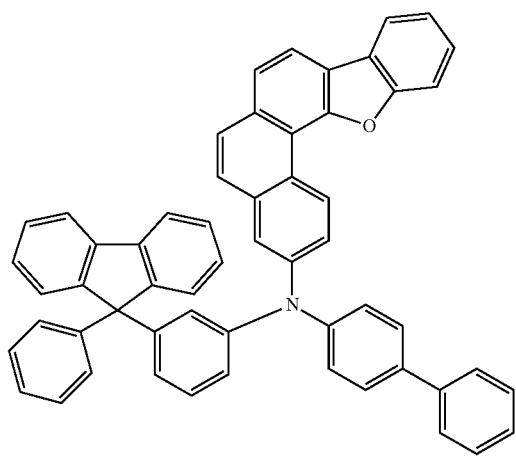
[A-131]
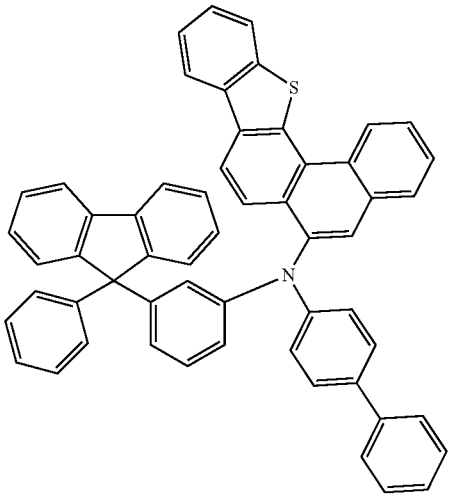
[A-129]
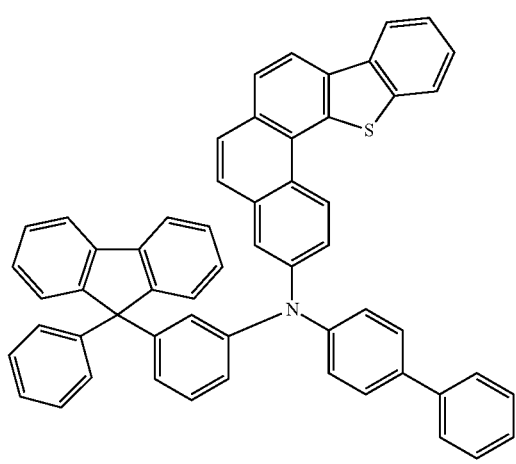
[A-132]
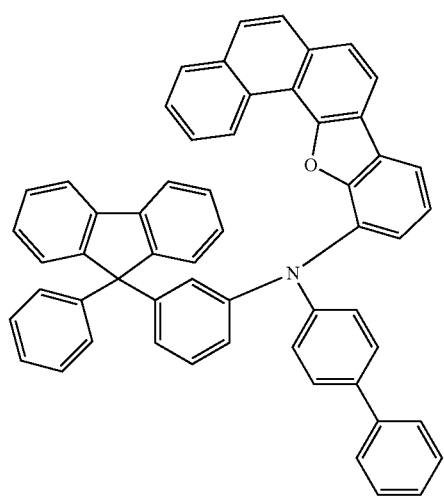
[A-130]
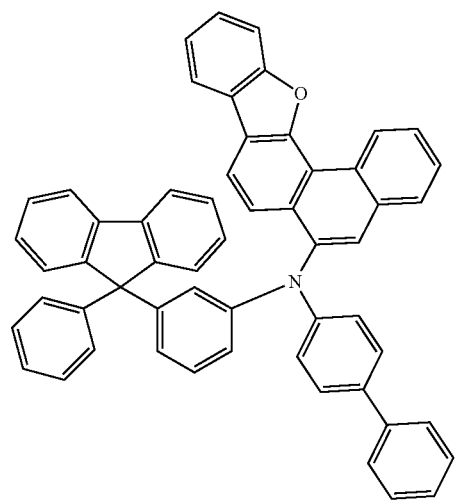
[A-133]
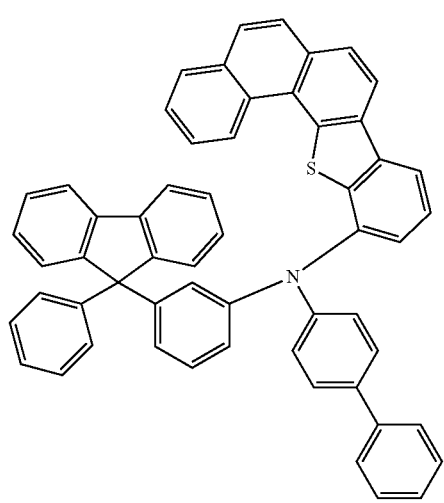

[A-134]
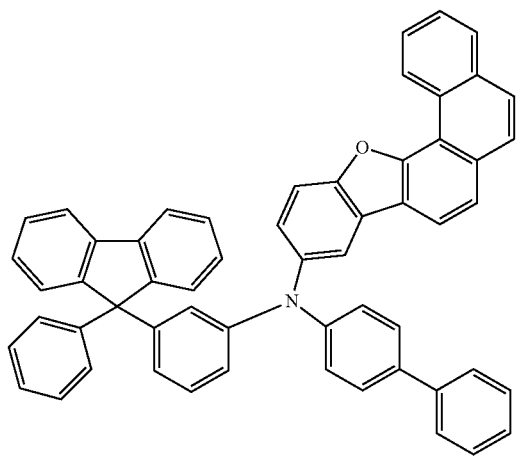
[A-135]
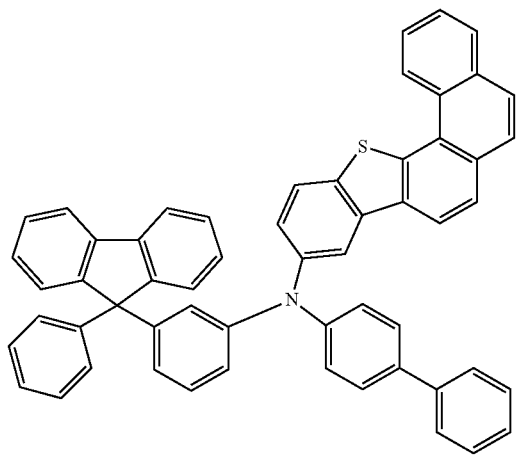
[A-136]
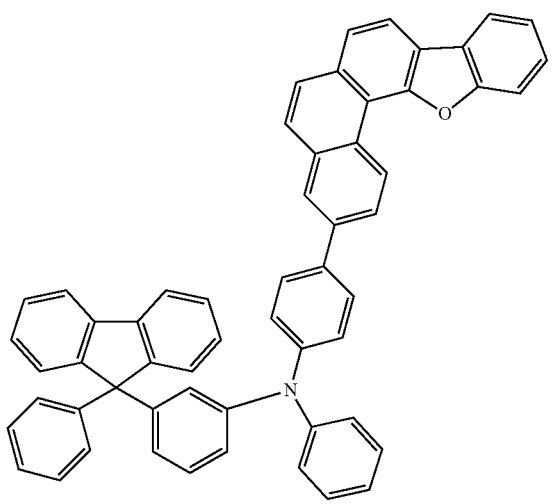
[A-137]
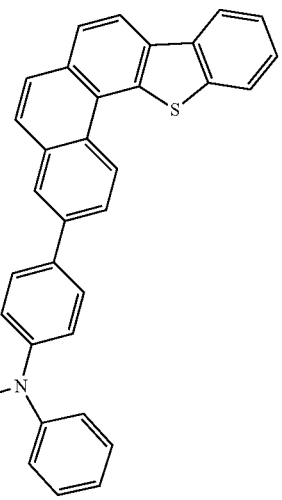
[A-138]
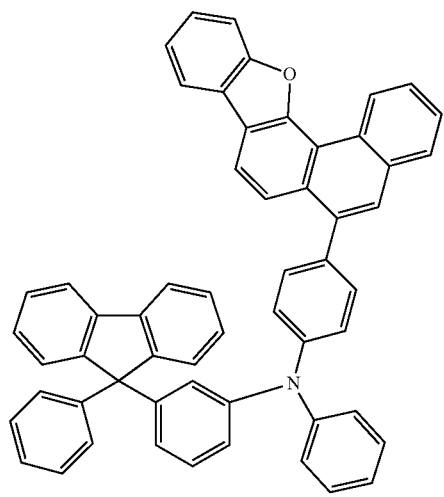
[A-139]
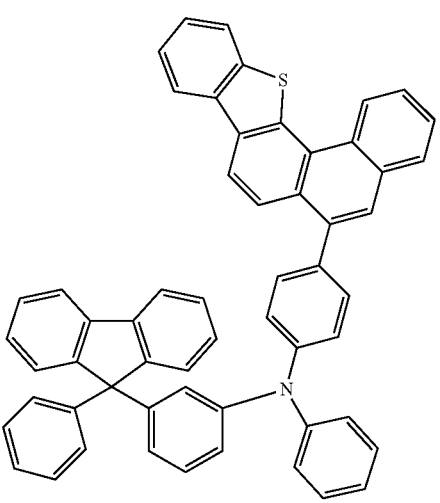

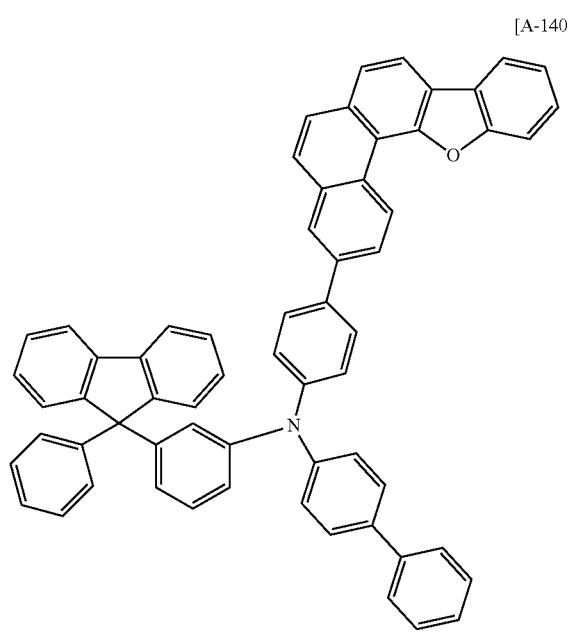

[A-140]

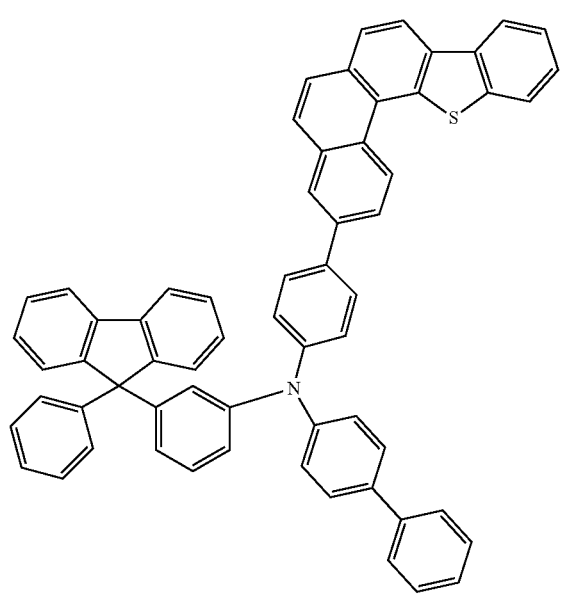

[A-141]

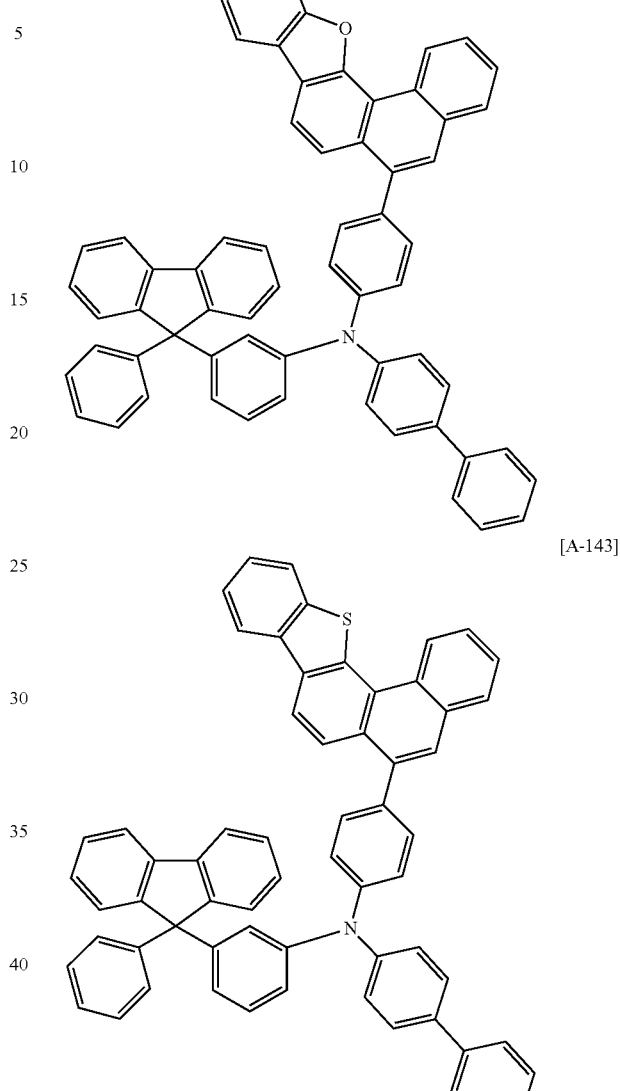

[A-142]

[A-143]

The organic compound may be applied to an organic optoelectronic device. The organic compound may be applied alone or with another organic compound to an organic optoelectronic device.

Hereinafter, an organic optoelectronic device including the organic compound is described.

The organic optoelectronic device may be any device to convert electrical energy into photoenergy and vice versa without particular limitation, and may be, for example an organic photoelectric device, an organic light emitting diode, an organic solar cell, and an organic photo-conductor drum.

The organic optoelectronic device includes an anode and a cathode facing each other, and at least one organic layer interposed between the anode and the cathode, wherein the organic layer includes the organic compound.

For example, the organic layer may be an emission layer including the organic compound.

For example, the organic layer may include an emission layer and an auxiliary layer between the emission layer and the anode, and the auxiliary layer may include the organic compound.

For example, the auxiliary layer may include a first auxiliary layer that is adjacent to the anode and a second auxiliary layer that is adjacent to the emission layer. For example, the second auxiliary layer may include the organic compound.

Herein, an organic light emitting diode as one example of an organic optoelectronic device is described referring to drawings.

FIG. 1 is a cross-sectional view of an organic light emitting diode according to an embodiment.

Referring to FIG. 1, an organic light emitting diode 200 according to an embodiment includes a cathode 110 and an anode 120 facing each other and an organic layer 105 interposed between the cathode 110 and the anode 120.

The cathode 110 may be made of a conductor having a low work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, LiO$_2$/Al, LiF/Ca, LiF/Al and BaF$_2$/Ca, but is not limited thereto.

The anode 120 may be made of a conductor having a high work function to help hole injection, and may be for example metal, metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or SnO$_2$ and Sb; a conductive polymer such as poly(3-methylthiophene), poly(3,4-(ethylene-1,2-dioxy)thiophene) (PEDT), polypyrrole, and polyaniline, but is not limited thereto.

The organic layer 105 includes an emission layer 130 including the organic compound.

The emission layer 130 may include the organic compound as a host, and may include the organic compound alone, at least two of the organic compounds, or a mixture of the organic compound and other organic compound.

The emission layer 130 may further include a dopant. The dopant may be a red, green, or blue dopant, for example a phosphorescent dopant.

The dopant is mixed with a host compound in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The emission layer 130 may be formed using a dry film formation method or a solution process. The dry film formation method may be, for example a chemical vapor deposition method, sputtering, plasma plating, and ion plating, and two or more compounds may be simultaneously formed into a film or compound having the same deposition temperature may be mixed and formed into a film. The solution process may be, for example inkjet printing, spin coating, slit coating, bar coating and/or dip coating.

The organic layer 105 may include an auxiliary layer 140 between the emission layer 130 and the anode 120. The auxiliary layer 140 may help charge injection and transfer between the anode 120 and the emission layer 130.

FIG. 2 is a cross-sectional view showing an organic light emitting diode according to another embodiment.

Referring to FIG. 2, an organic light emitting diode 200 according to another embodiment includes a cathode 110 and an anode 120 facing each other and an organic layer 105 interposed between the cathode 110 and the anode 120 and including the emission layer 130 and an auxiliary layer 140, like the above embodiment.

However, in the present embodiment unlike the above embodiment, the auxiliary layer 140 includes a first auxiliary layer 141 adjacent to the anode 120 and a second auxiliary layer 142 adjacent to the emission layer 130. The above organic compound may be included in the second auxiliary layer 142 adjacent to the emission layer 130.

In FIG. 1 or 2, at least one auxiliary layer as the organic layer 105 may be further included between the cathode 110 and the emission layer 130.

The organic light emitting diode may be applied to an organic light emitting diode (OLED) display.

MODE FOR INVENTION

Hereinafter, the embodiments are illustrated in more detail with reference to examples. These examples, however, are not in any sense to be interpreted as limiting the scope of the invention.

Synthesis of Organic Compound

Hereinafter, a starting material and a reactant used in Synthesis Examples and Examples were purchased from Sigma-Aldrich Corporation or TCI Inc. unless there was particularly mentioned.

Synthesis Example 1: Synthesis of Intermediate I-1

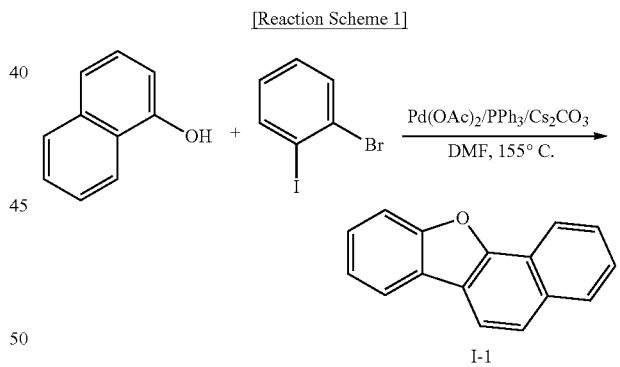

Naphthalen-1-ol (22 g, 192.70 mmol) was dissolved in 1 L of DMF (dimethylformamide) under a nitrogen environment, 1-bromo-2-iodobenzene (54.51 g, 192.70 mmol), triphenylphosphine (PPh$_3$) (10.11 g, 38.54 mmol), palladium (II) acetate (Pd(OAc)$_2$) (2.16 g, 9.63 mmol) were added thereto, and the mixture was stirred. Subsequently, cesium carbonate (Cs$_2$CO$_3$) (251.14 g, 770.78 mmol) was added thereto, and the obtained mixture was heated and refluxed at 155° C. for 12 hours. When the reaction was complete, water was added to the reaction solution, dichloromethane (DCM) was used for extraction, and an extract was treated with anhydrous MgSO$_4$ to remove moisture, filtered, and concentrated under a reduced pressure. The obtained residue was separated and purified through flash column chromatography to obtain an intermediate I-1 (37 g and 88%).

HRMS (70 eV. EI+): m/z, Calcd for C16H10O: 218.07, Found: 218 Elemental Analysis: C, 88%; H, 5%.

Synthesis Example 2: Synthesis of Intermediate I-2

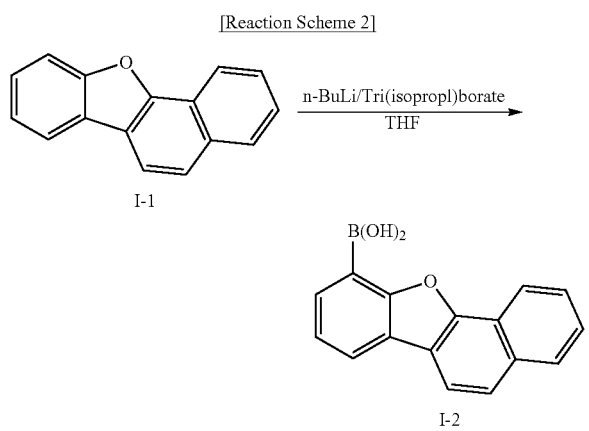

The intermediate I-1 (15 g, 69 mmol) was dissolved in THF (1 L) under a nitrogen environment, and the solution was stirred at −78° C. Subsequently, a 2.5 M n-butyl lithium solution (n-BuLi) (41 ml, 82.47 mmol) was added thereto still at −78° C., and the obtained mixture was stirred for 12 hours at room temperature. Then, tri(isopropl)borate (20.6 g, 109.92 mmol) was added thereto, and the obtained mixture was stirred at room temperature for 12 hours. When the reaction was complete, 1N HCl (150 ml) was added to the reaction solution, the mixture was stirred and extracted with dichloromethane (DCM), and an extract therefrom was filtered after removing moisture with anhydrous MgSO4 and concentrated under a reduced pressure. This obtained residue was separated and purified through flash column chromatography to obtain an intermediate I-2 (14 g and 78%).

HRMS (70 eV, EI+): m/z, Calcd for C16H11BO3: 262.08, Found: 262 Elemental Analysis: C, 73%; H, 4%.

Synthesis Example 3: Synthesis of Intermediate I-3

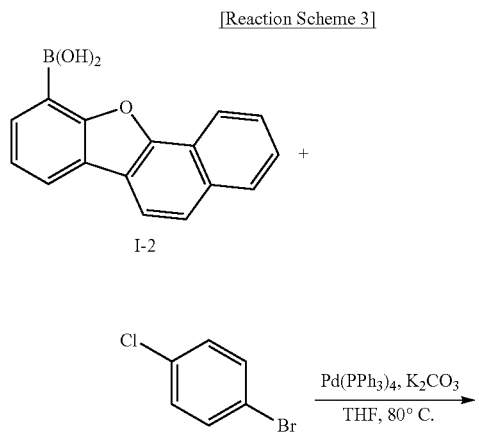

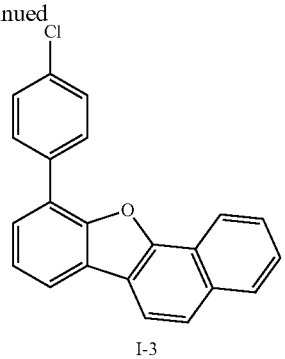

The intermediate I-2 (14 g, 53.4 mmol) was dissolved in THF (1 L) under a nitrogen environment, 1-bromo-4-chlorobenzene (12.3 g, 64.1 mmol) and tetrakis(triphenylphosphine)palladium (Pd(PPh3)4) (0.6 g, 0.53 mmol) were added thereto, and the mixture was stirred. Subsequently, potassium carbonate (K2CO3, 18.5 g, 134 mmol) saturated in water was added thereto, and the obtained mixture was heated and refluxed at 80° C. for 12 hours. When the reaction was complete, water was added to the reaction solution, dichloromethane (DCM) was used for extraction, and an extract was treated with anhydrous MgSO4 to remove moisture, filtered, and concentrated under a reduced pressure. This obtained residue was separated and purified through flash column chromatography to obtain an intermediate I-3 (10 g and 61%).

HRMS (70 eV, EI+): m/z, Calcd for C22H13ClO: 328.06, Found: 328 Elemental Analysis: C, 80%; H, 4%.

Synthesis Example 4: Synthesis of Intermediate I-4

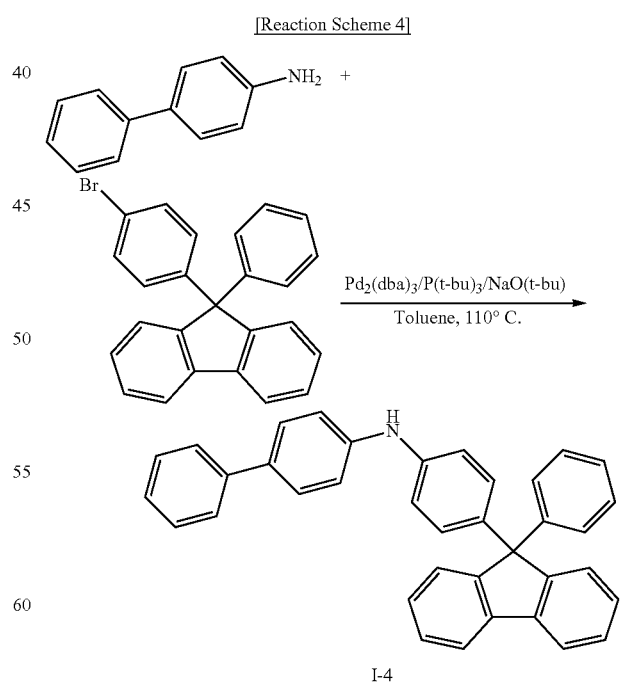

[1,1'-biphenyl]-4-amine (10 g, 59 mmol) was dissolved in 1 L of toluene under a nitrogen environment, 9-(4-bromophenyl)-9-phenyl-9H-fluorene (23.5 g, 59 mmol), tris (dibenzylideneacetone)dipalladium (0) Pd₂(dba)₃) (0.54 g, 0.59 mmol), tri-tert-butylphosphine (P(t-bu)₃) solution (50%) (2 ml, 2.36 mmol), and sodium t-butoxide (NaO(t-bu)) (6.8 g, 70 mmol) were added thereto, and the mixture was stirred and then, heated and refluxed at 110° C. for 12 hours. When the reaction was complete, water was added to the reaction solution, dichloromethane (DCM) was used for extraction, and an extract was treated with anhydrous MgSO₄ to remove moisture, filtered, and concentrated under a reduced pressure. This obtained residue was separated and purified through flash column chromatography to obtain an intermediate I-4 (22 g and 80%).

HRMS (70 eV, EI+): m/z, Calcd for C37H27N: 485.21, Found: 485 Elemental Analysis: C, 92%; H, 6%.

Synthesis Example 5: Synthesis of Intermediate 5

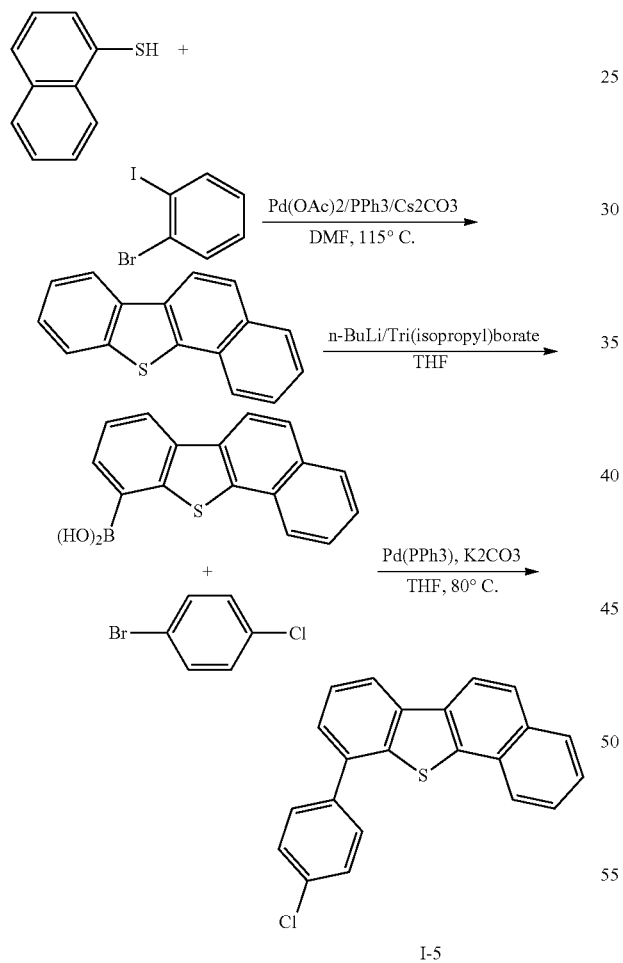

An intermediate I-5 was synthesized by sequentially performing the same synthesis processes as Synthesis Examples 1 to 3 except for using naphthalen-1-thiol instead of the naphthalen-1-ol as a starting material in Synthesis Example 1.

HRMS (70 eV, EI+): m/z, Calcd for C22H13ClS: 344.86, Found: 344 Elemental Analysis: C, 96.6%; H, 3.8%.

Example 1: Synthesis of Compound A-55

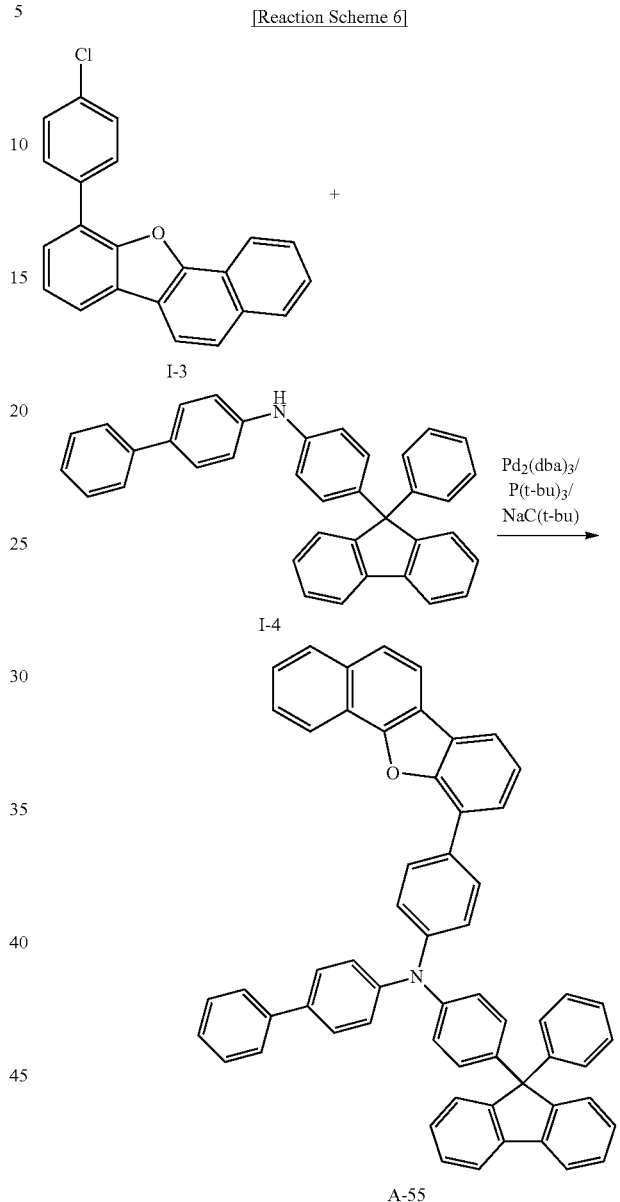

The intermediate I-3 (4 g, 9 mmol) was dissolved in toluene (0.5 L) under a nitrogen environment, the intermediate I-4 (4.4 g, 9 mmol), tris(dibenzylideneacetone)dipalladium (0) Pd₂(dba)₃) (0.82 g, 0.09 mmol), tri-tert-butylphosphine (P(t-bu)₃) solution 50% (0.2 ml, 0.36 mmol), and sodium t-butoxide (NaO(t-bu)) (1 g, 10.92 mmol) were added thereto, and the mixture was stirred and then, heated and refluxed at 110° C. for 12 hours. When the reaction was complete, water was added to the reaction solution, dichloromethane (DCM) was used for extraction, and an extract was treated with anhydrous MgSO₄ to remove moisture, filtered, and concentrated under a reduced pressure. This obtained residue was separated and purified through flash column chromatography to obtain a compound A-55 (6.5 g, 90%).

HRMS (70 eV, EI+): m/z, Calcd for C59H39NO: 777.30, Found: 777, Elemental Analysis: C, 91%; H, 5%.

Example 2: Synthesis of Compound A-56

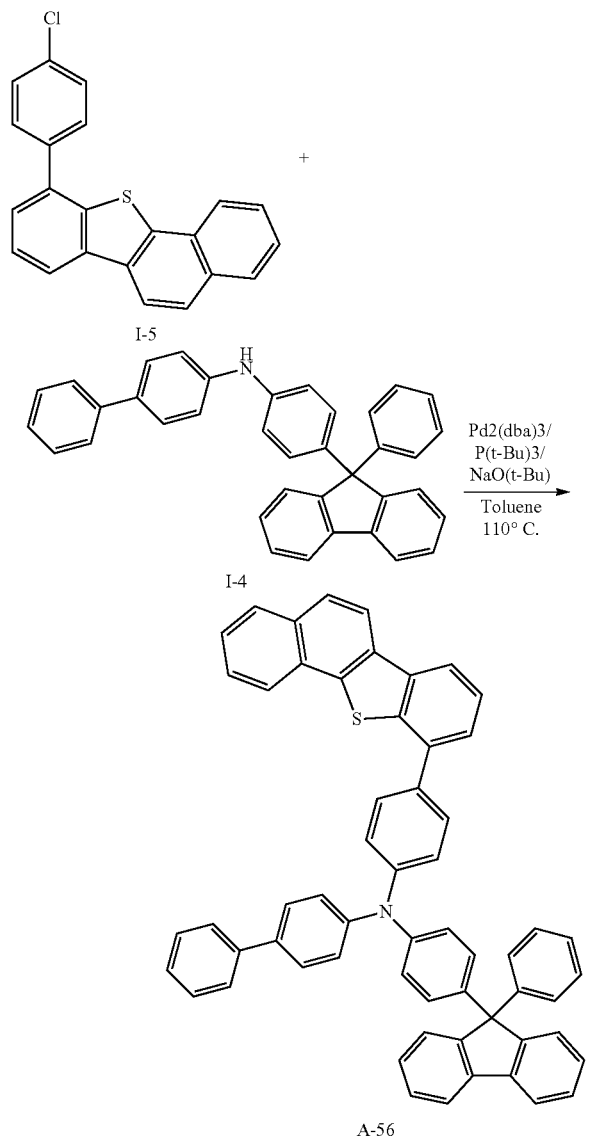

A compound A-56 was synthesized by using the intermediate 5 instead of the intermediate 3 in Example 1.

HRMS (70 eV, EI+): m/z, Calcd for C59H39NS: 793.28, Found: 793, Elemental Analysis: C, 89.25%; H, 4.95%.

Manufacture of Blue Organic Light Emitting Diode

Device Example 1

ITO (indium tin oxide) was coated to be 1500 Å thick on a glass substrate, and the coated glass was ultrasonic wave-washed with a distilled water. After washing with distilled water, the washed glass substrate was ultrasonic wave-washed with a solvent such as isopropyl alcohol, acetone, methanol, and the like was moved to a plasma cleaner to clean the substrate by using oxygen plasma for 10 minutes and moved to a vacuum depositor.

Subsequently, N4,N4'-diphenyl-N4,N4'-bis(9-phenyl-9H-carbazol-3-yl)biphenyl-4,4'-diamine (compound A) was vacuum-deposited on the ITO substrate to form a 700 Å-thick hole injection layer, 1,4,5,8,9,11-hexaazatriphenylene-hexacarbonitrile (HAT-CN) (compound B) was deposited in a 50 Å thickness on the hole injection layer, and N-(biphenyl-4-yl)-9,9-dimethyl-N-(4-(9-phenyl-9H-carbazol-3-yl)phenyl)-9H-fluoren-2-amine(compound C) was deposited in a 700 Å thickness to form a hole transport layer.

The compound according to Example 1 was vacuum-deposited on the hole transport layer as a hole transport auxiliary layer to form a 50 Å-thick auxiliary hole transport layer. 9,10-di-(2-naphthyl)anthracene (ADN) was used as a host and 3 wt % of 2,5,8,11-tetra(tert-butyl)perylene (TBPe) as a dopant was vacuum-deposited on the auxiliary hole transport layer to form a 250 Å-thick emission layer.

Subsequently, 8-(4-(4-(naphthalen-2-yl)-6-(naphthalen-3-yl)-1,3,5-triazin-2-yl)phenyl)quinoline (compound D) and Liq were simultaneously vacuum-deposited in a 1:1 ratio on the emission layer to 300 Å-thick electron transport layer and 15 Å of Liq and 1200 Å of Al were sequentially vacuum-deposited to form a cathode on the electron transport layer to manufacture an organic light emitting diode.

The organic light emitting diode has a structure of ITO/A 700 Å/B 50 Å/C 700 Å/hole transport auxiliary layer 50 Å]/EML [ADN:TBPe=97:3] 250 Å/D:Liq 300 Å/Liq 15 Å/Al 1200 Å.

Device Example 2

An organic light emitting diode was manufactured according to the same method as Device Example 1 except for using the compound according to Example 2 instead of the compound according to Example 1 to form the hole transport auxiliary layer.

Comparative Example 1

An organic light emitting diode was manufactured according to the same method as Device Example 1 except for using the compound C instead of the compound according to Example 1 to form the hole transport auxiliary layer.

Compounds used for manufacture of the organic light emitting diode are as follows.

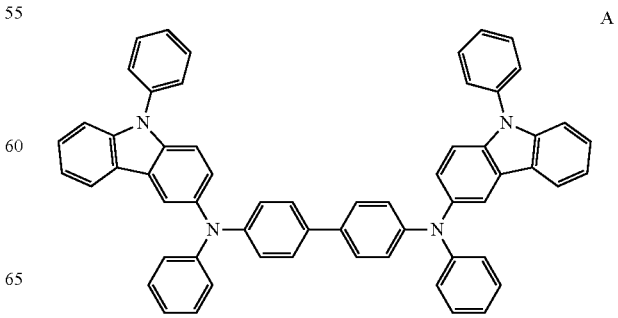

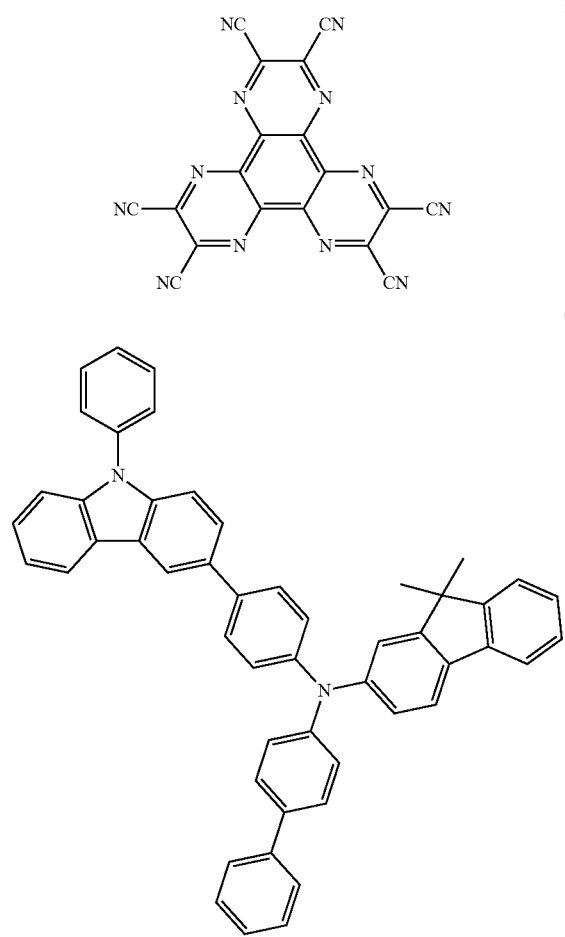

B

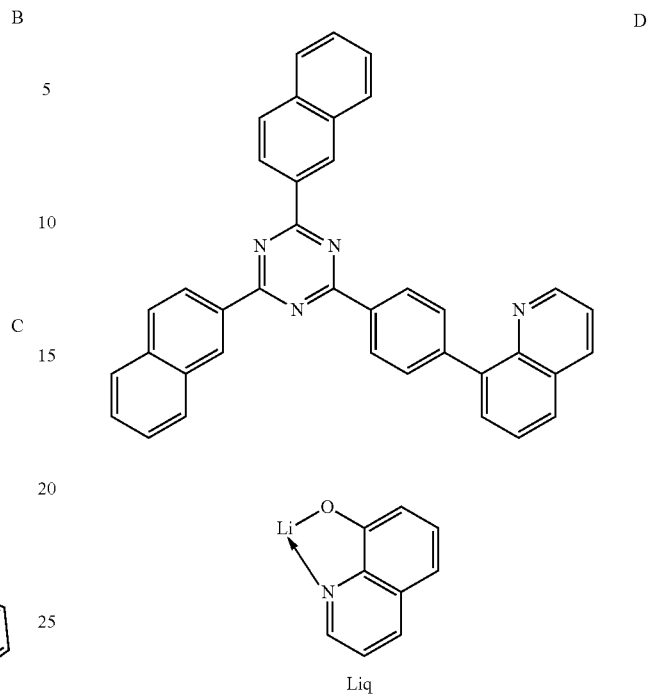

D

ADN

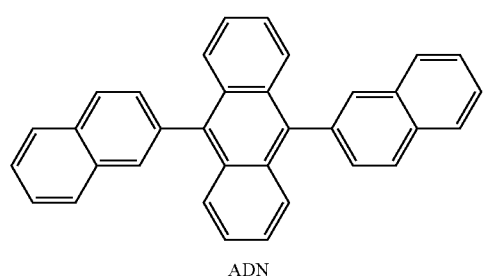

TBPe

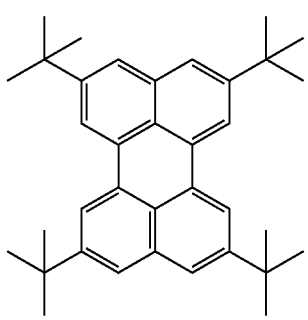

Liq

Performance Measurement of Blue Organic Light Emitting Diode

Current density change, luminance change, and luminous efficiency of each organic light emitting diode according to Examples 1 and 2 and Comparative Example 1 are measured.

Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the result.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

Life-spans of the blue organic light emitting diodes according to Device Examples 1 and 2 and Comparative Example 1 were measured as a time when their luminance decreased down to ½ relative to the initial luminance (cd/m$^2$) after emitting light with 750 nit as the initial luminance (cd/m$^2$) and measuring their luminance decrease depending on a time with a Polanonix life-span measurement system.

TABLE 1

| Devices | Hole transport layer (HTL) | Hole transport auxiliary layer | Driving voltage (V) | Light emitting color (EL color) | Efficiency (cd/A) | Half-life of life-span (h) at 1000 cd/m$^2$ |
|---|---|---|---|---|---|---|
| Device Example 1 | compound C | Compound A-55 | 4.3 | Blue | 6.5 | 1,550 |
| Device Example 2 | compound C | compound A-56 | 4.3 | Blue | 6.6 | 1,500 |
| Comparative Example 1 | compound C | Compound C | 4.3 | Blue | 5.5 | 1,250 |

As shown in Table 1, the organic light emitting diodes according to Examples 1 and 2 showed improved luminous efficiency and half-life of a life-span compared with the organic light emitting diode according to Comparative Example 1. Particularly, the organic light emitting diodes according to Examples 1 and 2 showed greater than or equal to about 15% efficiency increase and half-life increase of a life-span compared with the organic light emitting diode according to Comparative Example 1.

Manufacture of Green Organic Light Emitting Diode

Device Example 3

ITO was coated to be 1500 Å thick on a glass substrate, and the coated glass was ultrasonic wave-washed with a distilled water. After washing with distilled water, the washed glass substrate was ultrasonic wave-washed with a solvent such as isopropyl alcohol, acetone, methanol, and the like was moved to a plasma cleaner to clean the substrate by using oxygen plasma for 10 minutes and moved to a vacuum depositor.

Subsequently, N4,N4'-diphenyl-N4,N4'-bis(9-phenyl-9H-carbazol-3-yl)biphenyl-4,4'-diamine (compound A) was vacuum-deposited on the ITO substrate to form a 700 Å-thick hole injection layer, 1,4,5,8,9,11-hexaazatriphenylene-hexacarbonitrile (HAT-CN) (compound B) was deposited to be 50 Å-thick on the hole injection layer, and N-(biphenyl-4-yl)-9,9-dimethyl-N-(4-(9-phenyl-9H-carbazol-3-yl)phenyl)-9H-fluoren-2-amine was deposited to form a 700 Å-thick hole transport layer. The compound according to Example 1 was vacuum-deposited on the hole transport layer to form a 320 Å-thick hole transport auxiliary layer. Subsequently, CBP was used as a host and 7 wt % of tris(4-methyl-2,5-diphenylpyridine)iridium (III) (compound E) as a dopant on the hole transport auxiliary layer to form a 400 Å-thick emission layer. Then, 8-(4-(4-(naphthalen-2-yl)-6-(naphthalen-3-yl)-1,3,5-triazin-2-yl)phenyequinoline (compound D) and Liq were simultaneously vacuum-deposited in a 1:1 ratio on the emission layer to 300 Å-thick electron transport layer and 15 Å of Liq and 1200 Å of Al were sequentially vacuum-deposited to form a cathode on the electron transport layer to manufacture an organic light emitting diode.

The organic light emitting diode has a structure of ITO/A 700 Å/B 50 Å/C 700 Å/hole transport auxiliary layer 320 Å/EML [CBP:E=93%:7%] 400 Å/D:Liq 300 Å/Liq 15 Å/Al 1200 Å.

Device Example 4

An organic light emitting diode was manufactured according to the same method as Device Example 3 except for using the compound according to Example 2 instead of the compound according to Example 1 to form the hole transport auxiliary layer.

Comparative Example 2

An organic light emitting diode was manufactured according to the same method as Device Example 3 except for using the compound C instead of the compound according to Example 1 to form the hole transport auxiliary layer.

Compounds used for manufacture of the organic light emitting diode are as follows.

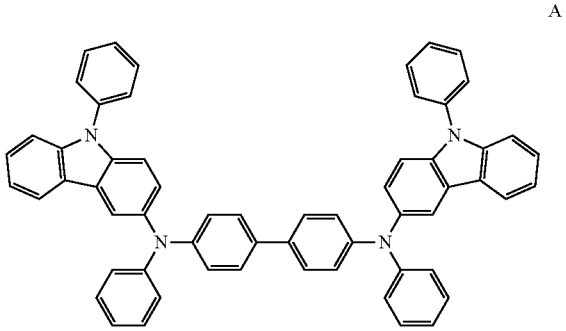

A

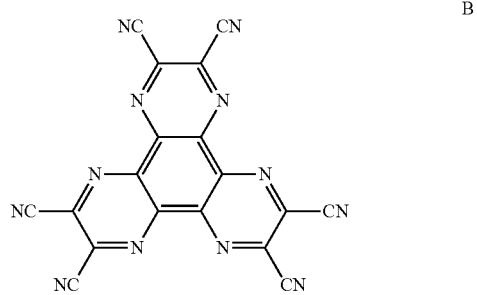

B

-continued

C

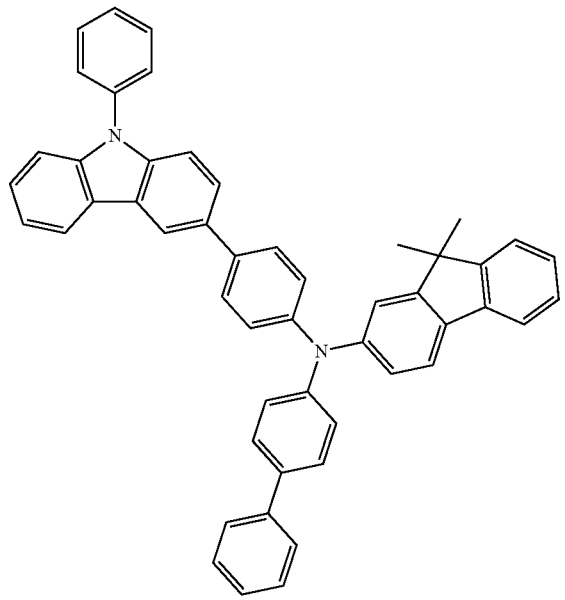

D

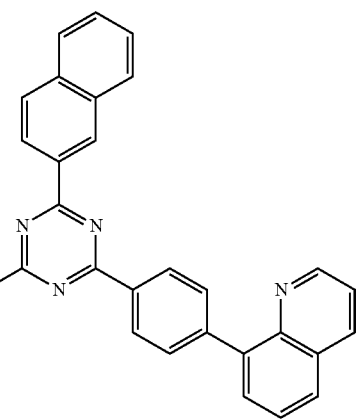

E

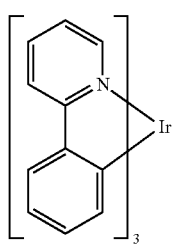

-continued

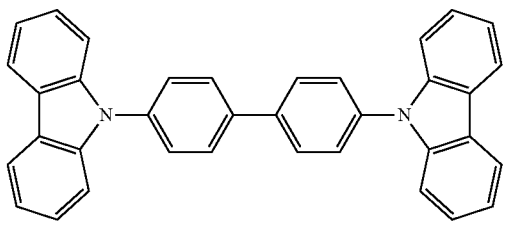

CBP

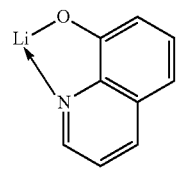

Liq

Performance Measurement of Green Organic Light Emitting Diode

Current density change, luminance change, and luminous efficiency of each organic light emitting diode according to Device Examples 3 and 4 and Comparative Example 2 are measured.

Specific measurement methods are as follows, and the results are shown in Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the result.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

TABLE 2

| Device | Hole transport layer (HTL) | Hole transport auxiliary layer | Driving voltage (V) | Light emitting color (X, Y) | Efficiency (cd/A) |
|---|---|---|---|---|---|
| Device Example 3 | Compound C | Compound A-55 | 4.6 | 0.336, 0.609 | 56 |
| Device Example 4 | Compound C | compound A-56 | 4.6 | 0.338, 0.607 | 57 |
| Comparative Example 2 | Compound C | compound C | 4.5 | 0.338, 0.608 | 49 |

As shown in Table 2, the organic light emitting diodes according to Device Examples 3 and 4 showed greater than or equal to 15% increased luminous efficiency compared with the organic light emitting diode according to Comparative Example 2.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS 200, 300: organic light emitting diode
105: organic layer
110: cathode
120: anode
130: emission layer
140: auxiliary layer
141: first auxiliary layer
142: second auxiliary layer

The invention claimed is:
1. An organic optoelectronic device, comprising:
an anode and a cathode facing each other,
an emission layer between the anode and the cathode, and
an auxiliary layer between the emission layer and the anode,
wherein the auxiliary layer includes:
a first auxiliary layer that is adjacent to the anode, and
a second auxiliary layer that is adjacent to the emission layer,
wherein the second auxiliary layer includes an organic compound represented by Chemical Formula 1:

[Chemical Formula 1]

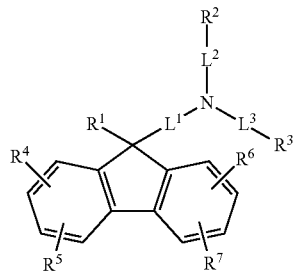

wherein, in Chemical Formula 1,
$L^1$ to $L^3$ are independently a single bond, a substituted or unsubstituted C6 to C30 arylene group, a substituted or unsubstituted C2 to C30 heterocyclic group, or a combination thereof,
$R^1$ to $R^7$ are independently hydrogen, deuterium, a substituted or unsubstituted C1 to C30 alkyl group, a substituted or unsubstituted C3 to C30 cycloalkyl group, a substituted or unsubstituted C2 to C30 heterocyclic group, a substituted or unsubstituted C6 to C30 aryl group, a halogen, a cyano group, a hydroxyl group, an amino group, a nitro group, or a combination thereof,
$R^4$ to $R^7$ are independently present or adjacent two are linked to each other to provide a ring, and at least one of $R^2$ and $R^3$ is a group represented by Chemical Formula 2,

[Chemical Formula 2]

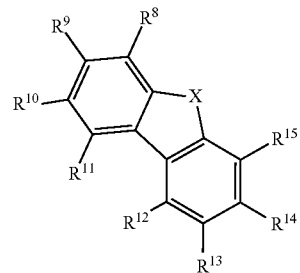

wherein, in Chemical Formula 2,
X is O, S, SO$_2$, or SiR$^c$R$^d$, and
adjacent two of $R^8$ to $R^{15}$ are linked to each other to provide a ring represented by one of Chemical Formulae 2-A to 2-C,

[Chemical Formula 2-A]

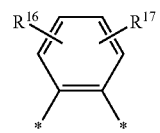

[Chemical Formula 2-B]

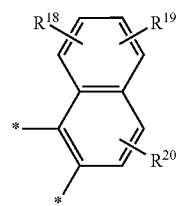

[Chemical Formula 2-C]

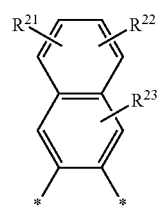

wherein, in Chemical Formulae 2-A to 2-C,
* is a linking point,
$R^8$ to $R^{15}$ not providing a ring, $R^{16}$ to $R^{23}$, and $R^c$ to $R^d$ are independently hydrogen, deuterium, a substituted or unsubstituted C1 to C30 alkyl group, a substituted or unsubstituted C3 to C30 cycloalkyl group, a substituted or unsubstituted C2 to C30 heterocyclic group, a substituted or unsubstituted C6 to C30 aryl group, a substituted or unsubstituted C6 to C30 arylamine group, a halogen, a cyano group, a hydroxyl group, an amino group, a nitro group, or a combination thereof, or are a linking point with $L^2$ or $L^3$ of Chemical Formula 1.

2. The organic optoelectronic device of claim 1, wherein Chemical Formula 2 is one of substituted or unsubstituted groups listed in Group 1:
[Group 1]
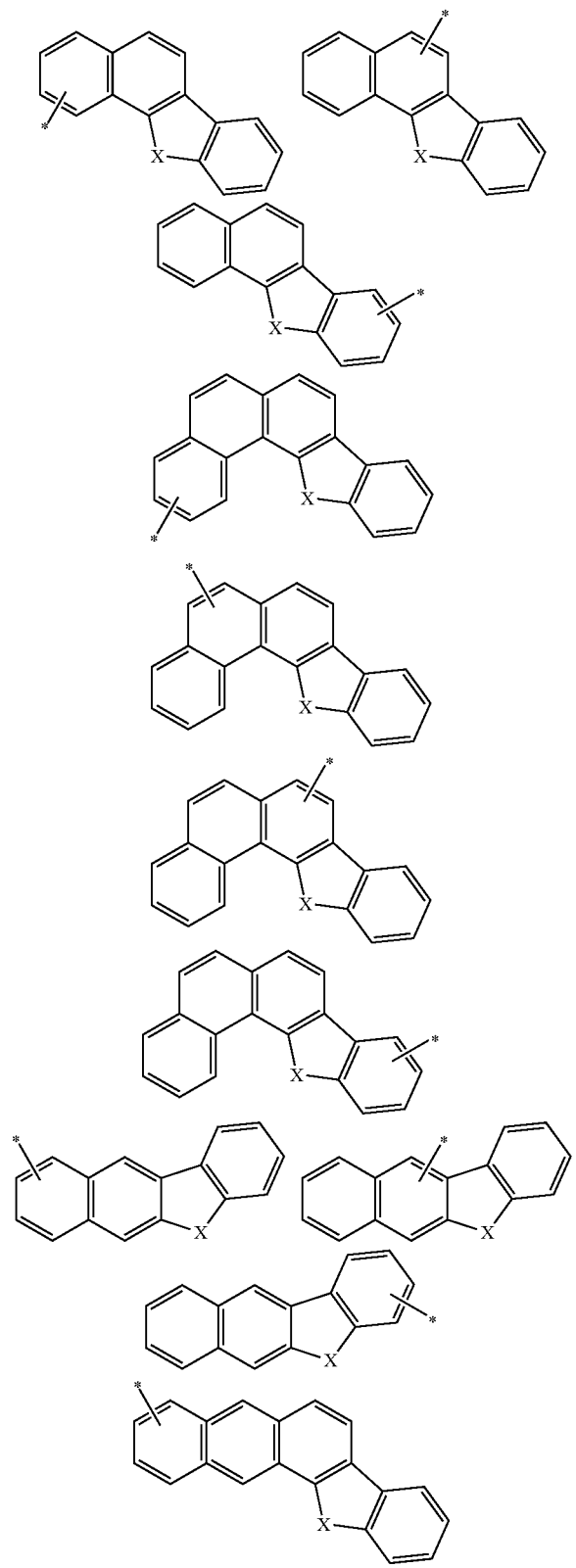
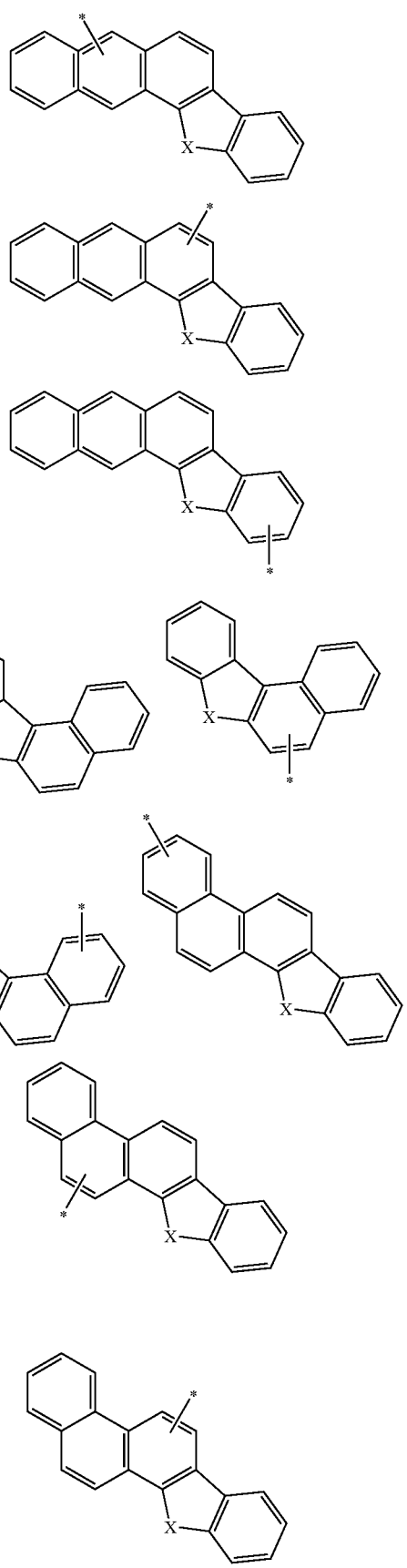

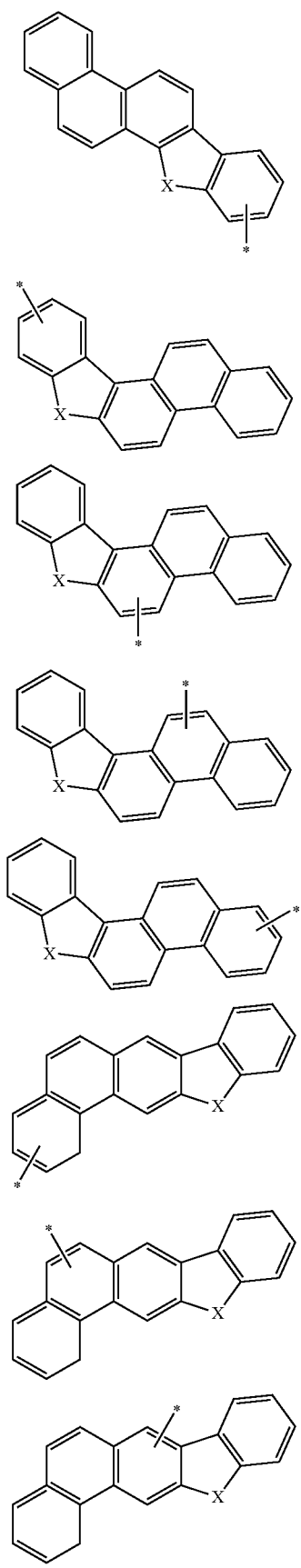
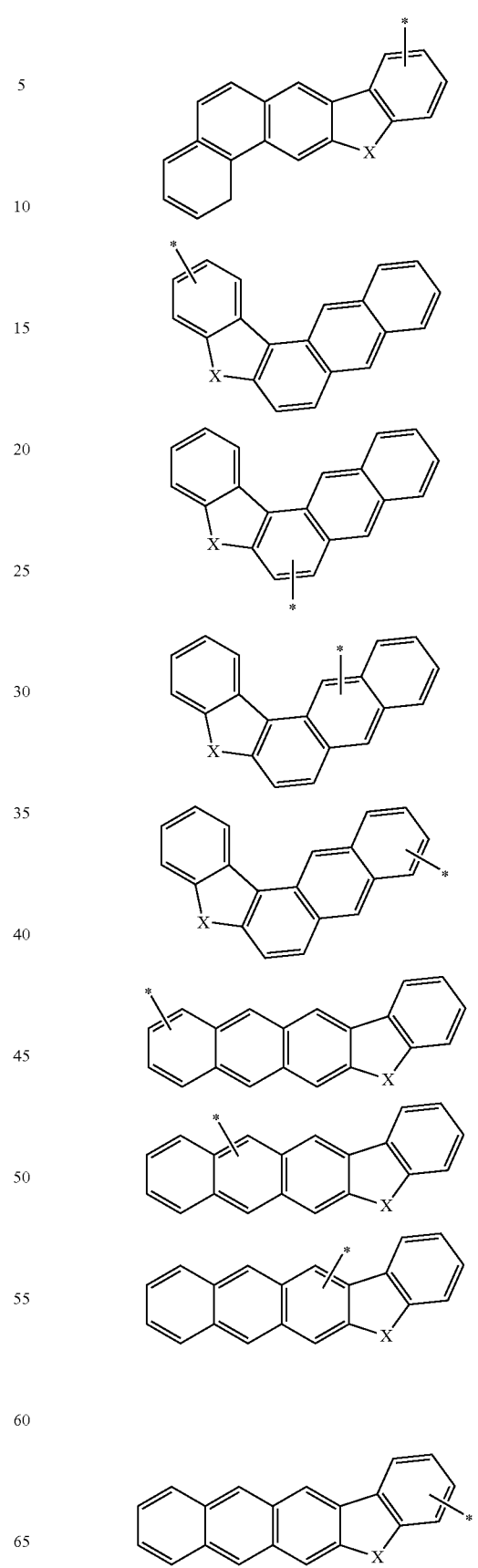

-continued

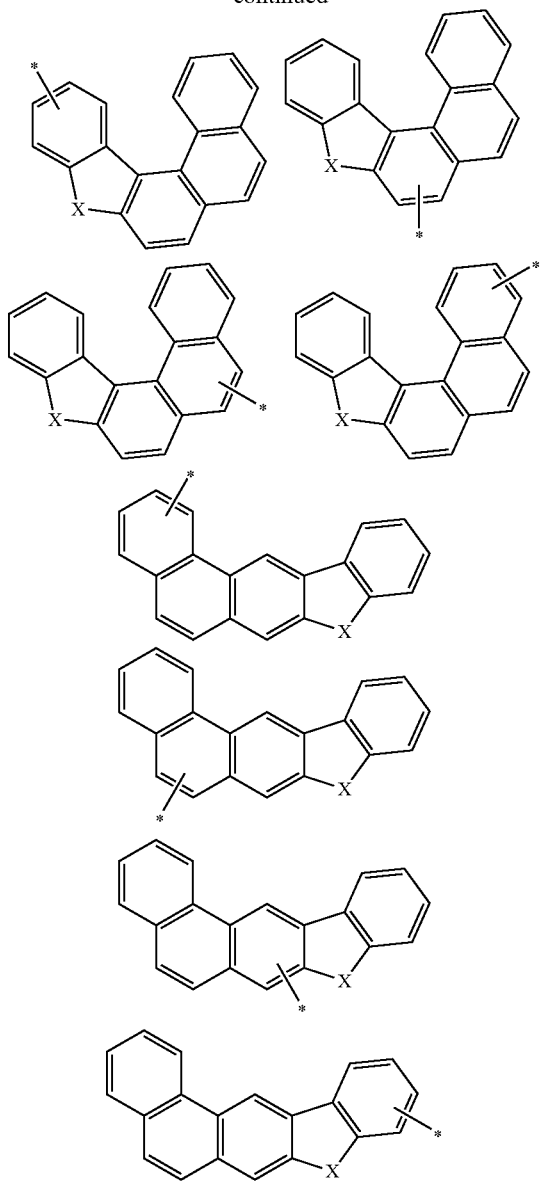

wherein, in Group 1,
* is a linking point,
X is O, S, SO$_2$, or SiR$^c$R$^d$, and
R$^c$ and R$^d$ are independently hydrogen, deuterium, a substituted or unsubstituted C1 to C30 alkyl group, a substituted or unsubstituted C3 to C30 cycloalkyl group, a substituted or unsubstituted C2 to C30 heterocyclic group, a substituted or unsubstituted C6 to C30 aryl group, a halogen, a cyano group, a hydroxyl group, an amino group, a nitro group, or a combination thereof.

3. The organic optoelectronic device of claim 1, wherein X is O or S.

4. The organic optoelectronic device of claim 1, wherein R$^2$ is the group represented by Chemical Formula 2, and
R$^1$ and R$^3$ are independently a substituted or unsubstituted phenyl group, a substituted or unsubstituted biphenyl group, a substituted or unsubstituted terphenyl group, a substituted or unsubstituted quarterphenyl group, a substituted or unsubstituted naphthyl group, a substituted or unsubstituted anthracenyl group, a substituted or unsubstituted phenanthryl group, or a combination thereof.

5. The organic optoelectronic device of claim 1, wherein L$^1$ to L$^3$ are independently a single bond, a substituted or unsubstituted phenylene group, a substituted or unsubstituted biphenylene group, a substituted or unsubstituted naphthylene group, or a combination thereof.

6. The organic optoelectronic device of claim 5, wherein L$^1$ to L$^3$ are independently a single bond, a substituted or unsubstituted m-phenylene group, or a substituted or unsubstituted p-phenylene group.

7. The organic optoelectronic device of claim 1, wherein the organic compound is one of compounds listed in Group 2:

[Group 2]

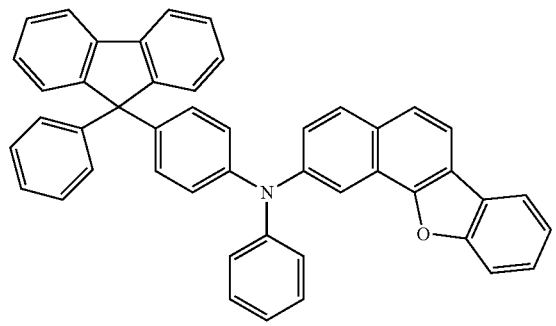

[A-1]

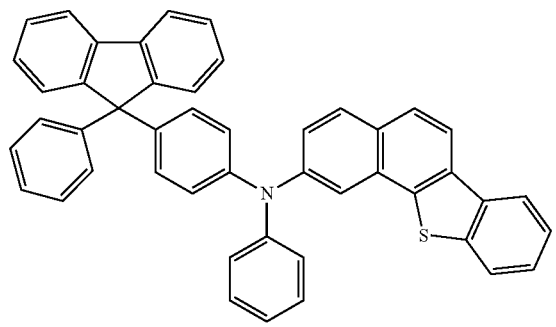

[A-2]

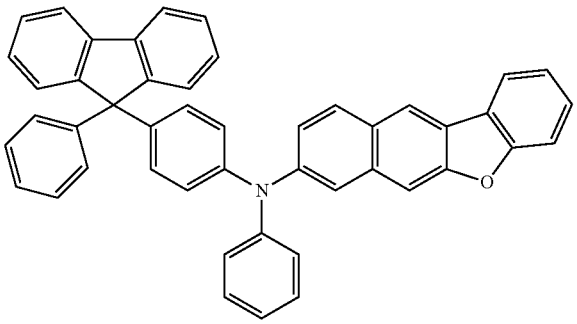

[A-3]

[A-4]
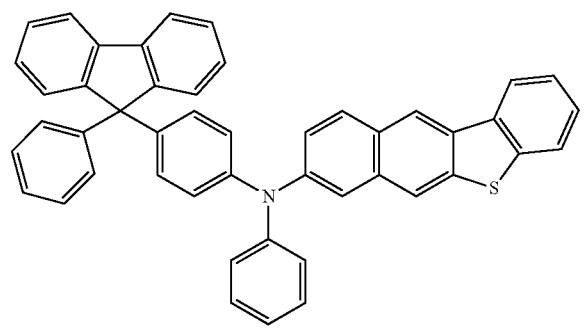
[A-8]
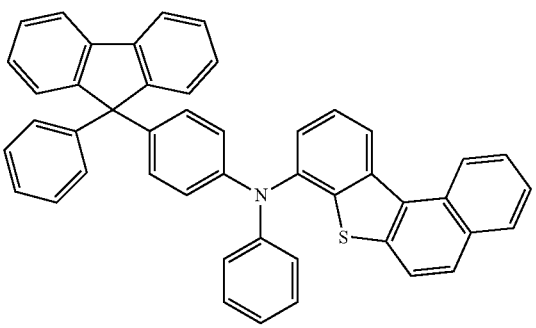
[A-5]
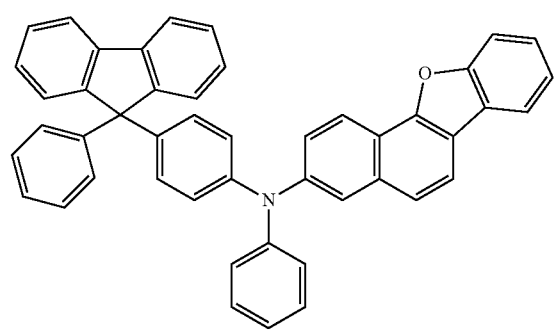
[A-9]
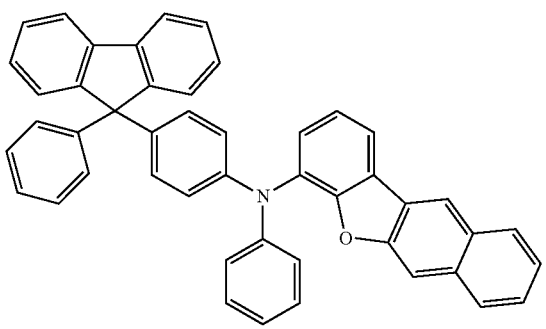
[A-6]
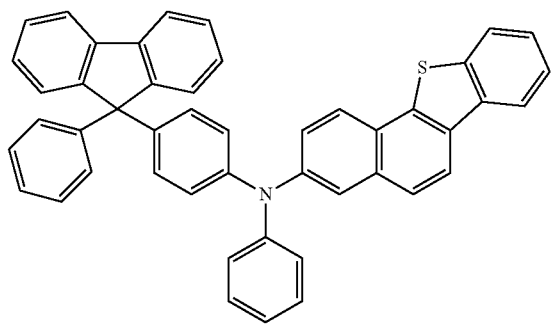
[A-10]
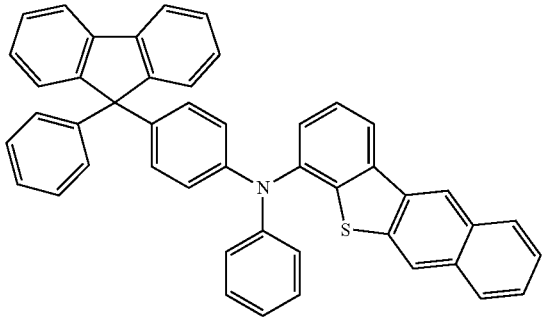
[A-7]
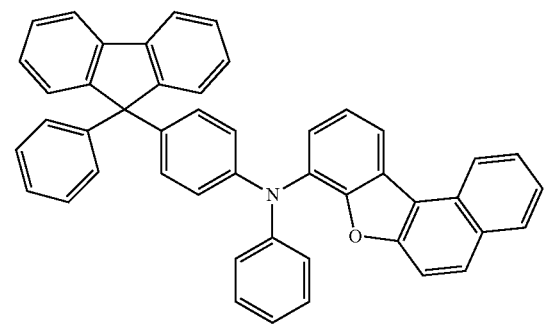
[A-11]
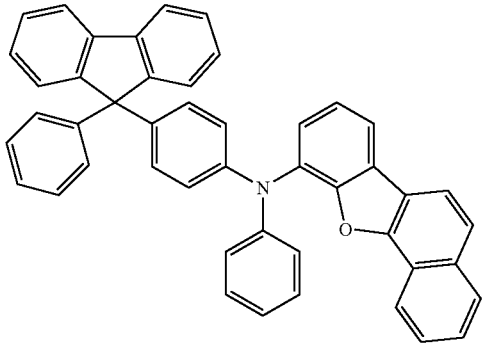

[A-12]

[A-13]

[A-14]

[A-15]

[A-16]

[A-17]

[A-18]

[A-19]
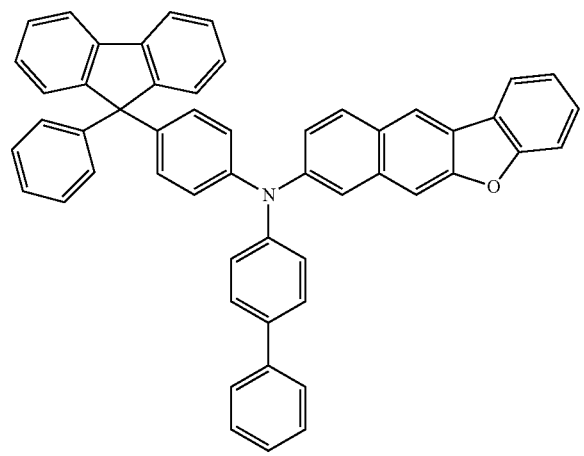
[A-22]
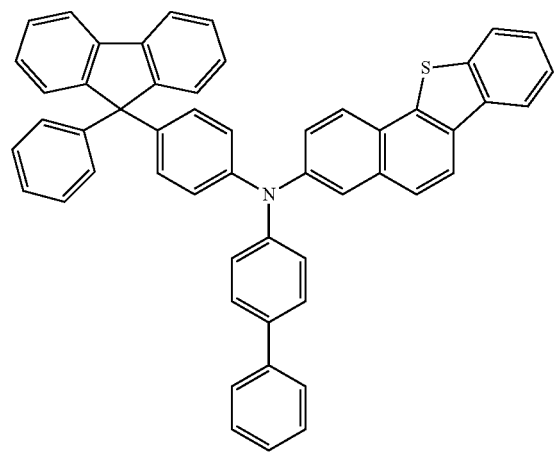
[A-20]
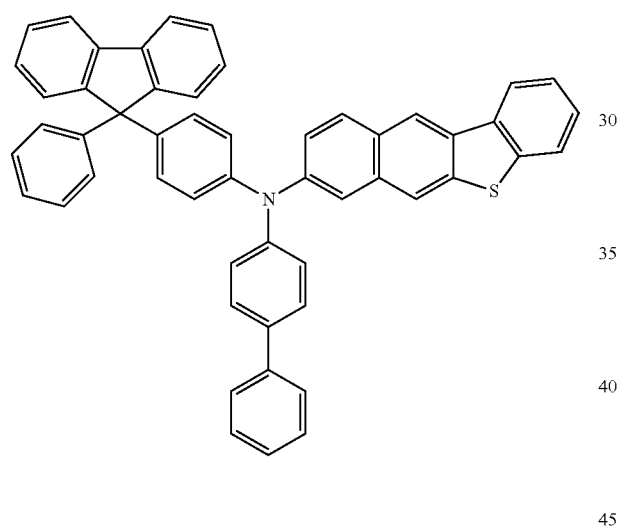
[A-23]
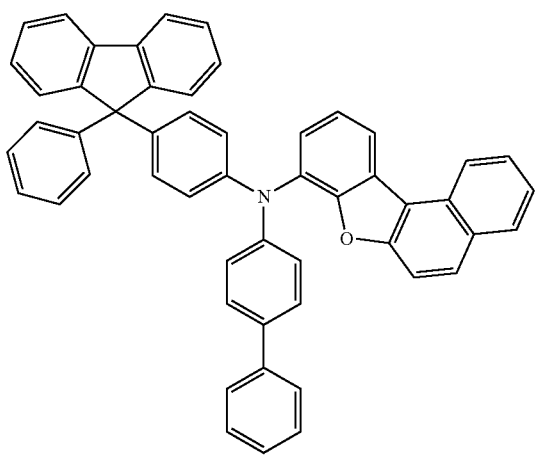
[A-21]
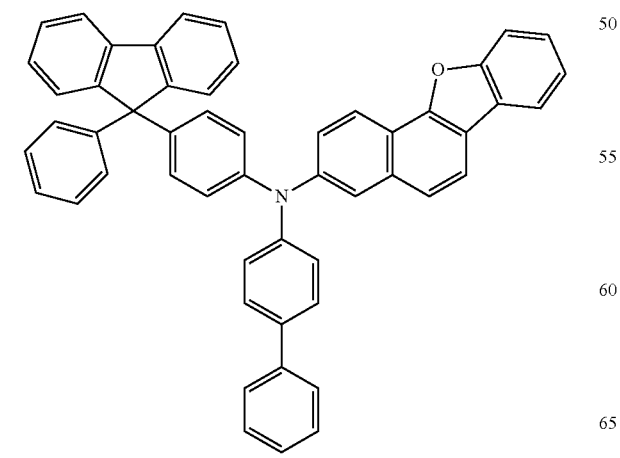
[A-24]
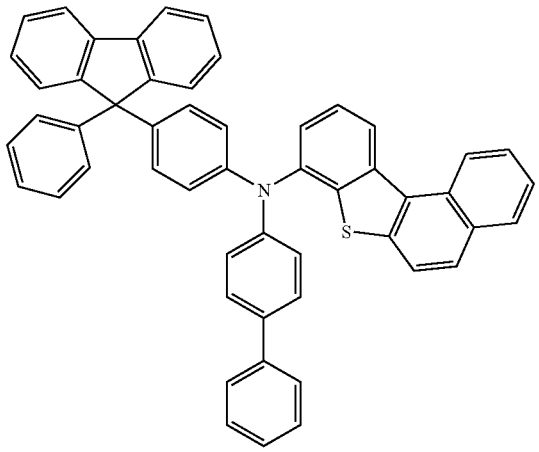

-continued
[A-25]
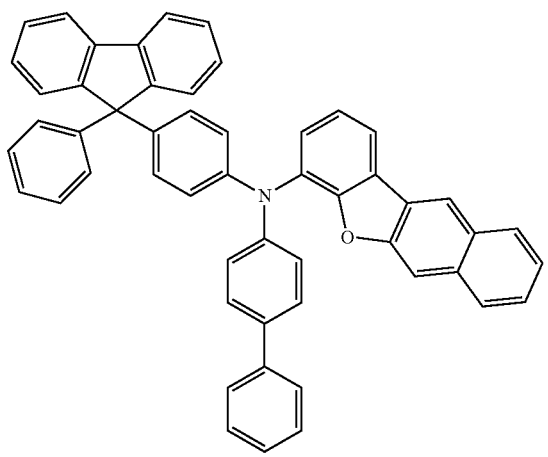
[A-26]
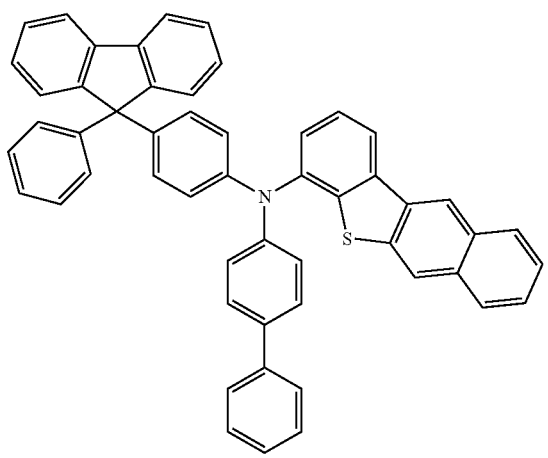
[A-27]
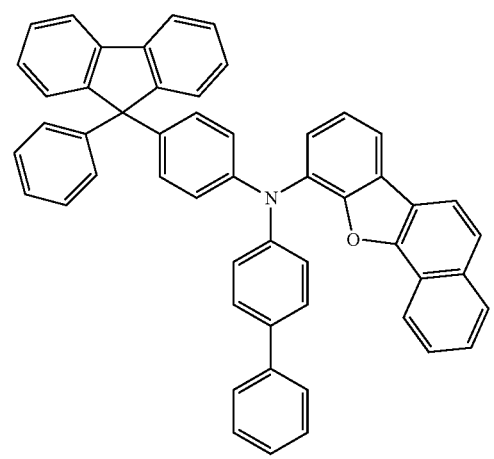
[A-28]
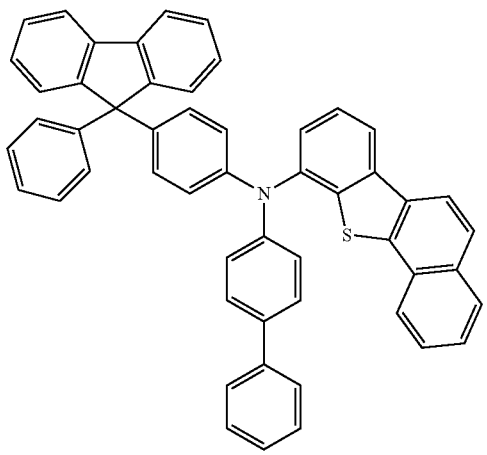
[A-29]
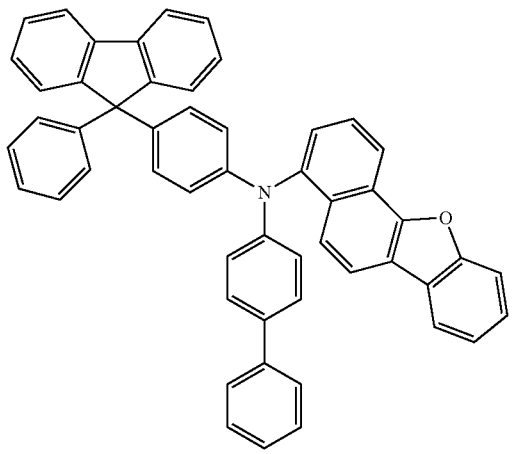
[A-30]
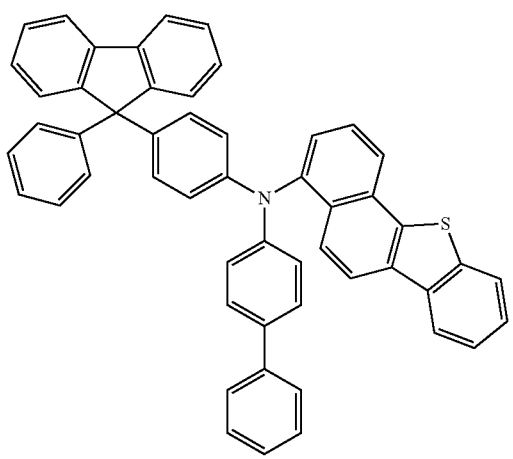

[A-31]
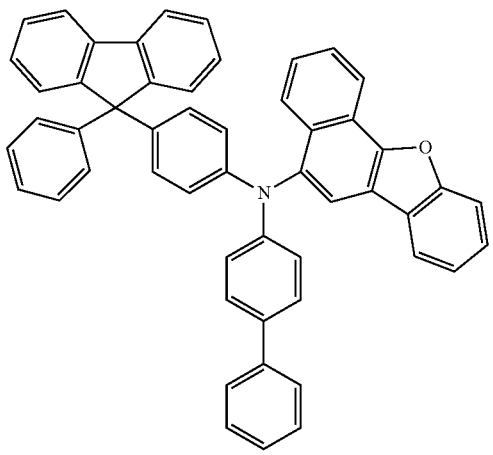
[A-34]
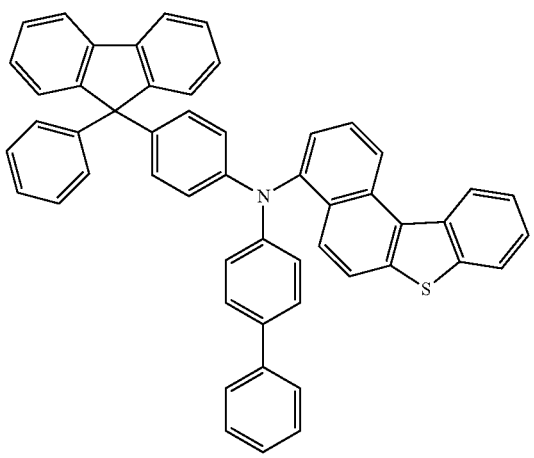
[A-32]
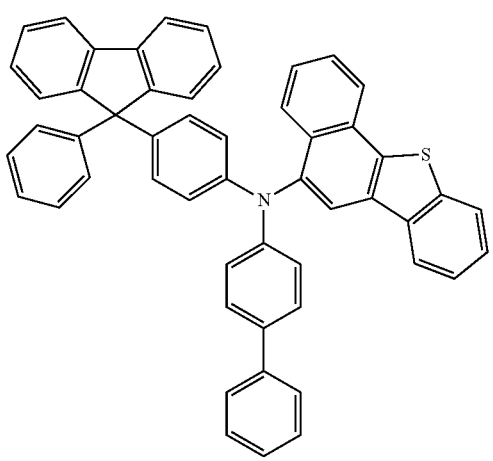
[A-35]
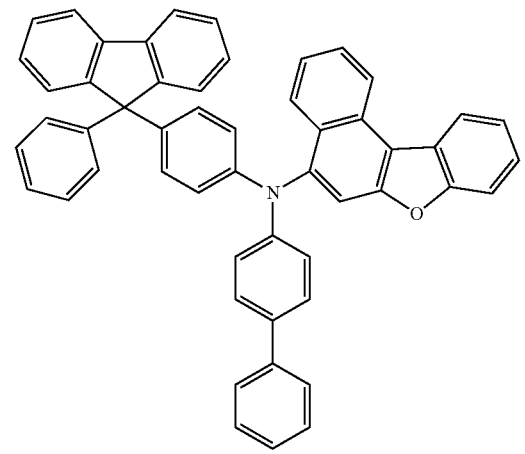
[A-33]
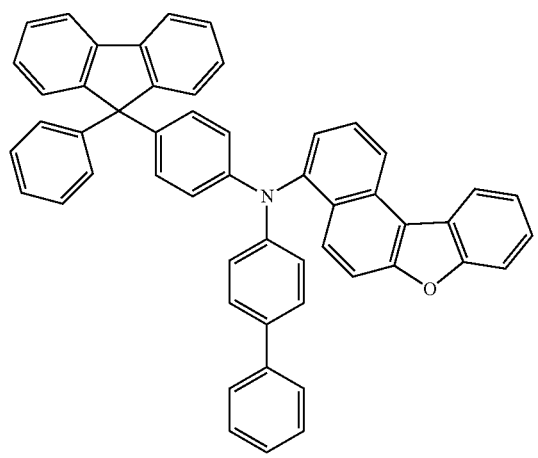
[A-36]
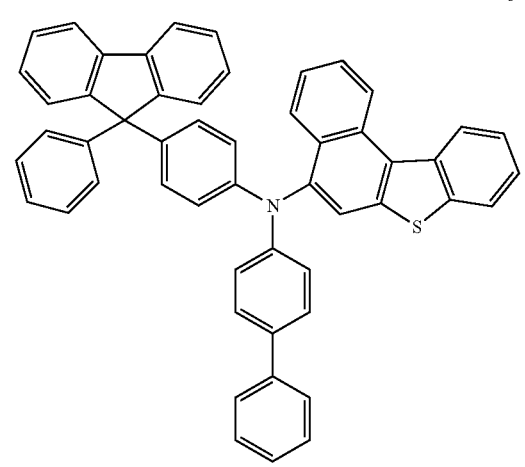

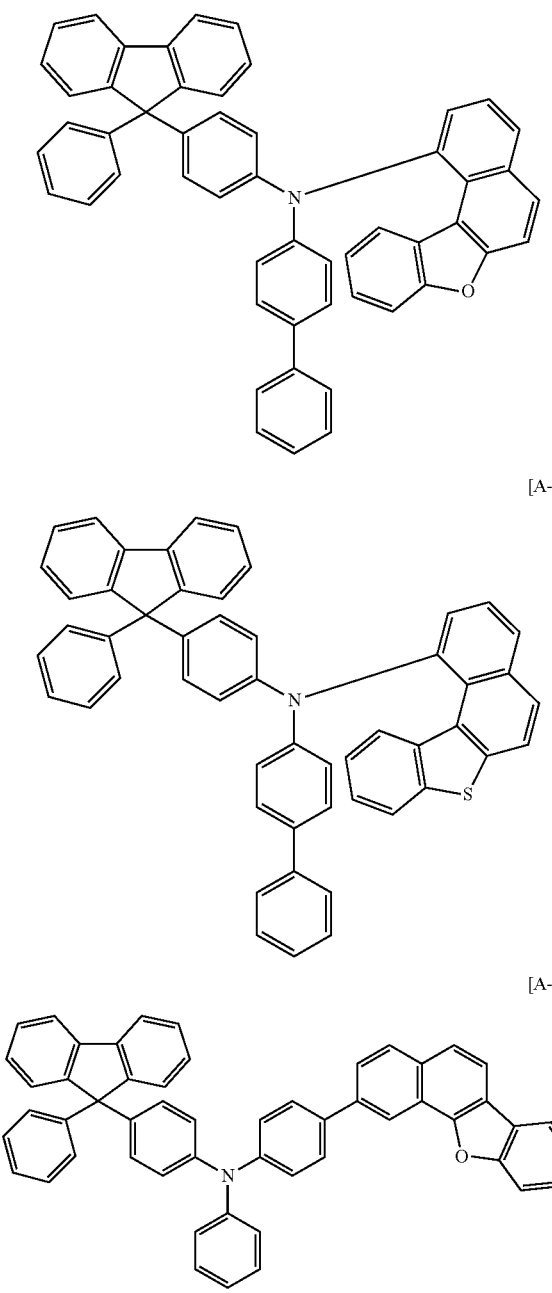
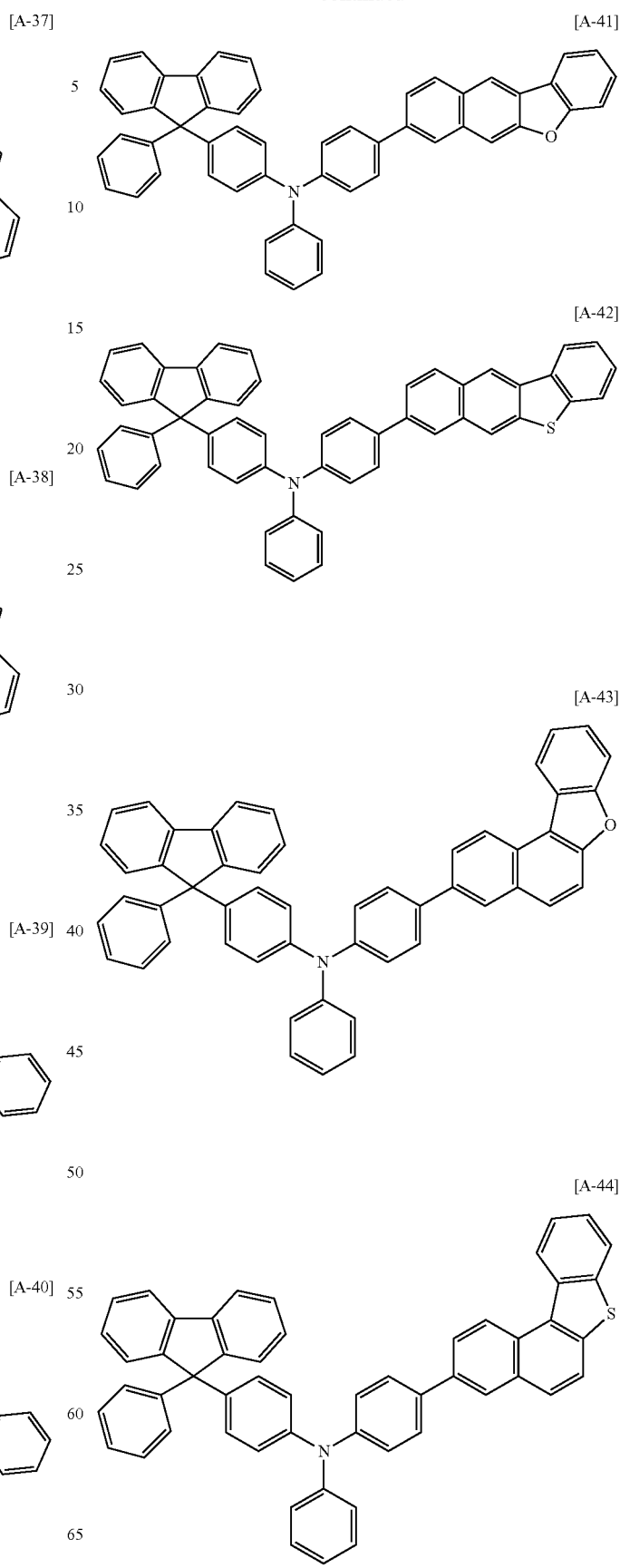

-continued
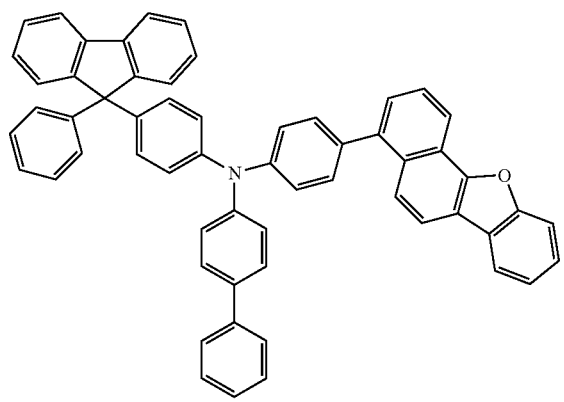
[A-45]
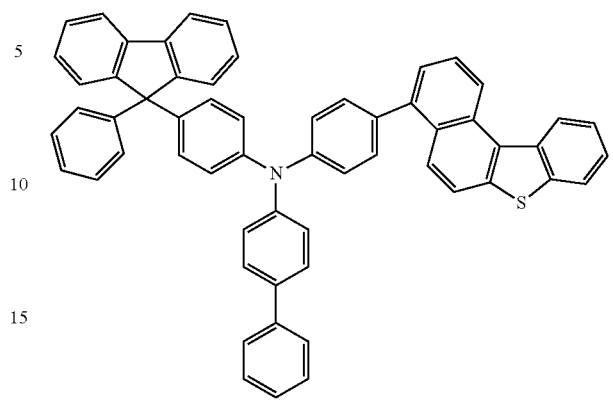
[A-48]
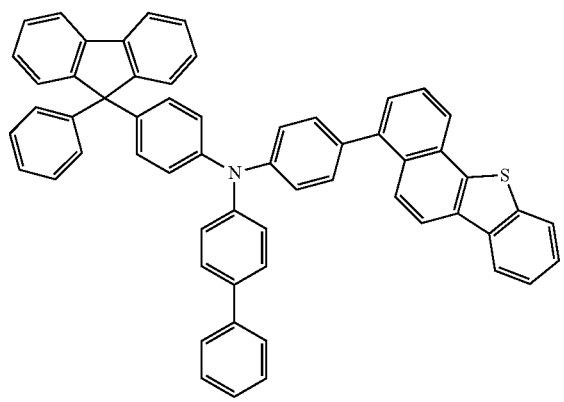
[A-46]
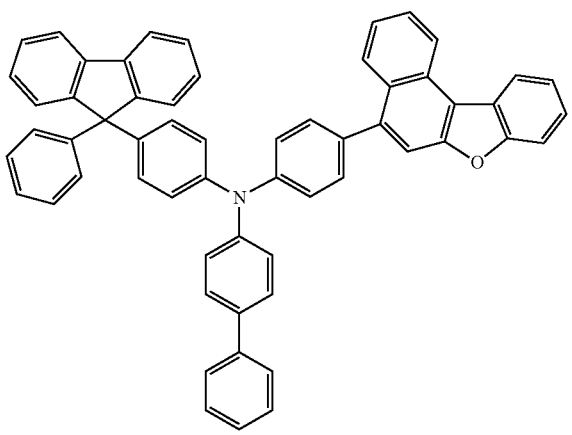
[A-49]
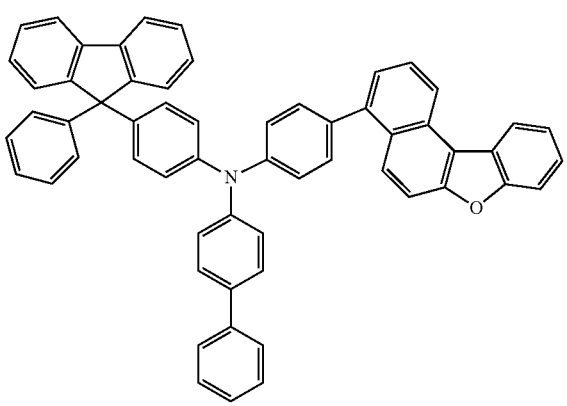
[A-47]
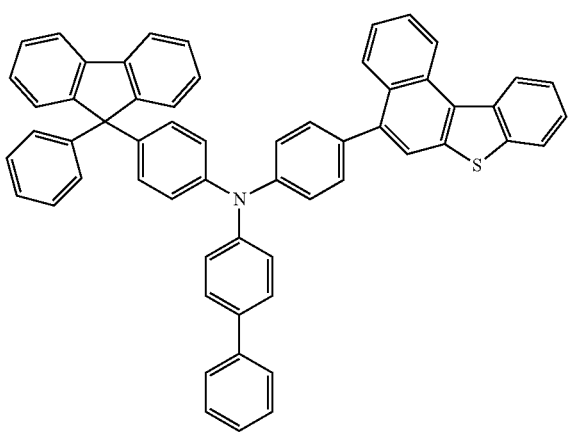
[A-50]

[A-51]
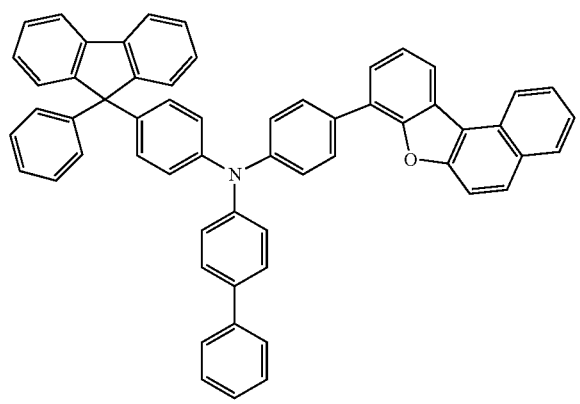
[A-54]
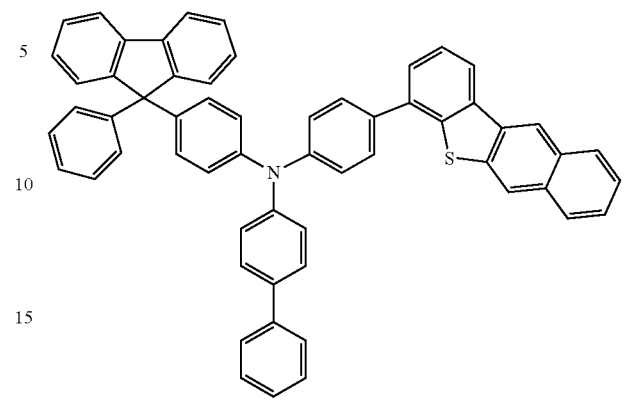
[A-52]
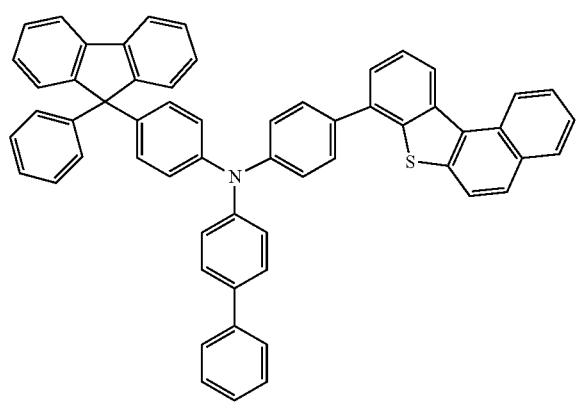
[A-55]
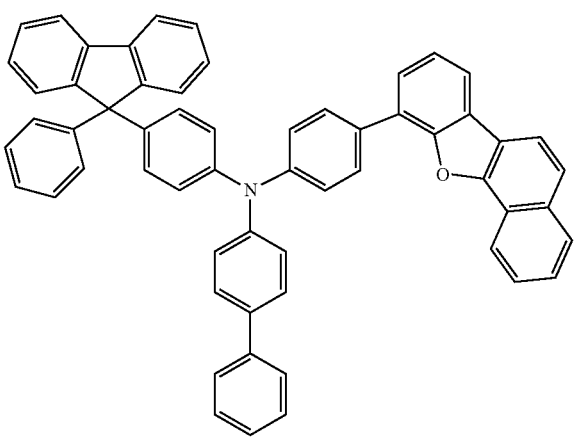
[A-53]
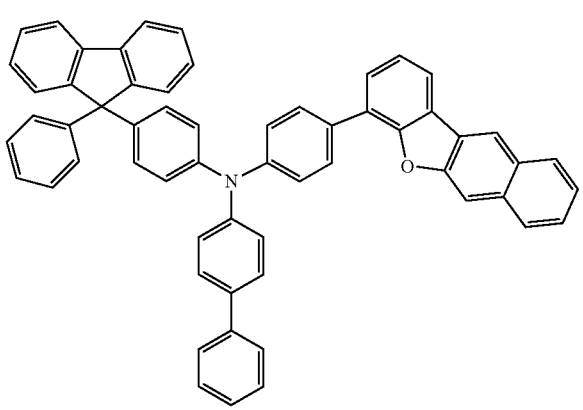
[A-56]
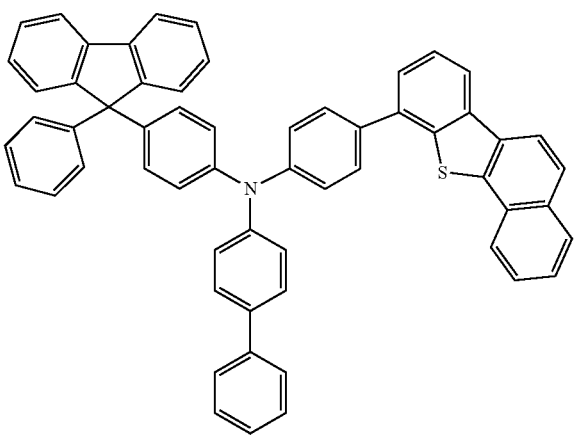

[A-57]
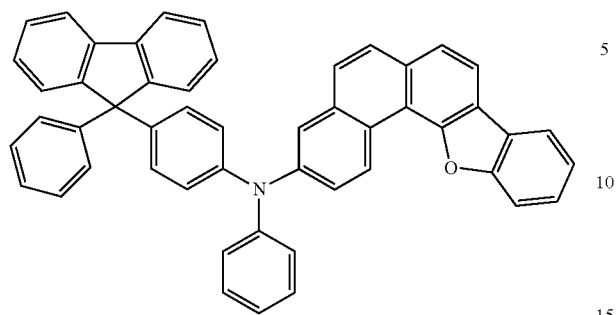
[A-58]
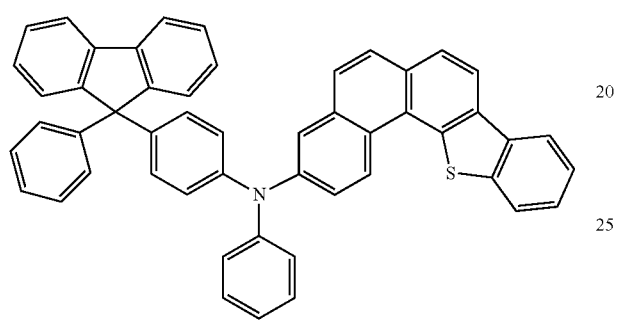
[A-59]
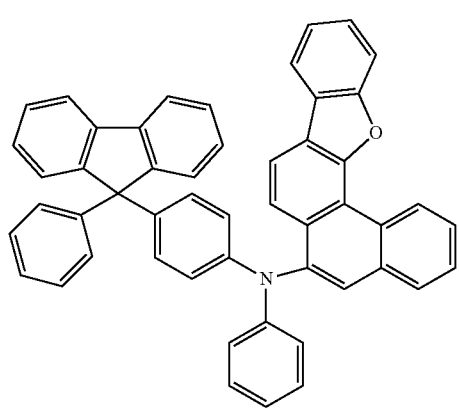
[A-60]
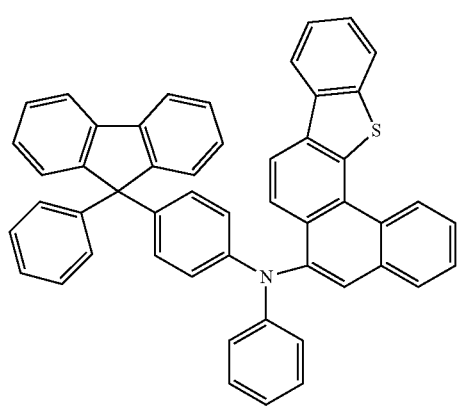
[A-61]
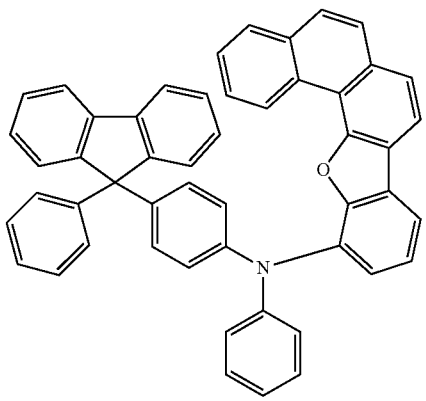
[A-62]
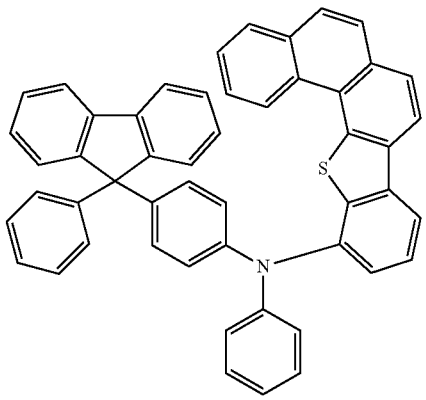
[A-63]
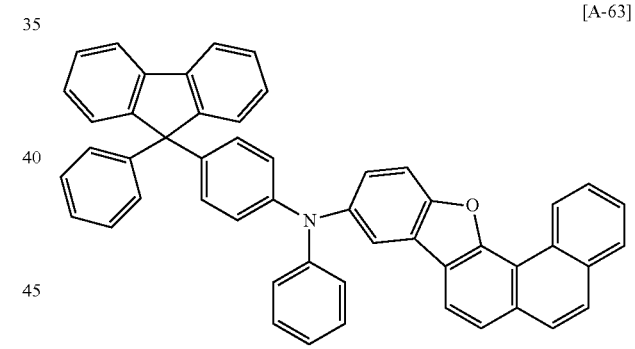
[A-64]
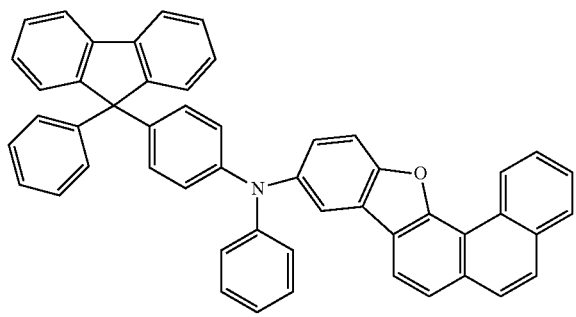

[A-65]
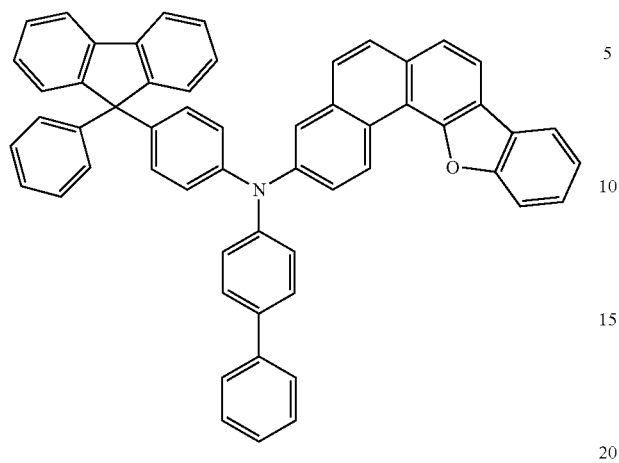
[A-68]
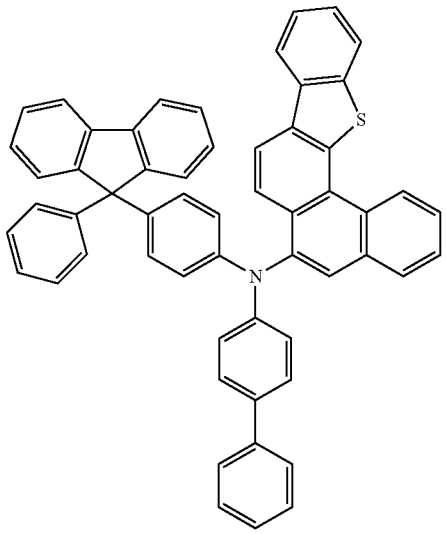
[A-66]
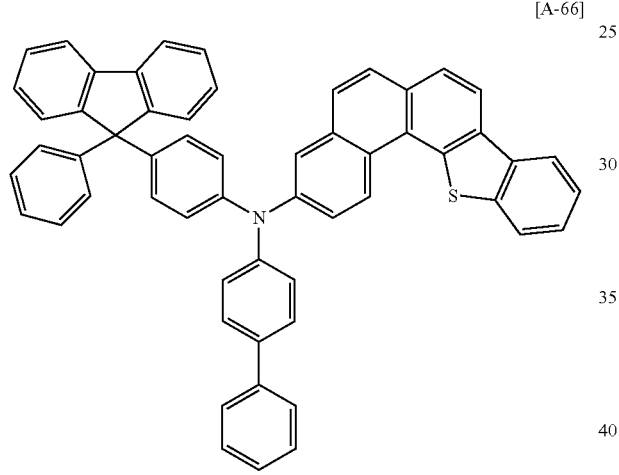
[A-69]
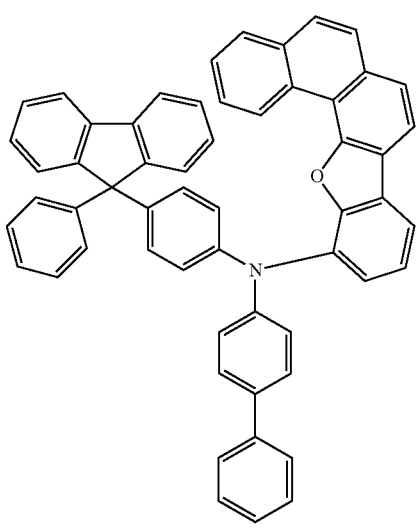
[A-67]
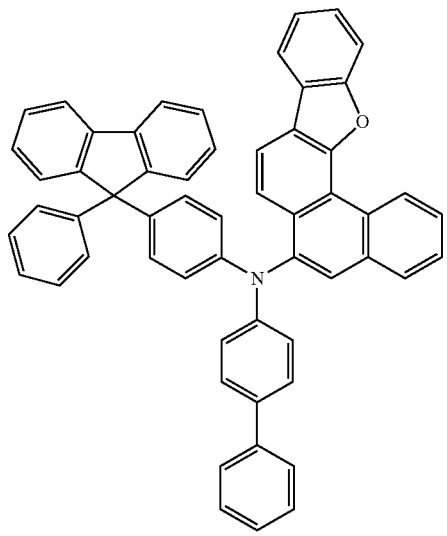
[A-70]
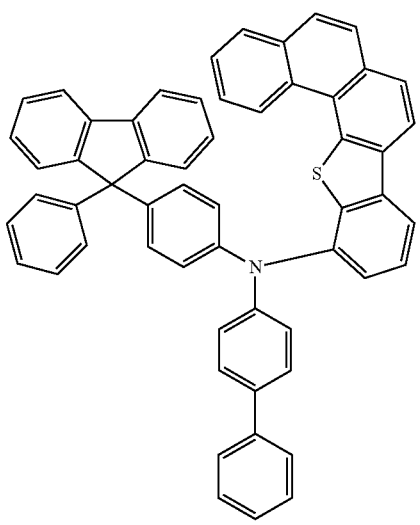

[A-71A]
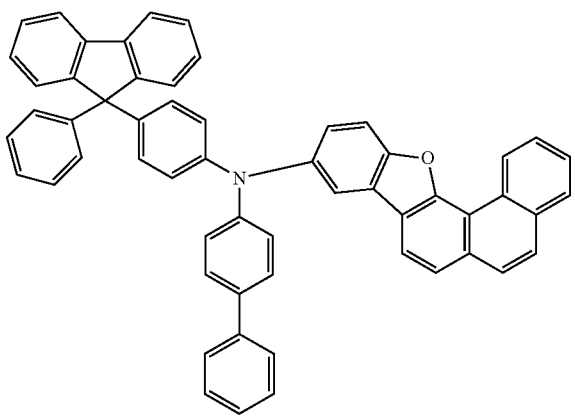
[A-71B]
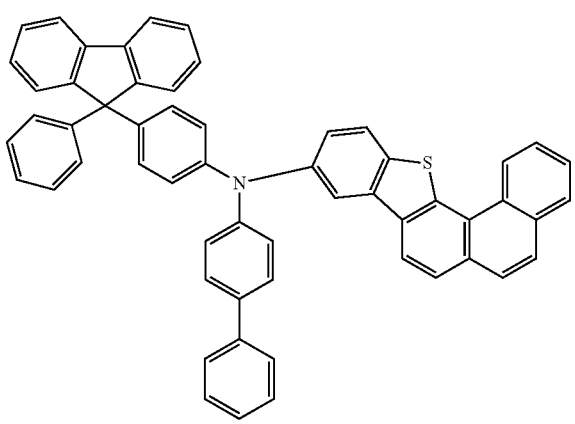
[A-72]
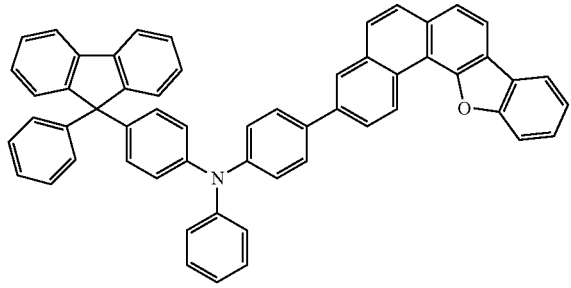
[A-73]
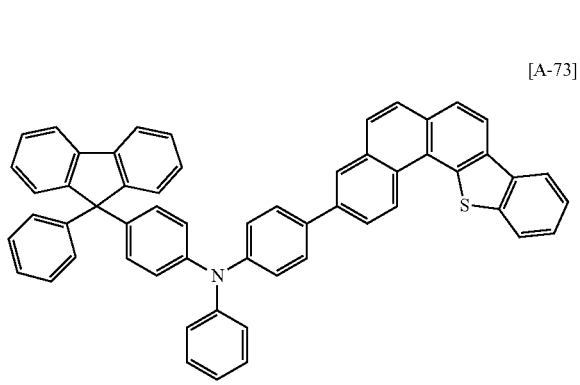
[A-74]
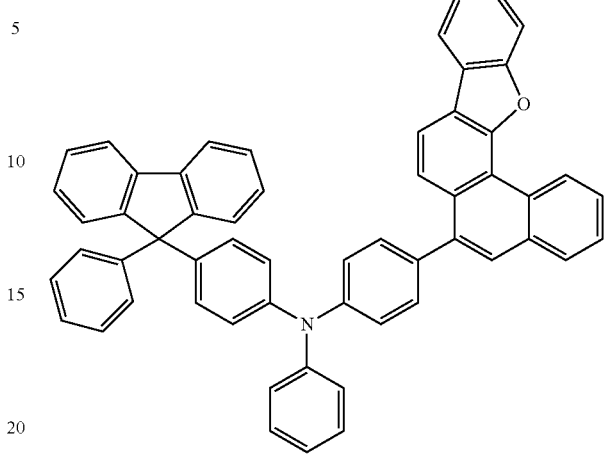
[A-75]
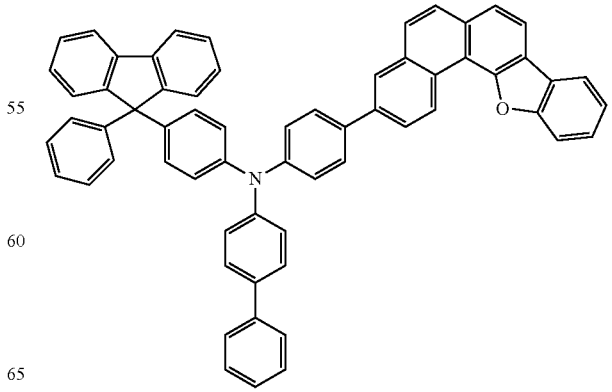
[A-76]

[A-77]
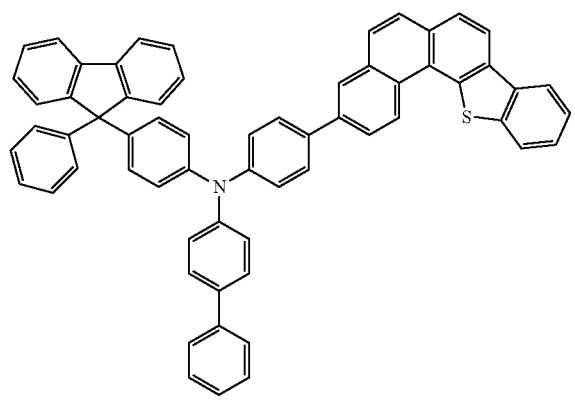
[A-78]
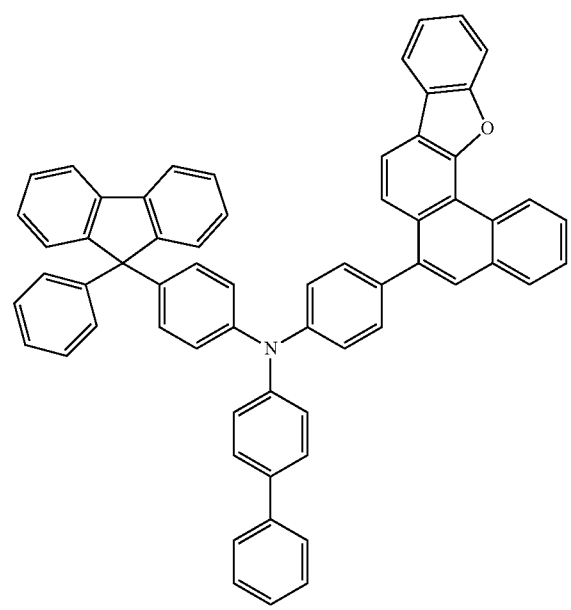
[A-79]
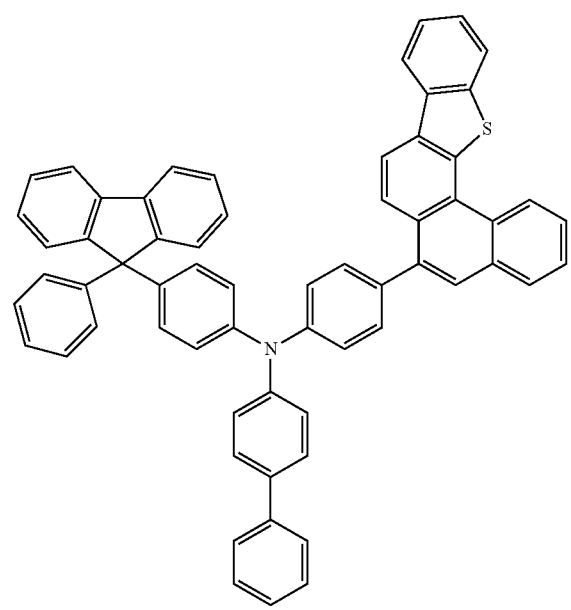
[A-80]
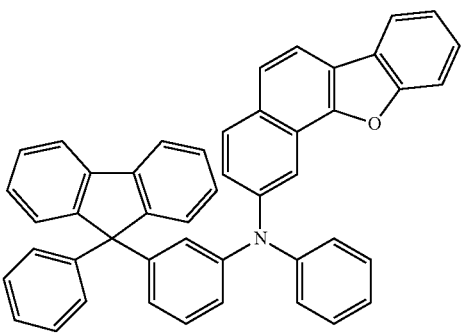
[A-81]
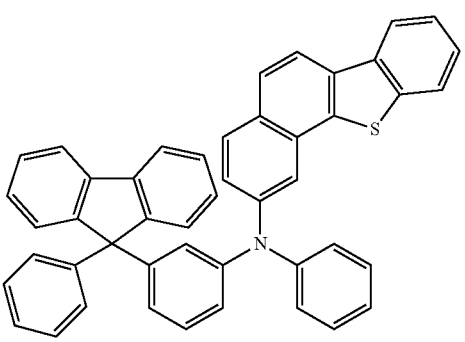
[A-82]
[A-83]
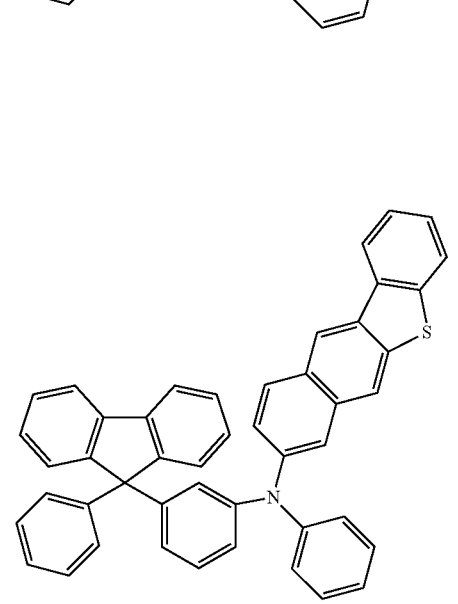

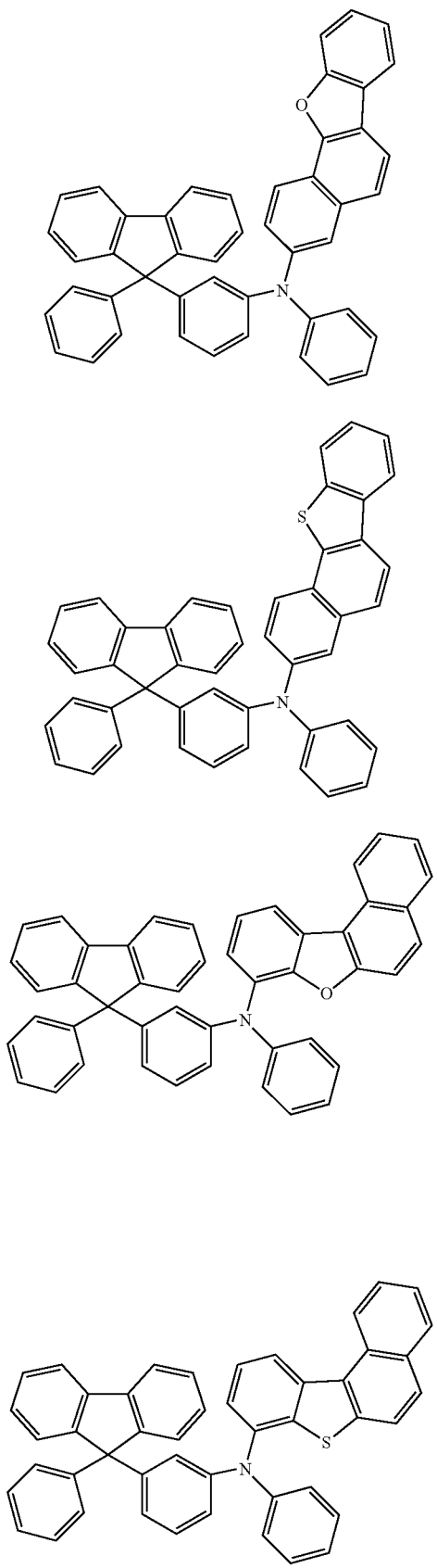
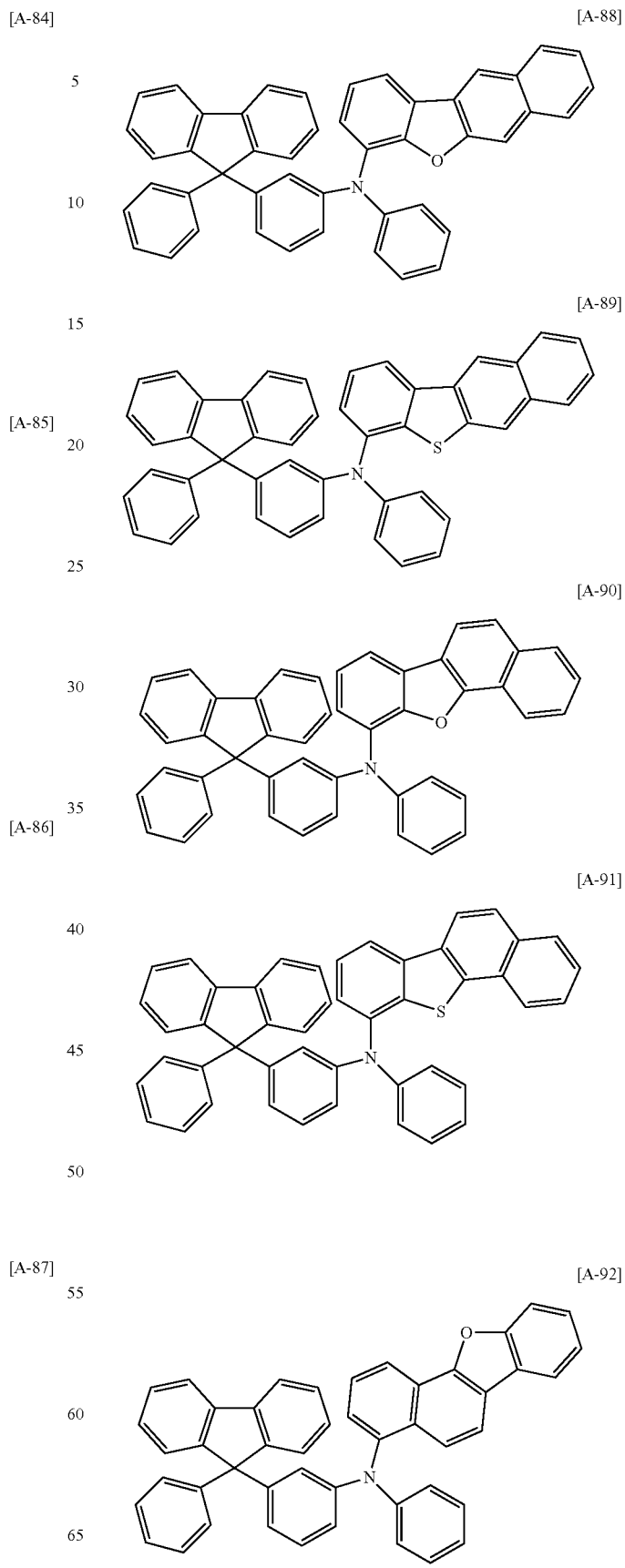

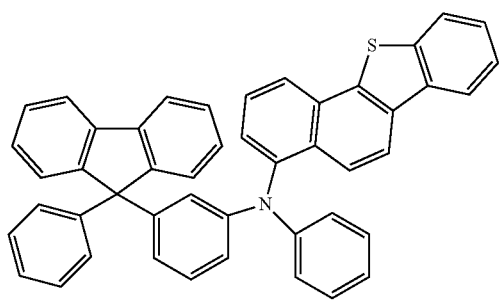
[A-93]
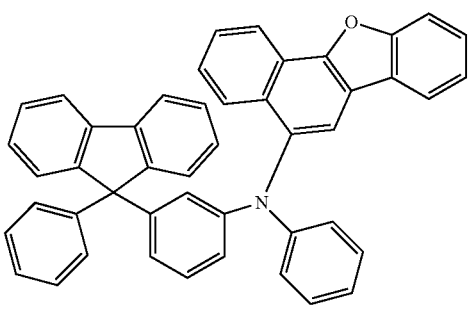
[A-94]
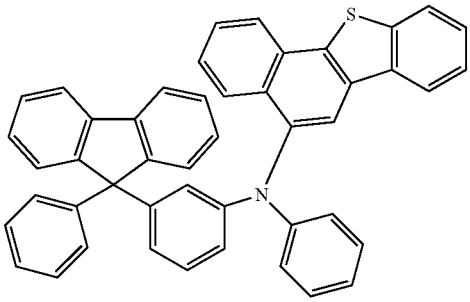
[A-95]
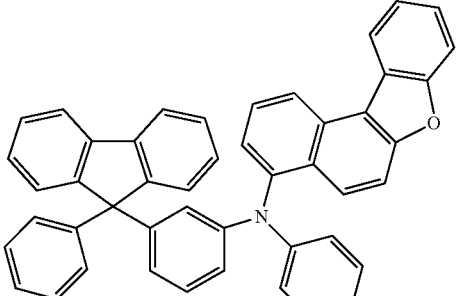
[A-96]
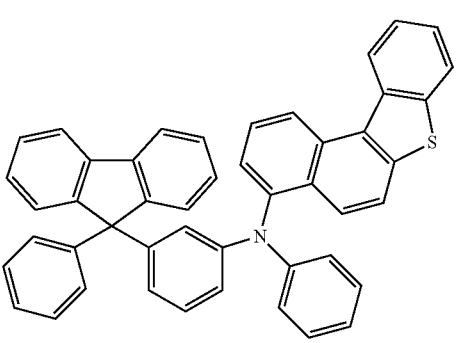
[A-97]
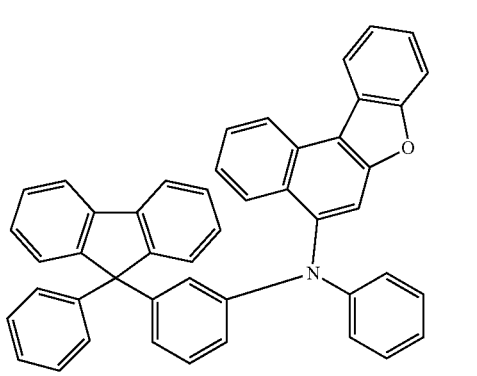
[A-98]
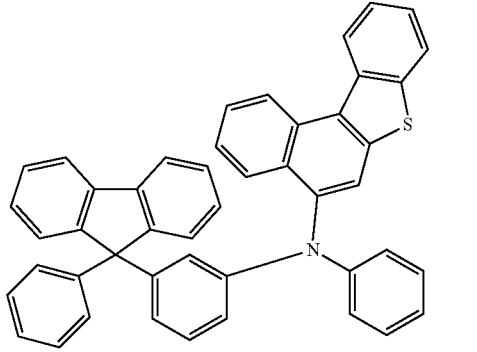
[A-99]
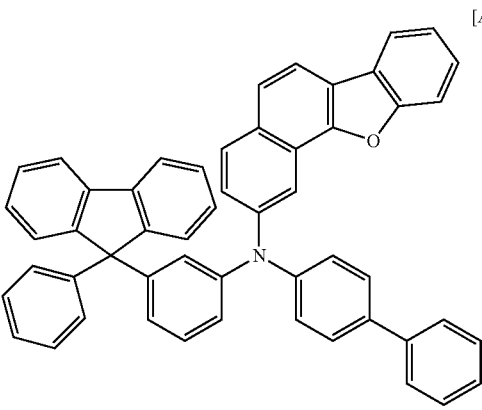
[A-100]
[A-101]

[A-102]
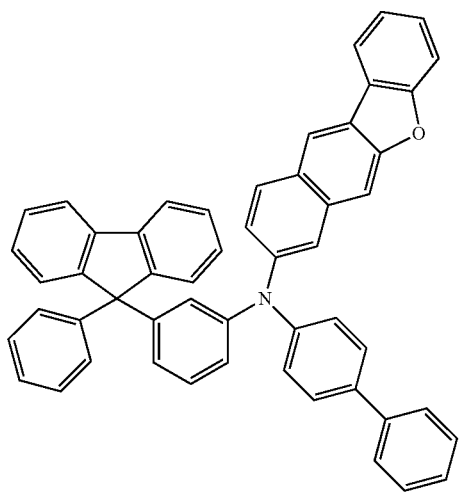
[A-103]
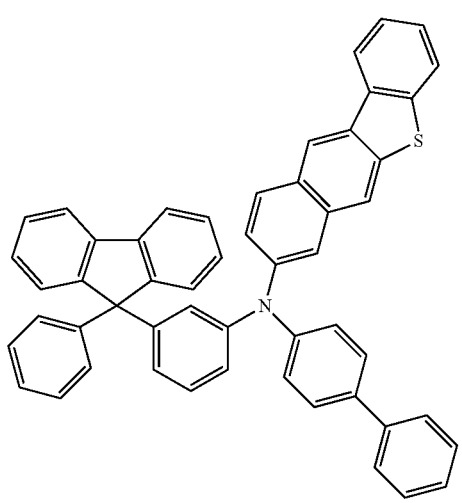
[A-104]
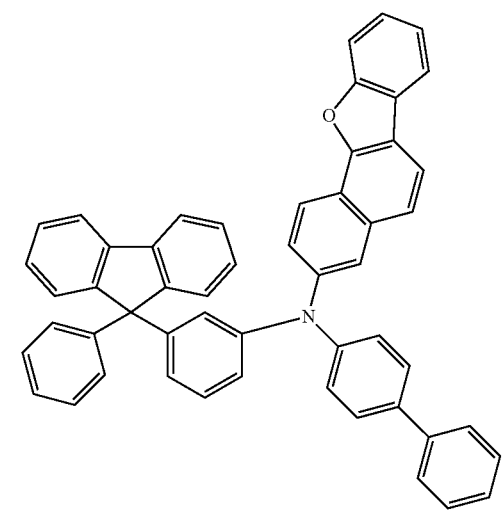
[A-105]
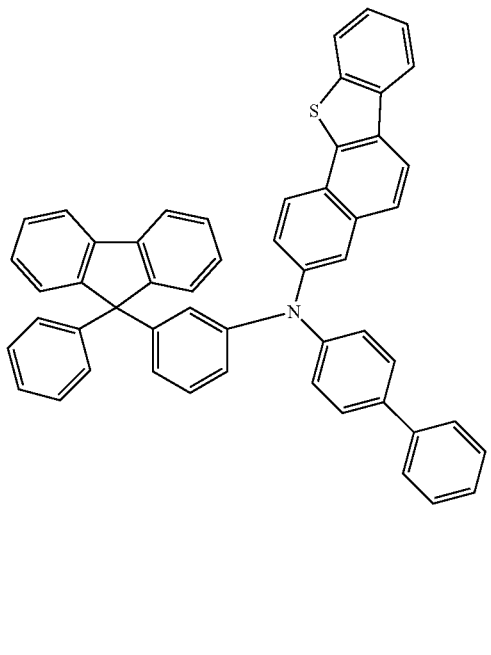
[A-106]
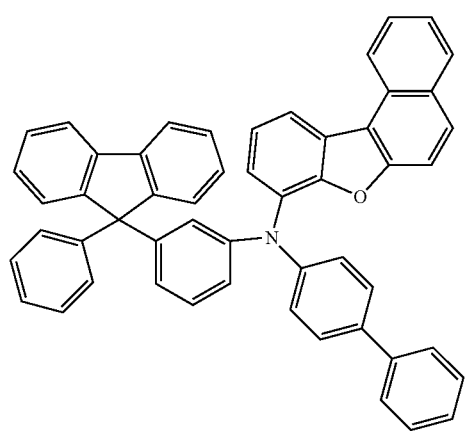
[A-107]
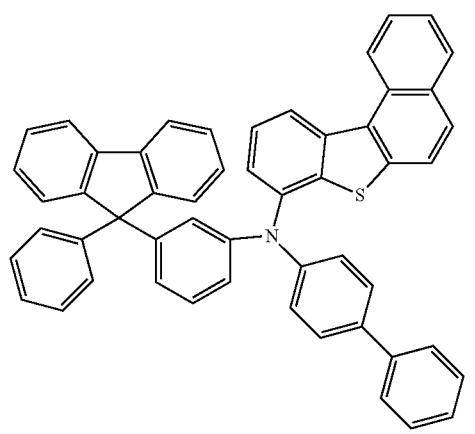

-continued
[A-108]
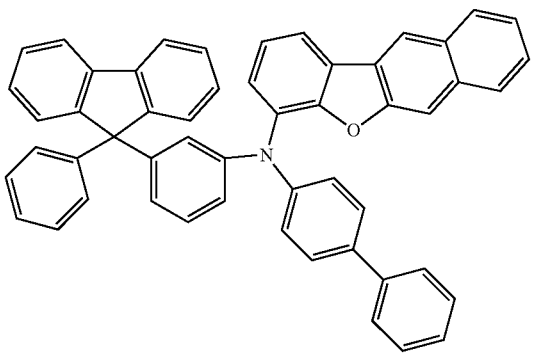
[A-109]
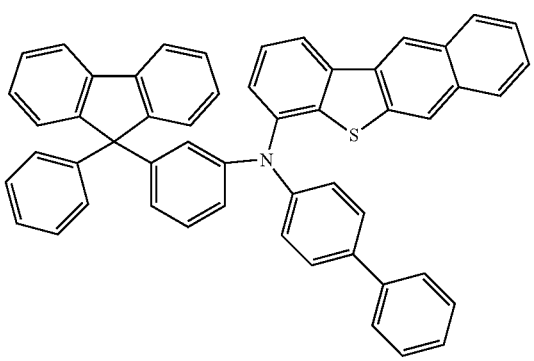
[A-110]
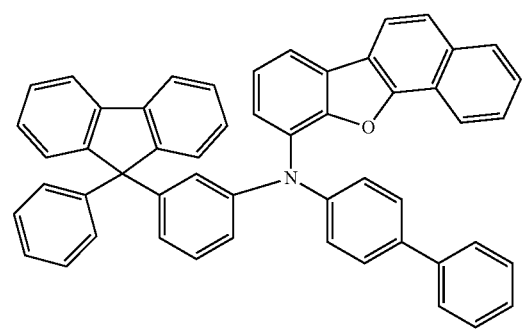
[A-111]
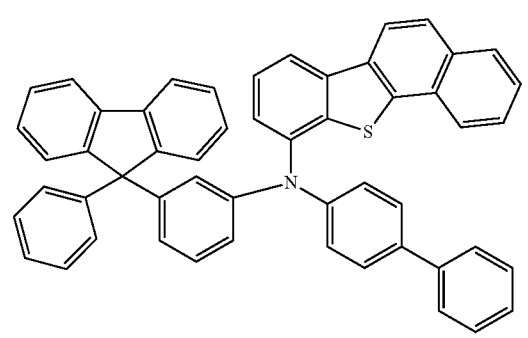
[A-112]
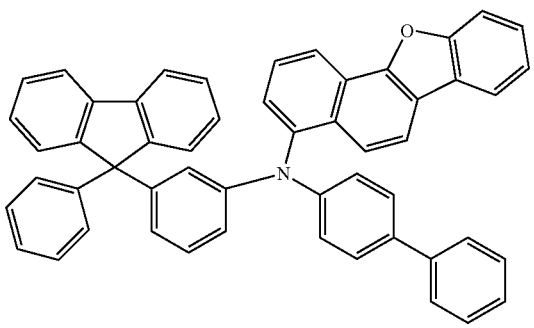
[A-113]
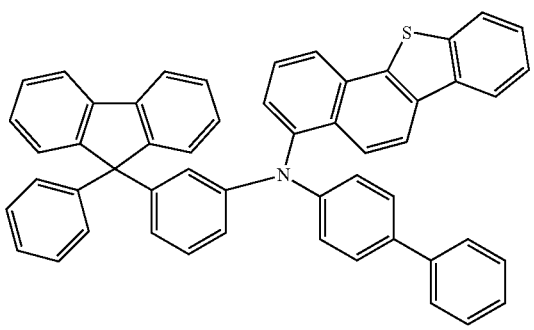
[A-114]
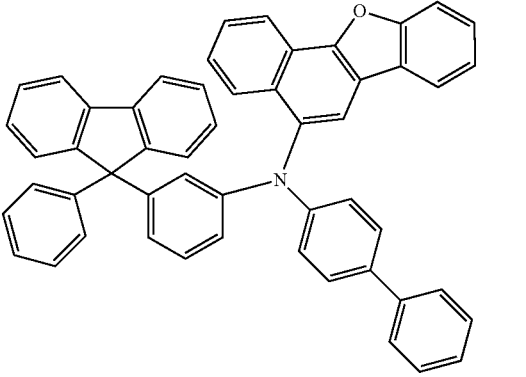
[A-115]
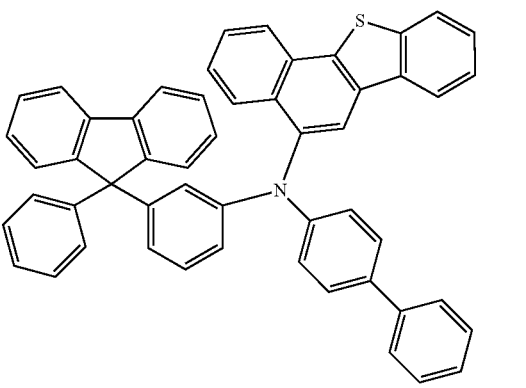

[A-116]
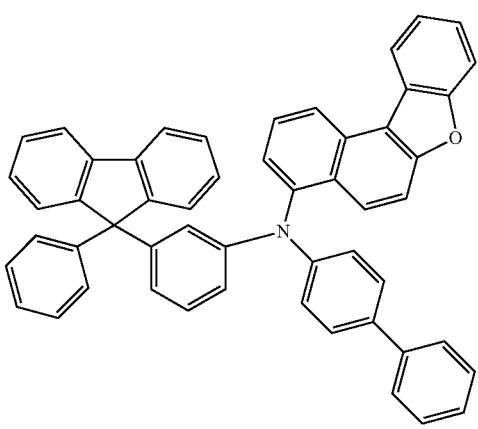
[A-117]
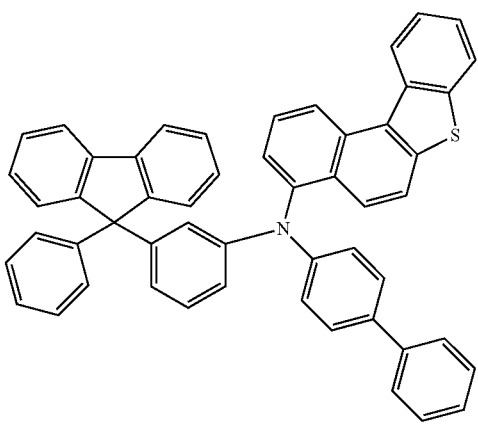
[A-118]
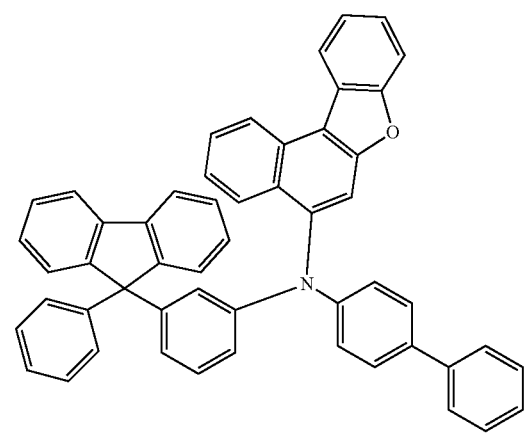
[A-119]
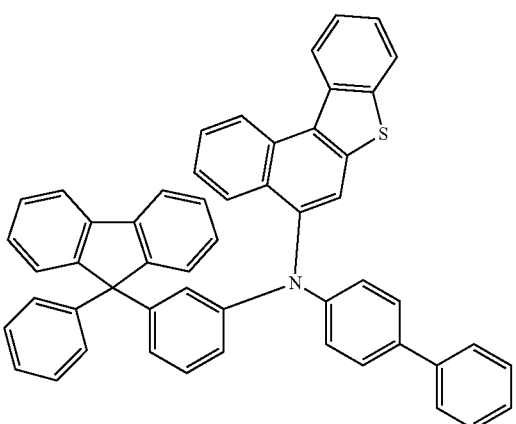
[A-120]
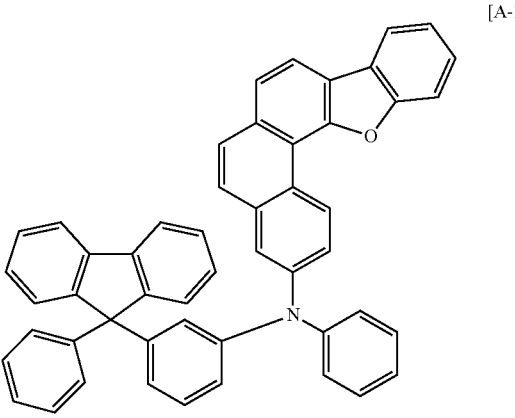
[A-121]
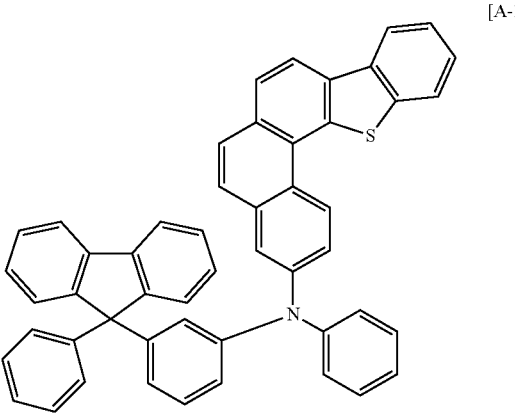
[A-122]
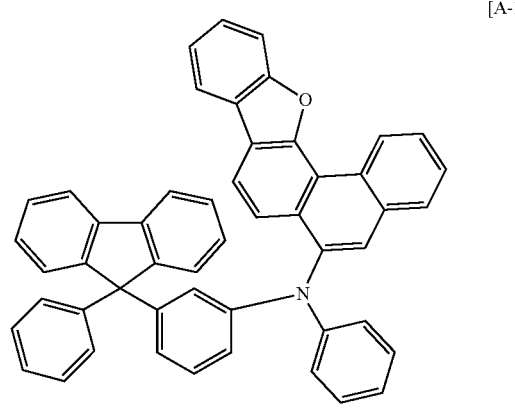

[A-123]
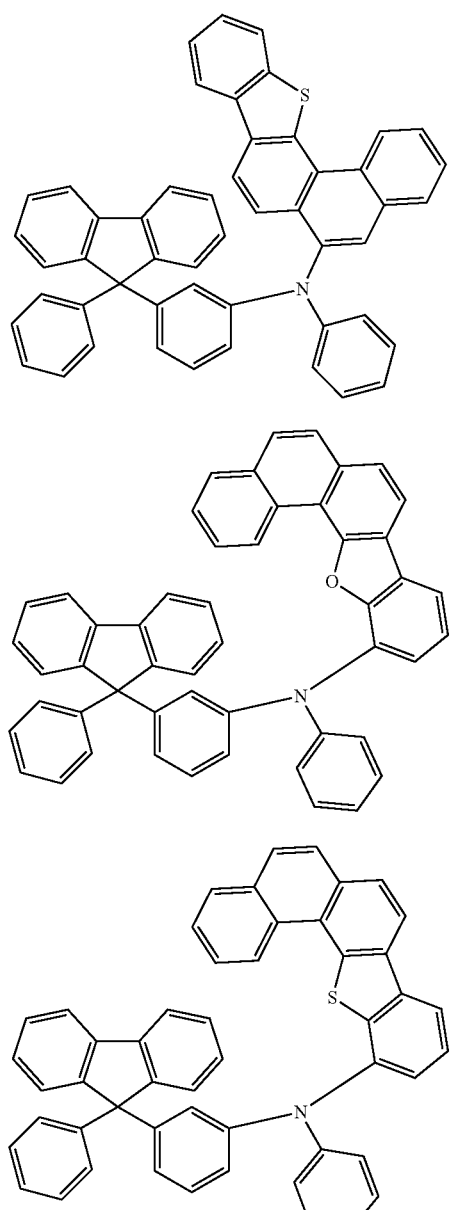
[A-124]
[A-125]
[A-126]
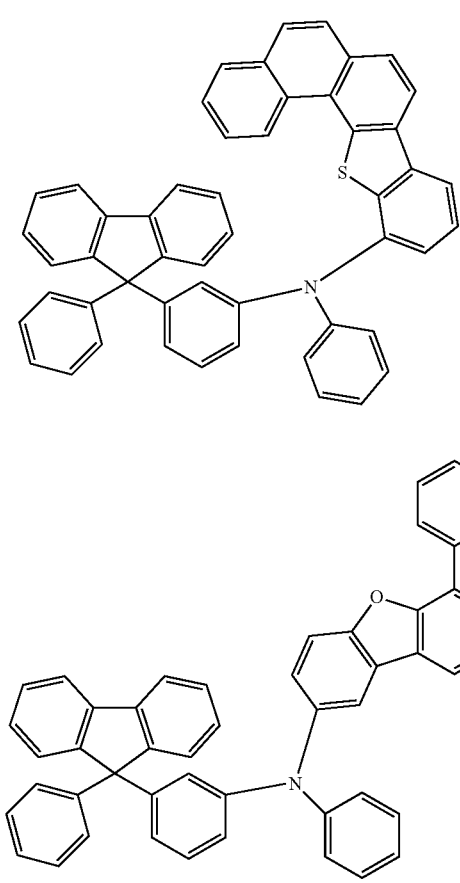
[A-127]
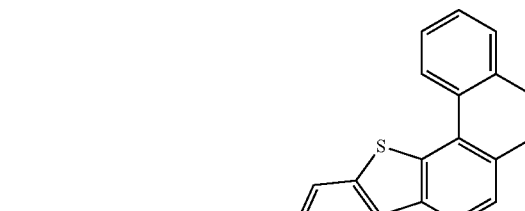
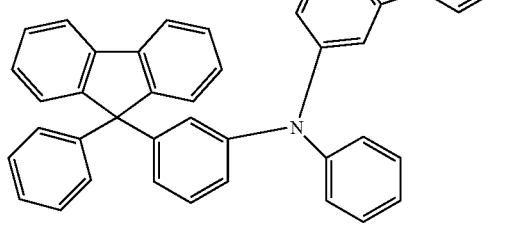
[A-128]
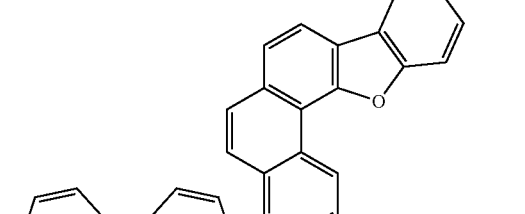
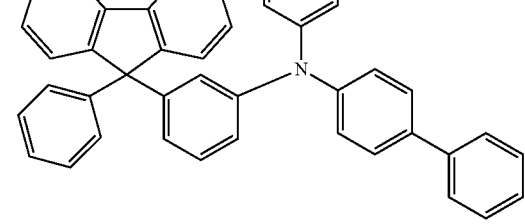
[A-129]
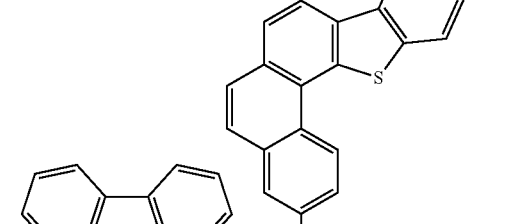
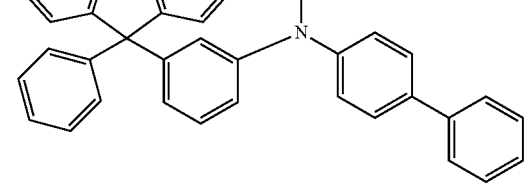

[A-130]
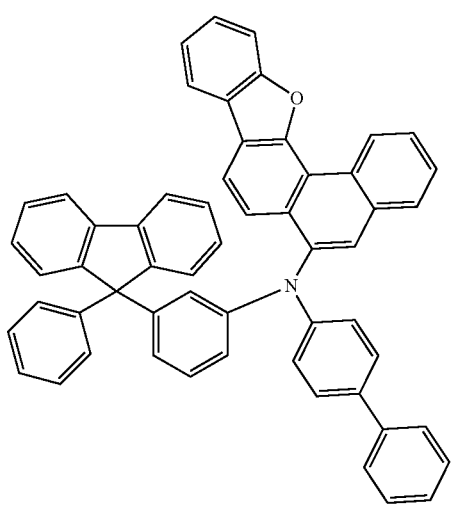
[A-133]
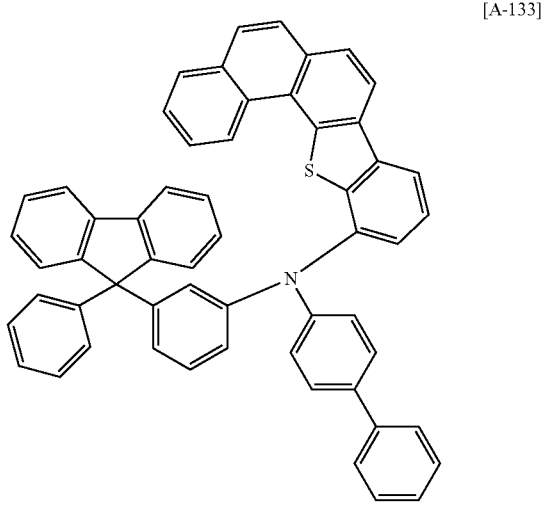
[A-131]
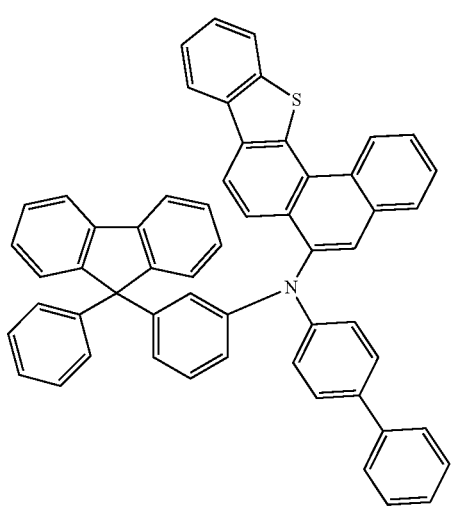
[A-134]
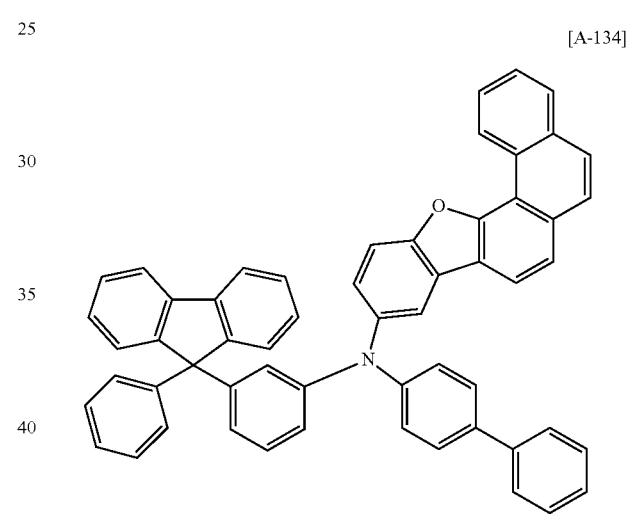
[A-132]
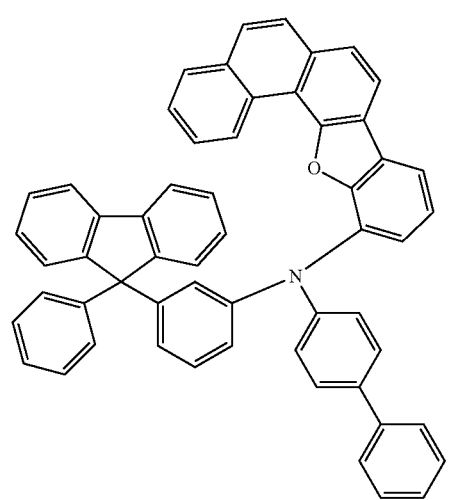
[A-135]
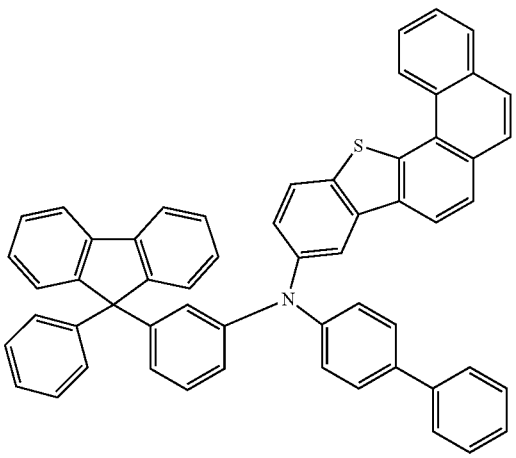

[A-136]
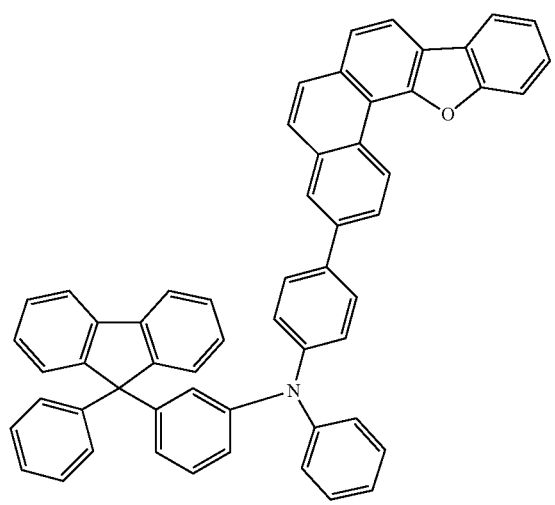
[A-137]
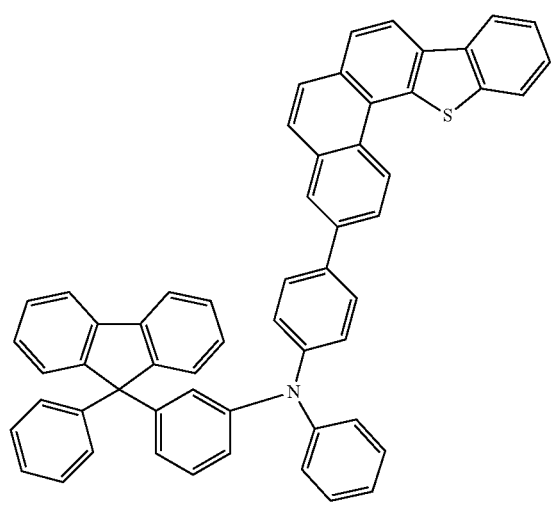
[A-138]
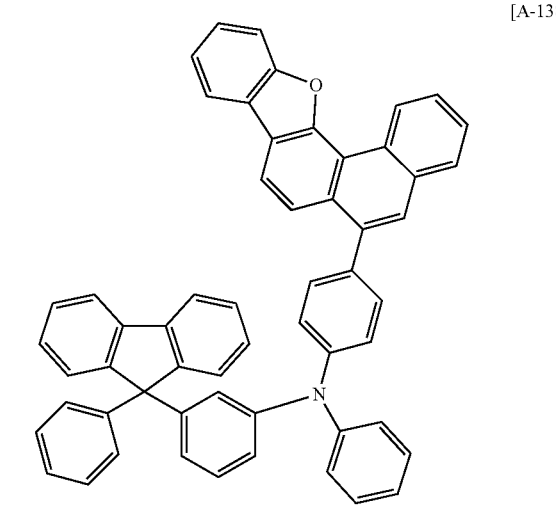
[A-139]
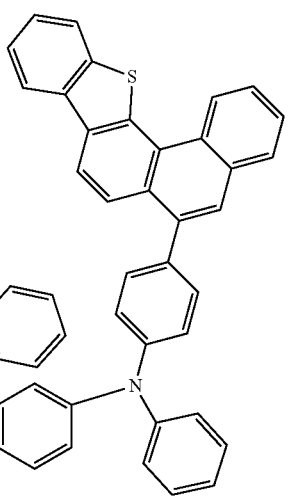
[A-140]
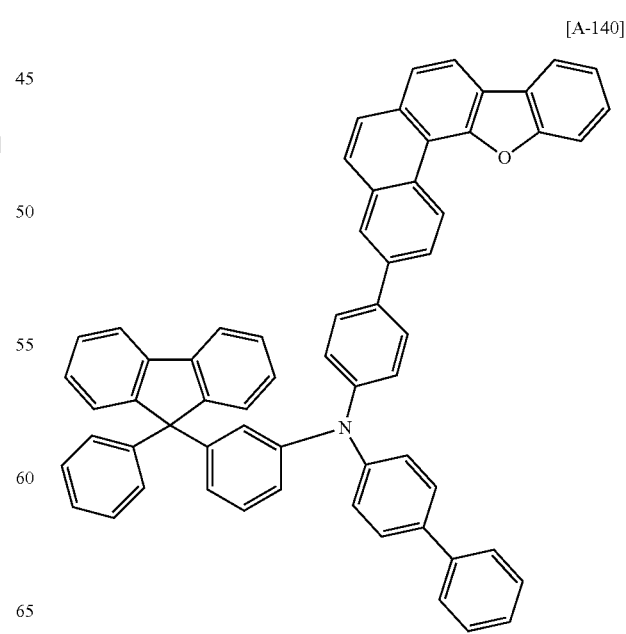

[A-141]
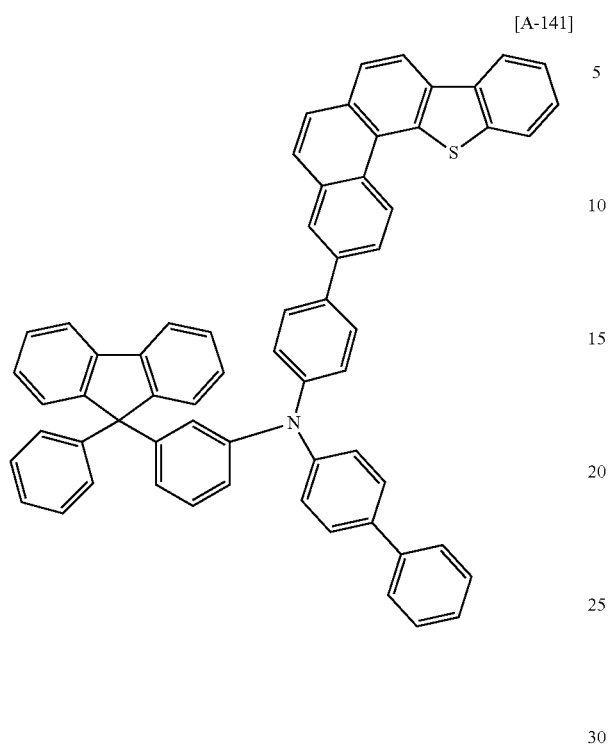
[A-143]
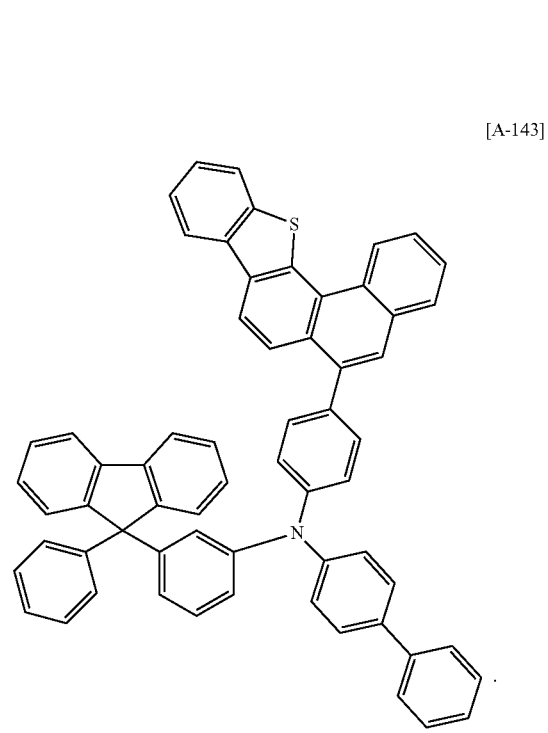
[A-142]
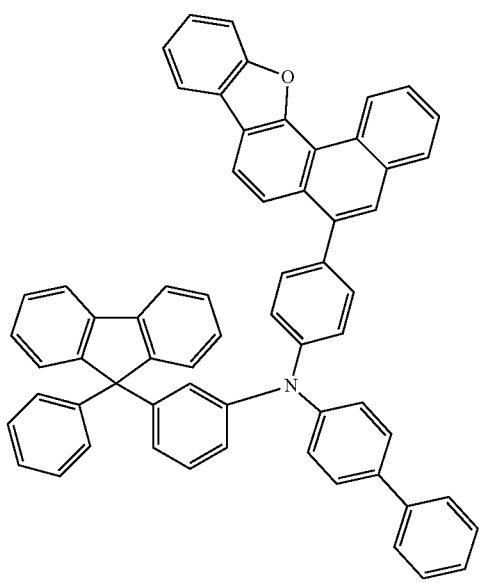
8. A display device comprising the organic optoelectronic device of claim 1.
9. The organic optoelectronic device of claim 1, wherein X is O, $SO_2$, or $SiR^cR^d$.
10. The organic optoelectronic device of claim 1, wherein the organic compound is neither of Compound A-32 or Compound A-56:
[A-32]
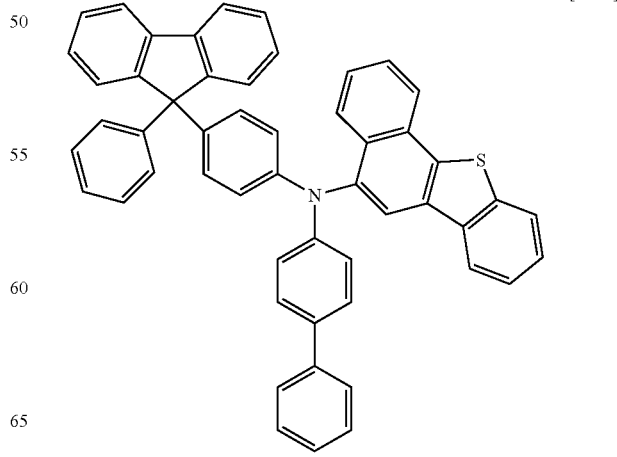

-continued
[A-56]
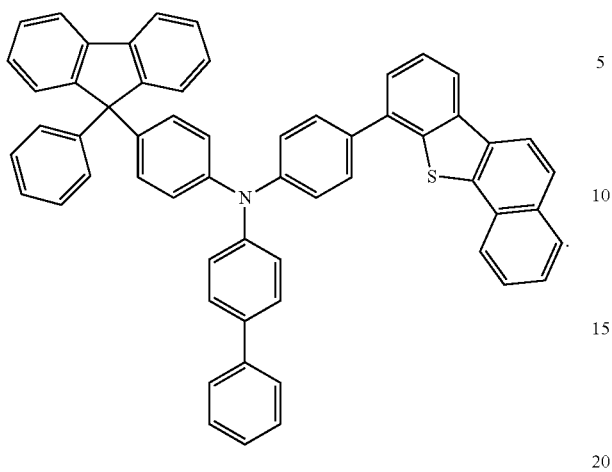
* * * * *